United States Patent
Demaria et al.

(10) Patent No.: US 10,655,144 B2
(45) Date of Patent: *May 19, 2020

(54) NUCLEIC ACID CONSTRUCT WITH A P16 PROMOTER THAT CAUSES A PRODRUG CONVERTING ENZYME TO BE EXPRESSED SPECIFICALLY IN SENESCENT CELLS

(71) Applicant: Buck Institute for Research on Aging, Novato, CA (US)

(72) Inventors: Marco Demaria, Groningen (NL); Francis Rodier, Novato, CA (US); Remi-Martin Laberge, San Francisco, CA (US); Judith Campisi, Berkeley, CA (US)

(73) Assignee: Buck Institute for Research on Aging, Novato, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/870,172

(22) Filed: Jan. 12, 2018

(65) Prior Publication Data

US 2018/0139939 A1    May 24, 2018

Related U.S. Application Data

(63) Continuation of application No. 15/067,543, filed on Mar. 11, 2016, now Pat. No. 9,901,080, which is a continuation of application No. 13/975,179, filed on Aug. 23, 2013, now abandoned.

(60) Provisional application No. 61/692,613, filed on Aug. 23, 2012, provisional application No. 61/837,096, filed on Jun. 19, 2013.

(51) Int. Cl.
| C12N 15/85 | (2006.01) |
| A01K 67/027 | (2006.01) |
| A61K 49/00 | (2006.01) |

(52) U.S. Cl.
CPC ...... *C12N 15/8509* (2013.01); *A01K 67/0275* (2013.01); *A01K 2217/052* (2013.01); *A01K 2227/105* (2013.01); *A01K 2267/0393* (2013.01); *A61K 49/0008* (2013.01); *C12N 2015/859* (2013.01); *C12N 2015/8527* (2013.01); *C12N 2830/008* (2013.01)

(58) Field of Classification Search
CPC ........ C12N 15/8509; C12N 2015/8527; C12N 2830/008; C12N 2015/859; A01K 67/0275; A01K 2217/052; A01K 2267/0393; A01K 2227/105; A61K 49/0008
USPC ................. 435/320.1, 325; 800/18
See application file for complete search history.

(56) References Cited

U.S. PATENT DOCUMENTS

| | | |
|---|---|---|
| 4,873,191 A | 10/1989 | Wagner et al. |
| 6,201,020 B1 | 3/2001 | Zhang et al. |
| 7,390,799 B2 | 6/2008 | Bruncko et al. |
| 7,642,260 B2 | 1/2010 | Bruncko et al. |
| 7,767,684 B2 | 8/2010 | Bruncko et al. |
| 7,829,556 B2 | 11/2010 | Bemis et al. |
| 7,842,681 B2 | 11/2010 | Elmore et al. |
| 7,851,626 B2 | 12/2010 | Ding et al. |
| 7,879,857 B2 | 2/2011 | Mabire et al. |
| 7,928,104 B2 | 4/2011 | Mabire et al. |
| 7,973,161 B2 | 7/2011 | Bruncko et al. |
| 8,071,623 B2 | 12/2011 | Jones et al. |
| 8,168,645 B2 | 5/2012 | Baell et al. |
| 8,343,967 B2 | 1/2013 | Ding et al. |
| 8,426,422 B2 | 4/2013 | Hexamer et al. |
| 8,518,970 B2 | 8/2013 | Baell et al. |
| 8,541,417 B2 | 9/2013 | Brown et al. |
| 8,557,983 B2 | 10/2013 | Bruncko et al. |
| 8,563,735 B2 | 10/2013 | Bruncko et al. |
| 8,586,754 B2 | 11/2013 | Bruncko et al. |
| 8,614,318 B2 | 12/2013 | Bruncko et al. |
| 8,624,027 B2 | 1/2014 | Shah et al. |
| 9,968,076 B2 | 5/2018 | Kirkland et al. |
| 2004/0006233 A1 | 1/2004 | Holt et al. |
| 2004/0180430 A1 | 9/2004 | West et al. |
| 2005/0019865 A1 | 1/2005 | Kihm et al. |
| 2005/0181076 A1 | 8/2005 | Ziegler |
| 2007/0099186 A1 | 5/2007 | D'Adda et al. |
| 2008/0108062 A1 | 5/2008 | Sharpless et al. |
| 2008/0216180 A1 | 9/2008 | Abate-Shen et al. |

(Continued)

FOREIGN PATENT DOCUMENTS

| WO | WO-03028443 A1 | 4/2003 |
| WO | WO-2006018632 A2 | 2/2006 |

(Continued)

OTHER PUBLICATIONS

Baker et al. (2011) Nature, vol. 479, 232-237.*
Zhang et al. (2005) FEBS, vol. 272, 2207-2215.*
Ray et al. (2004) Canc. Res., vol. 64, 1323-1330.*
Baker et al. (2008) Nat. Cell. Biol., vol. 10(7), 825-836, including Supplementary Information.*

(Continued)

*Primary Examiner* — Anne Marie S Wehbe
(74) *Attorney, Agent, or Firm* — Janet Martineau; Wilson Sonsini Goodrich & Rosati

(57) ABSTRACT

This disclosure provides non-human animal models for age-related disorders and age-sensitive traits, particularly those caused by senescence-inducing stimuli, wherein the models comprise transgenes selectively expressed by senescent cells. The disclosure further provides methods for identifying therapeutic agents effective for treating or preventing age-related disorders and age-sensitive traits using the animal models, therapeutic agents identified using such methods, pharmaceutical compositions comprising the identified therapeutic agents, and methods of treating or preventing age-related disorders and age-sensitive traits.

10 Claims, 16 Drawing Sheets

Specification includes a Sequence Listing.

(56) References Cited

U.S. PATENT DOCUMENTS

| | | |
|---|---|---|
| 2008/0221132 A1 | 9/2008 | Cai et al. |
| 2008/0234362 A1 | 9/2008 | Chandler |
| 2009/0019554 A1 | 1/2009 | Selkirk et al. |
| 2009/0022465 A1 | 1/2009 | Chen et al. |
| 2009/0193533 A1 | 7/2009 | Edge et al. |
| 2009/0281129 A1 | 11/2009 | Chang et al. |
| 2010/0016218 A1 | 1/2010 | Lichter et al. |
| 2010/0028302 A1 | 2/2010 | Hoflich et al. |
| 2010/0125064 A1 | 5/2010 | Boettcher et al. |
| 2010/0190807 A1 | 7/2010 | Porter et al. |
| 2010/0260733 A1 | 10/2010 | Qi |
| 2010/0292200 A1 | 11/2010 | Kile et al. |
| 2010/0310504 A1 | 12/2010 | Lowe et al. |
| 2011/0023137 A1 | 1/2011 | Chu et al. |
| 2011/0189142 A1 | 8/2011 | May et al. |
| 2011/0212909 A1 | 9/2011 | Wen et al. |
| 2012/0108590 A1 | 5/2012 | Birtalan et al. |
| 2012/0156134 A1 | 6/2012 | Squires |
| 2012/0183534 A1 | 7/2012 | Gruber |
| 2013/0096121 A1 | 4/2013 | Wang et al. |
| 2013/0267534 A1 | 10/2013 | Bruncko et al. |
| 2013/0287763 A1 | 10/2013 | Sathyanarayanan et al. |
| 2013/0288980 A1 | 10/2013 | De et al. |
| 2013/0302283 A1 | 11/2013 | Kihm |
| 2014/0017341 A1 | 1/2014 | Gourlaouen |
| 2014/0073640 A1 | 3/2014 | Judd et al. |
| 2014/0189897 A1 | 7/2014 | Kirkland et al. |
| 2014/0275082 A1 | 9/2014 | Tao et al. |
| 2014/0329854 A1 | 11/2014 | Larsen et al. |
| 2014/0378683 A1 | 12/2014 | Porter et al. |
| 2015/0044184 A1 | 2/2015 | Chen et al. |
| 2015/0056195 A1 | 2/2015 | Bertolotto-Ballotti |
| 2015/0064137 A1 | 3/2015 | Lichtsteiner et al. |
| 2015/0072950 A1 | 3/2015 | Sauve et al. |
| 2015/0072972 A1 | 3/2015 | Mevellec et al. |
| 2015/0140036 A1 | 5/2015 | Mannick et al. |
| 2015/0151001 A1 | 6/2015 | Squires |
| 2015/0210717 A1 | 7/2015 | Günes et al. |
| 2015/0296755 A1 | 10/2015 | Kirkland et al. |
| 2016/0010110 A1 | 1/2016 | Scholz et al. |
| 2016/0051700 A1 | 2/2016 | Scholz et al. |
| 2017/0027139 A1 | 2/2017 | Van Deursen et al. |
| 2017/0042129 A1 | 2/2017 | Campisi et al. |

FOREIGN PATENT DOCUMENTS

| | | |
|---|---|---|
| WO | WO-2008113131 A1 | 9/2008 |
| WO | WO-2009039553 A1 | 4/2009 |
| WO | WO-2009085216 A2 | 7/2009 |
| WO | WO-2009105234 A2 | 8/2009 |
| WO | WO-2009105533 A2 | 8/2009 |
| WO | WO-2010000491 A1 | 1/2010 |
| WO | WO-2010134790 A2 | 11/2010 |
| WO | WO-2010148447 A1 | 12/2010 |
| WO | WO-2011068561 A1 | 6/2011 |
| WO | WO-201150016 A1 | 12/2011 |
| WO | WO-2012177927 A1 | 12/2012 |
| WO | WO-2013152038 A1 | 10/2013 |
| WO | WO-2013170174 A1 | 11/2013 |
| WO | WO-2014041125 A1 | 3/2014 |
| WO | WO-2014089124 A1 | 6/2014 |
| WO | WO-2014160661 A2 | 10/2014 |
| WO | WO-2014174511 A1 | 10/2014 |
| WO | WO-2014186878 A1 | 11/2014 |
| WO | WO-2015044649 A1 | 4/2015 |
| WO | WO-2015051766 A1 | 4/2015 |
| WO | WO-2015066442 A1 | 5/2015 |
| WO | WO-2015070280 A1 | 5/2015 |
| WO | WO-2015073644 A1 | 5/2015 |

OTHER PUBLICATIONS

Abate-Daga, et al. Oncolytic adenoviruses armed with thymidine kinase can be traced by PET imaging and show potent antitumoural effects by ganciclovir dosing. PLoS One. 2011;6(10):e26142. doi: 10.1371/journal.pone.0026142. Epub Oct. 18, 2011.

Adams. Healing and hurting: molecular mechanisms, functions, and pathologies of cellular senescence. Mol Cell. Oct. 9, 2009;36(1):2-14. doi: 10.1016/j.molcel.2009.09.021. Agarwalla, et al. Oncolytic herpes simplex virus engineering and preparation. Methods Mol Biol. 2012;797:1-19. doi: 10.1007/978-1-61779-340-0_1.

Baker, et al. BubR1 Insufficiency Causes Early Onset of Aging-Associated Phenotypes and Infertility in Mice. Genetics, vol. 36, No. 7, Jul. 2004, pp. 744-749.

Baker, et al. Clearance of p16Ink4a-positive senescent cells delays ageing-associated disorders. Nature 479(7372):232-236 (2011).

Baker, et al. Opposing roles for p16Ink4a and p19Arf in senescence and ageing caused by BubR1 insufficiency. Nat Cell Biol. Jul. 2008;10(7):825-36. doi: 10.1038/ncb1744. Epub May 30, 2008.

Bennett, et al. SP600125, An Anthrapyrazolone Inhibitor of Jun N-Terminal Kinase. PNAS, vol. 98, No. 24, 20, 2001, pp. 13681-13686.

Campisi, et al. Cellular senescence: a link between cancer and age-related degenerative disease? Semin Cancer Biol. Dec. 2011;21(6):354-9. doi: 10.1016/j.semcancer.2011.09.001. Epub Sep. 10, 2011.

Campisi, et al. Cellular senescence: when bad things happen to good cells. Nature Reviews Molecular Cell Biology 8:729-740, 2007.

Campisi, J. Cellular senescence: putting the paradoxes in perspective. Curr Opin Genet Dev. Feb. 2011;21(1):107-12. doi: 10.1016/j.gde.2010.10.005. Epub Nov. 17, 2010.

Campisi, J. Senescent cells, tumor suppression, and organismal aging: good citizens, bad neighbors. Cell. Feb. 25, 2005;120(4):513-22.

Chang, et al. Effects of p21 Wafl/Cipl/Sdilon cellular gene expression: Implications for carcinogenesis, senescence, and age-related diseases. PNAS 97(8):4291-4296, 2000.

Chistiakov. How to fight with senescent cells? Geriatr Gerontol Int. Apr. 2011;11(2):233-5. doi: 10.1111/j.1447-0594.2010.00654.x.

Chung, et al. Molecular inflammation: underpinnings of aging and age-related diseases. Ageing Res Rev. Jan. 2009;8(1):18-30. doi: 10.1016/j.arr.2008.07.002. Epub Jul. 18, 2008.

Cibelli, et al. Cloned transgenic calves produced from nonquiescent fetal fibroblasts. Science, 1998, 280:1256-1258.

Co-pending U.S. Appl. No. 13/975,179, filed Aug. 23, 2013.

Co-pending U.S. Appl. No. 13/975,217, filed Aug. 23, 2013.

Coppe, et al. Senescence-associated secretory phenotypes reveal cell-nonautonomous functions of oncogenic RAS and the p53 tumor suppressor. PLoS Biol. Dec. 2, 2008;6(12):2853-68. doi: 10.1371/journal.pbio.0060301.

Davalos, et al. p53-dependent release of Alarmin HMGB1 is a central mediator of senescent phenotypes. J Cell Biol. May 13, 2013;201(4):613-29. doi: 10.1083/jcb.201206006. Epub May 6, 2013.

Davalos, et al. Senescent cells as a source of inflammatory factors for tumor progression. Cancer Metastasis Rev. Jun. 2010;29(2):273-83. doi: 10.1007/s10555-010-9220-9.

Deursen. Clearance of senescent cells and adult aging phenotypes. Pitts. Jun. 2014. 15 pages.

Deursen, et al. Senescent cells have some nerve! Mayo Clinic. NCI. Mar. 2015. Rochester, MN. 15 pages.

Deursen, et al. Senescent cells shorten health and life span. Mayo Clinic. Berlin. FEBS 2015. 30 pages.

Deursen, et al. Senescent in aging and age-related disease: from mechanism to therapy. Mayo Clinic. ICSA Conference. Jul. 2015. Santiago de Compostela. 40 pages.

Deursen. Senescent Cells as Drivers of Cancer & Aging. Mayo Clinic. NYU Dec. 2014. 55 pages.

Deursen. The role of p16+ (senescent) cells in aging. Erice. Jun. 2015. 17 pages.

Deursen. Understanding Senescence and Chromosomal Instability in Cancer and Aging. Mayo Clinic. Ohio State. Jan. 2015. 49 pages.

Dieffenbach, et al. PCR Primer: A Laboratory Manual, ed. Cold Spring Harbor Laboratory Press, 1995.

(56) References Cited

OTHER PUBLICATIONS

Dimri, et al. A biomarker that identifies senescent human cells in culture and in aging skin in vivo. Proc Natl Acad Sci U S A. Sep. 26, 1995;92(20):9363-7.
Drabek, et al. The expression of bacterial nitroreductase in transgenic mice results in specific cell killing by the prodrug CB1954. Gene Therapy, Feb. 1997, 4(2):93-100.
Efeyan, et al. Induction of p53-dependent senescence by the MDM2 antagonist nutlin-3a in mouse cells of fibroblast origin. Cancer Res. Aug. 1, 2007;67(15):7350-7.
Freund, et al. Inflammatory networks during cellular senescence: causes and consequences. Trends Mol Med. May 2010;16(5):238-46. doi: 10.1016/j.molmed.2010.03.003. Epub May 3, 2010.
Freund, et al. Lamin B1 loss is a senescence-associated biomarker. Mol Biol Cell. Jun. 2012;23(11):2066-75. doi: 10.1091/mbc.E11-10-0884. Epub Apr. 11, 2012.
Gan, et al. PPARy accelerates cellular senescence by inducing p16INK4' expression in human diploid fibroblasts. J. Cell Sci., 2008, 121:2235-2245.
Guatelli, et al. Isothermal, in vitro amplification of nucleic acids by a multienzyme reaction modeled after retroviral replication. Proc. Natl. Acad. Sci. USA, Mar. 1990, 87:1874-1878.
Handschin et al. Skeletal Muscle Fiber-type Switching, Exercise Intolerance, and Myopathy in PGC-1-alpha Muscle-specific Knockout Animals. The Journal of Biological Chemistry 282(41):30014-30021 (2007).
Hartman, et al. Mutant mice with small amounts of BubR1 display accelerated age-related gliosis. Neurobiol. Aging, 2007, 28:921-927.
International Preliminary Report on Patentability dated Aug. 2, 2016 for International PCT Patent Application No. PCT/US2015/013387.
International search report and written opinion dated Apr. 22, 2014 for International PCT Patent Application No. PCT/US2013/072938.
International search report and written opinion dated Apr. 30, 2013 for PCT/US2012/069601.
International search report and written opinion dated May 6, 2015 for PCT/US2015/013376.
International search report and written opinion dated Aug. 13, 2013 for PCT/US2013/035023.
International Search Report and Written Opinion in International Application No. PCT/US2012/043613, dated Nov. 29, 2012, 9 pages.
International Search Report and Written Opinion received for PCT Patent Application No. PCT/US2013/035020, dated Jul. 22, 2013, 11 pages.
Johnson, et al. Somatic activation of the K-ras oncogene causes early onset lung cancer in mice. Nature. Apr. 26, 2001;410(6832):1111-6.
Kaina, B. DNA damage-triggered apoptosis: critical role of DNA repair, double-strand breaks, cell proliferation and signaling. Biochem Pharmacol. Oct. 15, 2003;66(8):1547-54.
Kim, et al. SP600125, an inhibitor of Jnk pathway, reduces viability of relatively resistant cancer cells to doxorubicin. Biochem Biophys Res Commun. Sep. 25, 2009;387(3):450-5. doi: 10.1016/j.bbrc.2009.07.036. Epub Jul. 14, 2009.
Kirkland, et al. Effects of fat depot site on differentiation-dependent gene expression in rat preadipocytes. Int. J. Obes. Relat. Metab. Disord., 1996, 20(Suppl 3):5102-107.
Krishnamurthy et al. Ink4a/Arf expression is a biomarker of aging. J Clin Invest 114:1299-1307 (2004).
Krtolica, et al. Senescent fibroblasts promote epithelial cell growth and tumorigenesis: a link between cancer and aging. Proc Natl Acad Sci U S A. Oct. 9, 2001;98(21):12072-7. Epub Oct. 2, 2001.
Kuilman, et al. The essence of senescence. Genes Develop., 2010, 24:2463-2479.
Laberge, et al. Glucocorticoids suppress selected components of the senescence-associated secretory phenotype. Aging Cell 11(4):569-578, 2012.
Laberge, et al. Mitochondrial DNA damage induces apoptosis in senescent cells. Cell Death Dis. Jul. 18, 2013;4:e727. doi: 10.1038/cddis.2013.199.
Le, et al. Ionizing radiation-induced long-term expression of senescence markers in mice is independent of p53 and immune status. Aging Cell. Jun. 2010;9(3):398-409. doi: 10.1111/j.1474-9726.2010.00567.x. Epub Mar. 13, 2010.
LeBrasseur, et al. Myostatin inhibition enhances the effects of exercise on performance and metabolic outcomes in aged mice. J. Gerontol. A. Biol. Sci. Med. Sci., 2009, 64:940-948.
Lessene; et al. Structure-guided design of a selective BCL-X(L) inhibitor. Jun. 2013, 9(6), 390-7.
Lewis. PCR's Competitors are alive and well and moving rapidly towards commercialization. Genetic Engineering News, 1992, 12:1, 2 pages.
Lo. Transformation by iontophoretic microinjection of DNA: multiple integrations without tandem insertions. Mol. Cell. Biol., 1983, 3:1803-1814.
Mallet, et al. Conditional cell ablation by tight control of caspase-3 dimerization in transgenic mice. Nat Biotechnol. Dec. 2002;20(12):1234-9. Epub Nov. 18, 2002.
Matsumoto, et al. Aging-associated vascular phenotype in mutant mice with low levels of BubR1. Stroke, 2007, 38:1050-1056.
Moody, et al. Conditional activation of Neu in the mammary epithelium of transgenic mice results in reversible pulmonary metastasis. Cancer Cell. Dec. 2002;2(6):451-61.
Nasu, et al. Suicide gene therapy for urogenital cancer: current outcome and prospects. Mol Urol. 2000 Summer;4(2):67-71.
Office Action dated Jan. 3, 2017 for U.S. Appl. No. 14/792,208.
Office action dated Jan. 9, 2015 for U.S. Appl. No. 12/809,952.
Office action dated Apr. 7, 2015 for U.S. Appl. No. 14/125,841.
Office action dated May 30, 2014 for U.S. Appl. No. 12/809,952.
Office Action dated Aug. 9, 2017 for U.S. Appl. No. 14/792,208.
Office Action dated Aug. 9, 2017 for U.S. Appl. No. 15/067,543.
Office action dated Aug. 13, 2015 for U.S. Appl. No. 14/792,208.
Office action dated Sep. 11, 2015 for U.S. Appl. No. 13/975,179.
Office action dated Sep. 25, 2015 for U.S. Appl. No. 13/975,217.
Office Action dated Nov. 3, 2016 for U.S. Appl. No. 15/067,543.
Office action dated Nov. 25, 2014 for U.S. Appl. No. 13/830,790.
Pajvani, et al. Fat apoptosis through targeted activation of caspase 8: a new mouse model of inducible and reversible lipoatrophy. Nat Med. Jul. 2005;11(7):797-803. Epub Jun. 19, 2005.
Prieur, et al. Cellular senescence in vivo: a barrier to tumorigenesis. Curr Opin Cell Biol. Apr. 2008;20(2):150-5. doi: 10.1016/j.ceb.2008.01.007. Epub Mar. 18, 2008.
Rodier, et al. Persistent DNA damage signalling triggers senescence-associated inflammatory cytokine secretion. Nat Cell Biol. Aug. 2009;11(8):973-9. doi: 10.1038/ncb1909. Epub Jul. 13, 2009.
Roninson. Tumor Cell Senescence in Cancer Treatment. Cancer Research 63(11):2705-2715, 2003.
Sambrook, et al. Molecular Cloning, A Laboratory Manual, second edition, Cold Spring Harbor Press, Plainview; NY. 1989.
Schmitt, et al. A senescence program controlled by p53 and p16INK4a contributes to the outcome of cancer therapy. Cell. May 3, 2002;109(3):335-46.
Shangary, et al. Temporal activation of p53 by a specific MDM2 inhibitor is selectively toxic to tumors and leads to complete tumor growth inhibition. Proc Natl Acad Sci U S A. Mar. 11, 2008;105(10):3933-8. doi: 10.1073/pnas.0708917105. Epub Mar. 3, 2008.
Sharpless, et al. Telomeres, stem cells, senescence, and cancer. Journal of Clinical Investigation 113(2):160-168, 2004.
Sis, et al. Accelerated expression of senescence associated cell cycle inhibitor p16INK4A in kidneys with glomerular disease. Kidney Int. Feb. 2007;71(3):218-26. Epub Dec. 20, 2006.
Soleimani, et al. A protocol for isolation and culture of mesenchymal stem cells from mouse bone marrow. Nat Protoc 4:102-106 (2009).
Stanley et al. Senescence and the Healing Rates of Venous Ulcers. J Vasc Surg. Jun. 2001;33(6):1206-11.
Tchkonia, et al. Fat tissue, aging, and cellular senescence. Aging Cell. Oct. 2010;9(5):667-84.
Te Poele, et al. DNA damage is able to induce senescence in tumor cells in vitro and in vivo. Cancer Res. Mar. 15, 2002;62(6):1876-83.

(56) References Cited

OTHER PUBLICATIONS

Thompson, et al. Germ line transmission and expression of a corrected HPRT gene produced by gene targeting in embryonic stem cells. Cell, 1989, 56:313-321.
Tsuji, et al. Alveolar cell senescence exacerbates pulmonary inflammation in patients with chronic obstructive pulmonary disease. Respiration. 2010;80(1):59-70. doi: 10.1159/000268287. Epub Dec. 17, 2009.
Van Der Putten, et al. Efficient insertion of genes into the mouse germ line via retroviral vectors. Proc. Natl. Acad. Sci. USA, 1985, 82:6148-1652.
Wakayama, et al. Full-term development of mice from enucleated oocytes injected with cumulus cell nuclei. Nature, 1988, 394:369-374.
Wang, et al. Characterization of regulatory elements on the promoter region of p16(INK4a) that contribute to overexpression of p16 in senescent fibroblasts. J Biol Chem. Dec. 28, 2001;276(52):48655-61. Epub Oct. 11, 2001.
Wang, et al. PANIC-ATTAC: a mouse model for inducible and reversible beta-cell ablation. Diabetes, Aug. 2008, 57(8):2137-48.
Weiss. Hot prospect for new gene amplifier. Science, 1991, 254:1292-1293.
Wilmut, et al. Viable offspring derived from fetal and adult mammalian cells. Nature, 1997, 385:810-813.
Zhao, et al. Small molecule inhibitors of MDM2-p53 and MDMX-p53 interactions as new cancer therapeutics. BioDiscovery, 8. 2013; 8(4).15 pages.
U.S. Appl. No. 16/008,974 Office Action dated Sep. 20, 2019.
He, W. et al. Plasminogen Activator Inhibitor-1 Is a Transcriptional Target of the Canonical Pathway of Wnt/β-Catenin Signaling. The Journal of Biological Chemistry vol. 285, No. 32, pp. 24665-24675, Aug. 6, 2010.
Lewis, John. et al. Images presented in Montreal, Canada at the International Cell Senescence Association Conference, Jul. 8-11, 2018, entitled: "Selective Ablation of Senescent and Malignant Cells Using Apoptotic Gene Therapy." (pp. 1-28).
Macleod, et al. p53-dependent and independent expression of p21 during cell growth, differentiation, and DNA damage. Genes Dev. Apr. 15, 1995;9(8):935-44.
Ray, et al. Imaging tri-fusion multimodality reporter gene expression in living subjects. Cancer Res. Feb. 15, 2004;64(4):1323-30.
U.S. Appl. No. 14/394,854 Advisory Office Action dated Aug. 15, 2018.
U.S. Appl. No. 14/394,854 Final Office Action dated Jan. 26, 2018.
U.S. Appl. No. 15/943,356 Non-Final Office Action dated Jun. 14, 2018.
U.S. Appl. No. 15/943,356 Notice of Allowance dated Jan. 14, 2019.
U.S. Appl. No. 16/008,974 Final Office Action dated Mar. 22, 2019.
U.S. Appl. No. 16/008,974 Non-Final Office Action dated Sep. 7, 2018.
U.S. Appl. No. 16/029,244 Notice of Allowance dated May 24, 2019.
Yao et al. A Novel Tetracycline-Inducible Viral Replication Switch. Human Gene Therapy 10:419-427 (Feb. 10, 1999).
Ambroggio, et al. Design of protein conformational switches, Current Opinion Structural Biology, 16(4):525-530 (Aug. 2006).
Baker, et al. Naturally occurring p16(Ink4a)-positive cells shorten healthy lifespan. Nature. Feb. 11, 2016;530(7589):184-9.
Bazarov, A.V. et al. P16INK4a Mediated Suppression of Telomerase in Normal and Malignant Human Breast Cells. Aging Cell 9(5):736-746 (Oct. 2010).
Beausejour, C.M. et al. Reversal of human cellular senescence: roles of the p53 and p16 pathways, EMBO J. Aug. 15, 2003;22(16):4212-22.
Binkowski, et al. Ligand-Regulated Peptides: A General Approach for Modulating Protein-Peptide Interactions with Small Molecules, 12(7):847-855 (Jul. 2005).
Braun, et al. Cellular senescence limits regenerative capacity and allograft survival. J Am Soc Nephrol. Sep. 2012;23(9):1467-73. Epub Jul. 12, 2012.
Buskirk, et al. Creating Small-Molecule-Dependent Switches to Modulate Biological Functions, Cell Chemical Biology, 12(2):151-161 (Feb. 2005).
Coppe, JP et al. Tumor Suppressor and Aging Biomarker p16 INK4a Induces Cellular Senescence without the Associated Inflammatory Secretory Phenotype, J. Biol. Chem. 286(42):36396-403 (Oct. 21, 2011) Epub Aug. 31, 2011.
Demaria, M. et al. An Essential Role for Senescent Cells in Optimal Wound Healing through Secretion of PDGF-AA, Dev. Cell, 31(16):722-733 (Dec. 22, 2014).
Fegan, A. et al. Chemically Controlled Protein Assembly: Techniques and Applications, Chemical Reviews, 110(6):3315-3336 (2010).
Gorenne, et al. Vascular smooth muscle cell senescence in atherosclerosis. Cardiovasc Res. Oct. 1, 2006;72(1):9-17. Epub Jun. 6, 2006.
Gross, A. et al. Enforced dimerization of BAX results in its translocation, mitochondrial dysfunction and apoptosis. EMBO J. 17(14):3878-3885 (Jul. 15, 1998).
International search report and written opinion dated Jul. 11, 2013 for PCT/US2013/036811.
Jia, et al. Cancer gene therapy targeting cellular apoptosis machinery. Cancer Treat Rev. Nov. 2012;38(7):868-76. Epub Jul. 15, 2012.
Kassem, et al. Senescence-associated intrinsic mechanisms of osteoblast dysfunctions. Aging Cell. Apr. 2011; 10(2):191-7. Epub Feb. 18, 2011.
Liu, et al. Dimerization of two novel apoptosis inducing proteins and its function in regulating cell apoptosis. Sci. China C. Life Sci. 46(3):225-234 (Jun. 2003).
Martin, et al. Aging, articular cartilage chondrocyte senescence and osteoarthritis. Biogerontology. 2002;3(5):257-64.
Martin, et al. The Role of Chondrocyte Senescence in the Pathogenesis of Osteoarthritis and in Limiting Cartilage Repair. J Bone Joint Surg Am, vol. 85, Suppl 2, Apr. 2003, pp. 106-110.
Minamino et al., Vascular Cell Senescence: Contribution to Atherosclerosis. Journal of the American Heart Association, Circ Res. Jan. 5, 2007;100(1):15-26.
Myohanen; et al. Sequence-specific DNA binding activity of RNA helicase a to the p16INK4a promoter. J. Biol. Chem. Jan. 12, 2001, 276(2), 1634-42.
Naylor; et al. Senescent cells: a novel therapeutic target for aging and age-related diseases. Clin. Pharmacol. Ther. Jan. 2013; 93(1):105-16. Epub Dec. 5, 2012.
Office Action dated Jun. 6, 2016 for U.S. Appl. No. 14/792,208.
Office Communication dated Jul. 31, 2017 for U.S. Appl. No. 14/394,854.
Roberts, et al. Senescence in human intervertebral discs. Eur Spine J. Aug. 2006;15 Suppl 3:S312-6. Epub Jun. 14, 2006.
Robl, et al. Transgenic animal production and animal biotechnology. Theriogenology. Jan. 1, 2007;67(1):127-33.
Strasser, et al. Apoptosis signaling. Annu Rev Biochem. 2000;69:217-45.
U.S. Appl. No. 14/792,208 Notice of Allowance dated Oct. 6, 2017.
U.S. Appl. No. 15/080,991 Notice of Allowance dated Oct. 10, 2018.
International Application No. PCT/US2012/043613 International Preliminary Report Patentability dated Jan. 9, 2014, pp. 1-12.
U.S. Appl. No. 15/067,543 Notice of Allowance dated Oct. 13, 2017.

* cited by examiner

Entire 9267 nt sequence, uninterrupted
ctaaattgtaagcgttaatattttgttaaaattcgcgttaaattttgttaaatcagctcattt
tttaaccaataggccgaaatcggcaaaatcccttataaatcaaaagaatagaccgagatagggt
tgagtgttgttccagtttggaacaagagtccactattaaagaacgtggactccaacgtcaaagg
gcgaaaaaccgtctatcagggcgatggcccactacgtgaaccatcacccaatcaagttttttg
gggtcgaggtgccgtaaaagcactaaatcggaaccctaaagggagcccccgatttagagcttgac
ggggaaagccggcgaacgtggcgagaaaggaagggaagaaagcgaaaggagcgggcgctagggc
gctggcaagtgtagcggtcacgctgcgcgtaaccaccacaccgccgcgcttaatgcgccgcta
cagggcgcgtcccattcgccattcaggctgcgcaactgttgggaagggcgatcggtgcgggcct
cttcgctattacgccagctggcgaaaggcgggatgtgctgcaaggcgattaagttgggtaacgcc
aggggttttcccagtcacgacgttgtaaaacgacggccagtgagcgcgcgtaatacgactcacta
tagggcgaattggagctccaccgcggtggcggccgctctagaactagtgGATCCGTGTAAAGTC
ACTGCTTTTATAGCTACATCTGCATAGATCCCTGTATGAAAGCATGTACTACCTGGATAATAA
TATCTGTATTTTTCTGTAGTAGGAAATCAGTGTAGTTTTTAAAACCAAAAAGTATTGTTATTAA
TCTATCTTTGATCTCAAACAATTTCAATGACCTAGTATAGTGATTTCTACGGAAAGCCCTGCAA
TTTACTCAAAGCAGTTTTAAATATTGTTTTAAAAGTGTGTGTGTGTGTGTGTGTGTGTGTGTG
TGTGTGTGGTGTTAAAGTCATTTTCAAACCCCTCACAATGTCTTGAATGTGACATTTGAGTC
ATTTATGGTAACTTATAACTCCTTTGAAGAAGTTATTCAGAATTGAGGTTCCAGACACACAAAT
GCACAATACACCATTTTTCCTTCCAGTTAACAATCAGAGGGCAACACTTATTTTTAAAGGAAAA
TCGACTCCATAAGGGACTTTATAAAGGGGTAGACATAAACCAGTATCAGGGATAAACTCTCCGT
TCCCCTGTTTAACCTAATTTTCCCAGGGCCATCCTGGAATACGAATTTTCTCTTGAAATACAGT
CAAAGAAAAGTGGTAGGCTACAGAGCAGAGGAAACACTGGACACAGCGACCCACCCCAGAGT
CACTTCCCTTAATCTAATGACTAGGTTTTTTCTGAAAGTTATTTGTTAGAACACAGGAACTTTT
GCGACCACAGTGATGCTTTTAGAGGGTTGAATCCTCAAAAAGAAAATTAATCGCAACTAGTAGA
AGGGAGATTACTTATTGATTCTTATAACTTCTGCAGGAATACACAGTTATGAGTTAGGGCAAAG
AGAAAATTGACTTTTAATATTCTCTATCACTAACATGAGAGAACATGTATGTGTTCCAAAATAA
TTTTTATTTATTGAAAACCCGCTATATACCTGGATTTTCACAGAATATTCATTACTCTCCAAAA
TGGCCTTTTCTAGGTGAATTTTATTTTCCTTACAGACCTCAAGAAGTTTACATAATTTACTTAA
ACCTGAGGAGAGAGAACAAAGCCTCAGAAAATTTACATAGTTTATTTAAACTAAACTCAGCTTG
CTTGGTAGCAGCTTCTAATCCCAGCAGTTAAAGAGACAGAAGCAGGGCCAACCTGGGGTATAAT
ATAAGGTGAGACTCTCCTTTCTTTCTCTCTGTCTCTGTCTGTCTCTGTCTCTGTGTGTGTGT
GTGTGTGTGTGTGTGTGTGTCTCCTCTCTCTCTCTCTCTCTCTCTCTCTCTCTCTCTCTCTG
TCTCTCTCTCCCTCCCCTCCCTCCCTCTCCCCCTCCTCTCTCCCTCCCTCTCCCTCCCCCCC
CCCACACATTTGAATTCGTGGAGTTGGTAAATGAGGGGTCAGTTCTCTGTCTGTCTGTAGTTTT
GTGTCCACAGGATATGACTGACATTCTCACCACACACATACAAAGTCAAAAATAGCTGTGGCCA
TATAAAGAATATGGGGAGAGAAAATTATTCAAAATCTGCAGAAAATAATGCCAGGCCTTTAATC
CTGGCACCCAGGAGGCAGAAGGGAGACAGAGTTCTGAGTTTATGCTGAGTTCCAGGAGTGGAAG
AAAGGGCCATTGCCTTTCTGGTGAGGACTGTCTTTTTAAATCCTCCCTTCTGTCCAGTACTGGT
AACTCTGCCCAAAGCGTGTTCTTCTTCCTGCCTCACAAGATTGCAAAGACGTTTTAACGAACA
ATTTAAACCGGTGCAACGTTTATGCGCAGCACACCAACTCATTTAAACAAACAACAGCCCATA
AAATAGAAATACTTTATAAGCAGATTGCCCTCCGATGACTTCACCCCGTCACTTTTTTATAGTT
GTGTACAGAATCCTAGCACTGATACAGCAACATCAGAAATGTTTCTGCAAATCCTTCGCAAAGA
TTCGGATTTCATACTGGGCGTGGTACCCTCCAAAATGAGTTGTTTGAGCTAGGGTTGTTGGGAT
CTCAGCTTGGCGAAGTTGTAGCTCTTTCTTCTGAATAAAAGATGACACAATTTTCTGCTAAGAT

*Fig. 1A*

GTTAAATACCTTAAGTTTCAGTGTAGTGATGAAAATTACCCTCCTTCGTTTTTCTAATACCTGG
GTGTTGCACTGGGGAGGAAGGAGAGATTTCGAGAAGGACTAGTTCACTTTCTCAGAAGACACGT
GTGCACTTCTTTGCTGTGCGGGTCCAGAAGGAGCCCAGCGTGTCAAAGGGTGACCAGGCATGGG
GGAGGGGTGTTAGCGTGGGTAGCAGGCGGGGGCTGTCCGATCCTTTAGCGCTGTTTCAACGCCC
AGCTCTCCTCCTGAACCCTGCATCTCTTCTGTAGTCCGGGCTCCATCCCTTTCCCCTCCCCAT
CCGGAGGTGGGGGGAACAGCAGTGTTTTCAGGGGTGTTCAATTCATGCTATATTCAGGGCAAAT
AGCGCCACCTATGGCGGGCTGTGGAGCCAGGTCAGGAGCAGAGTGTGGCTCCCCCCCCCCCCA
CACCATCCTCAGAGGAAGGAAGGAGGGACCCACTGGTCACACGACTGGGCGATTGGGCGGGCAC
TGAATCTCCGCGAGGAAAGCGAACTCGAGGAGAGCCATCACGCGTAGCatggggagtagcaaga
gcaagcctaaggaccccagccagcgctctagaggcgtccaagtcgaaaccattagtcccggcga
tggcagaacatttcctaaaaggggacaaacatgtgtcgtccattatacaggcatgttggaggac
ggcaaaaaggtggacagtagtagagatcgcaataaaccttcaaatcatgttgggaaaacaag
aagtcattaggggatgggaggagggcgtggctcaaatgtccgtcggccaacgcgctaagctcac
catcagccccgactacgcatacggcgctaccgacatcccggaattattcccctcacgctacc
ttggtgtttgacgtcgaactgttgaagctcgagactagaggagtgcaggtggagactatctccc
caggagacgggcgcaccttcccaagcgcggccagacctgcgtggtgcactacaccgggatgct
tgaagatggaaagaaagttgattcctccgggacagaaacaagcccttttaagtttatgctaggc
aagcaggaggtgatccgaggctgggaagaagggggttgcccagatgagtgtgggtcagagagcca
aactgactatatctccagattatgctatggtgccactgggcacccaggcatcatccaccaca
tgccactctcgtcttcgatgtggagcttctaaaactggaaactagtagtgaatcacagactttg
gacaaagtttaccaaatgaaaagcaaacctcgggggatactgtctgatcatcaacaatcacaatt
ttgcaaaagcacgggagaaagtgcccaaacttcacagcattagggacaggaatggaacacactt
ggatgcaggggctttgaccacgacctttgaagagcttcattttgagatcaagccccacgatgac
tgcacagtagagcaaatctatgagattttgaaaatctaccaactcatggaccacagtaacatgg
actgcttcatctgctgtatcctctcccatggagacaagggcatcatctatggcactgatggaca
ggaggccccccatctatgagctgacatctcagttcactggtttgaagtgcccttccccttgctgga
aaacccaaagtgttttttattcaggcttgtcaggggggataactaccagaaaggtatacctgttg
agactgattcagaggagcaaccctatttagaaatggattatcatcacctcaaacgagatatat
cccggatgaggctgactttctgctggggatggccactgtgaataactgtgtttcctaccgaaac
cctgcagagggaacctggtacatccagtcactttgccagagcctgagagagcgatgtcctcgag
gcgatgatattctcaccatcctgactgaagtgaactatgaagtaagcaacaaggatgacaagaa
aaacatggggaaacagatgcctcagcctactttcacactaagaaaaaaacttgtcttcccttct
gatgattacaaggatgacgacgataagtgaggatcaacctcgaggaattcACGCGTTTAATTAA
CTCGAGGTTTTCGAGGTCGACGGTATCGATAAGCTTGATATCGAATTCCGCCCCTCTCCCTCCC
CCCCCCCTAACGTTACTGGCCGAAGCCGCTTGGAATAAGGCCGGTGTGCGTTTGTCTATATGTT
ATTTTCCACCATATTGCCGTCTTTTGGCAATGTGAGGGCCCGGAAACCTGGCCCTGTCTTCTTG
ACGAGCATTCCTAGGGGTCTTTCCCCTCTCGCCAAAGGAATGCAAGGTCTGTTGAATGTCGTGA
AGGAAGCAGTTCCTCTGGAAGCTTCTTGAAGACAAACAACGTCTGTAGCGACCCTTTGCAGGCA
GCGGAACCCCCCACCTGGCGACAGGTGCCTCTGCGGCCAAAAGCCACGTGTATAAGATACACCT
GCAAAGGCGGCACAACCCCAGTGCCACGTTGTGAGTTGGATAGTTGTGGAAAGAGTCAAATGGC
TCTCCTCAAGCGTATTCAACAAGGGGCTGAAGGATGCCCAGAAGGTACCCCATTGTATGGGATC
TGATCTGGGGCCTCGGTGCACATGCTTTACATGTGTTTAGTCGAGGTTAAAAAAACGTCTAGGC

*Fig. 1B*

CCCCCGAACCACGGGGACGTGGTTTTCCTTTGAAAAACACGATGATAATATGGCCACAACCATG
GTGAGCAAGGGCGAGGAGCTGTTCACCGGGGTGGTGCCCATCCTGGTCGAGCTGGACGGCGACG
TAAACGGCCACAAGTTCAGCGTGTCCGGCGAGGGCGAGGGCGATGCCACCTACGGCAAGCTGAC
CCTGAAGTTCATCTGCACCACCGGCAAGCTGCCCGTGCCCTGGCCCACCCTCGTGACCACCCTG
ACCTACGGCGTGCAGTGCTTCAGCCGCTACCCCGACCACATGAAGCAGCACGACTTCTTCAAGT
CCGCCATGCCCGAAGGCTACGTCCAGGAGCGCACCATCTTCTTCAAGGACGACGGCAACTACAA
GACCCGCGCCGAGGTGAAGTTCGAGGGCGACACCCTGGTGAACCGCATCGAGCTGAAGGGCATC
GACTTCAAGGAGGACGGCAACATCCTGGGGCACAAGCTGGAGTACAACTACAACAGCCACAACG
TCTATATCATGGCCGACAAGCAGAAGAACGGCATCAAGGTGAACTTCAAGATCCGCCACAACAT
CGAGGACGGCAGCGTGCAGCTCGCCGACCACTACCAGCAGAACACCCCCATCGGCGACGGCCCC
GTGCTGCTGCCCGACAACCACTACCTGAGCACCCAGTCCGCCCTGAGCAAAGACCCCAACGAGA
AGCGCGATCACATGGTCCTGCTGGAGTTCGTGACCGCCGCCGGGATCACTCTCGGCATGGACGA
GCTGTACAAGTAAAGCGGCCGCGATCTTTTCCCTCTGCCAAAAATTATGGGGACATCATGAAG
CCCCTTGAGCATCTGACTTCTGGCTAATAAAGGAAATTTATTTTCATTGCAATAGTGTGTTGGA
ATTTTTTGTGTCTCTCACTCGGAAGGACATATGGGAGGGCAAATCATTTAAAACATCAGAATGA
GTATTTGGTTTAGAGTTTGGCAACATATGCCATATGCTGGCTGCCATGAACAAAGGTGGCTATA
AAGAGGTCATCAGTATATGAAACAGCCCCCTGCTGTCCATTCCTTATTCCATAGAAAGCCTTG
ACTTGAGGTTAGATTTTTTTTATATTTTGTTTTGTGTTATTTTTTTCTTTAACATCCCTAAAAT
TTTCCTTACATGTTTTACTAGCCAGATTTTCCTCCTCTCCTGACTACTCCCAGTCATAGCTGT
CCCTCTTCTCTTATGAAGATCCCTCGACCTGCAGCCCAAGCTTGGCGTAATCATGGTCATAGCT
GTTTCCTGTGTGAAATTGTTATCCGCTCACAATTCCACACAACATACGAGCCGGAAGCATAAAG
TGTAAAGCCTGGGGTGCCTAATGAGTGAGCTAACTCACATTAATTGCGTTGCGCTCACTGCCCG
CTTTCCAGTCGGGAAACCTGTCGTGCCAGCGGATCCGCATCTCAATTAGTCAGCAACCATAGTC
CCGCCCCTAACTCCGCCCATCCCGCCCCTAACTCCGCCCAGTTCCGCCCATTCTCCGCCCCATG
GCTGACTAATTTTTTTATTTATGCAGAGGCCGAGGCCGCCTAAACGGCCGGCCATcgataccg
tcgacctcgagggggggcccggtacccagcttttgttccctttagtgagggttaattgcgcgct
tggcgtaatcatggtcatagctgtttcctgtgtgaaattgttatccgctcacaattccacacaa
catacgagccggaagcataaagtgtaaagcctggggtgcctaatgagtgagctaactcacatta
attgcgttgcgctcactgcccgctttccagtcgggaaacctgtcgtgccagctgcattaatgaa
tcggccaacgcgcggggagaggcggtttgcgtattgggcgctcttccgcttcctcgctcactga
ctcgctgcgctcggtcgttcggctgcggcgagcggtatcagctcactcaaaggcggtaatacgg
ttatccacagaatcaggggataacgcaggaaagaacatgtgagcaaaaggccagcaaaaggcca
ggaaccgtaaaaaggccgcgttgctggcgtttttccataggctccgcccccctgacgagcatca
caaaaatcgacgctcaagtcagaggtggcgaaacccgacaggactataaagataccaggcgttt
ccccctggaagctccctcgtgcgctctcctgttccgaccctgccgcttaccggatacctgtccg
cctttctcccttcgggaagcgtggcgctttctcatagctcacgctgtaggtatctcagttcggt
gtaggtcgttcgctccaagctgggctgtgtgcacgaaccccccgttcagcccgaccgctgcgcc
ttatccggtaactatcgtcttgagtccaacccggtaagacacgacttatcgccactggcagcag
ccactggtaacaggattagcagagcgaggtatgtaggcggtgctacagagttcttgaagtggtg
gcctaactacggctacactagaaggacagtatttggtatctgcgctctgctgaagccagttacc
ttcggaaaaagagttggtagctcttgatccggcaaacaaaccaccgctggtagcggtggttttt
ttgtttgcaagcagcagattacgcgcagaaaaaaaggatctcaagaagatcctttgatcttttc
```

*Fig. 1C* tacggggtctgacgctcagtggaacgaaaactcacgttaagggatttggtcatgagattatca
aaaaggatcttcacctagatccttttaaattaaaaatgaagttttaaatcaatctaaagtatat
atgagtaaacttggtctgacagttaccaatgcttaatcagtgaggcacctatctcagcgatctg
tctatttcgttcatccatagttgcctgactccccgtcgtgtagataactacgatacgggagggc
ttaccatctggccccagtgctgcaatgataccgcgagacccacgctcaccggctccagatttat
cagcaataaaccagccagccggaaggggccgagcgcagaagtggtcctgcaactttatccgcctc
catccagtctattaattgttgccgggaagctagagtaagtagttcgccagttaatagtttgcgc
aacgttgttgccattgctacaggcatcgtggtgtcacgctcgtcgtttggtatggcttcattca
gctccggttcccaacgatcaaggcgagttacatgatccccatgttgtgcaaaaaagcggttag
ctccttcggtcctccgatcgttgtcagaagtaagttggccgcagtgttatcactcatggttatg
gcagcactgcataattctcttactgtcatgccatccgtaagatgcttttctgtgactggtgagt
actcaaccaagtcattctgagaatagtgtatgcggcgaccgagttgctcttgcccggcgtcaat
acgggataataccgcgccacatagcagaactttaaaagtgctcatcattggaaaacgttcttcg
gggcgaaaactctcaaggatcttaccgctgttgagatccagttcgatgtaacccactcgtgcac
ccaactgatcttcagcatcttttactttcaccagcgtttctgggtgagcaaaaacaggaaggca
aaatgccgcaaaaaagggaataagggcgacacggaaatgttgaatactcatactcttccttttt
caatattattgaagcatttatcagggttattgtctcatgagcggatacatatttgaatgtattt
agaaaaataaacaaataggggttccgcgcacatttccccgaaaagtgccac (SEQ ID NO:1)

Fig. 1D ctaaattgtaagcgttaatatttgttaaaattcgcgttaaattttgttaaatcagctcattt
tttaaccaataggccgaaatcggcaaaatcccttataaatcaaaagaatagaccgagatagggt
tgagtg (SEQ ID NO:2)

F1 ori:
ttgttccagtttggaacaagagtccactattaaagaacgtggactccaacgtcaaagggcgaaa
aaccgtctatcagggcgatggcccactacgtgaaccatcaccctaatcaagttttttggggtcg
aggtgccgtaaagcactaaatcggaaccctaaagggagcccccgatttagagcttgacggggaa
agccggcgaacgtggcgagaaaggaagggaagaaagcgaaaggagcgggcgctagggcgctggc
aagtgtagcggtcacgctgcgcgtaaccaccacacccgccgcgcttaatgcgccgctacagggc
gcgtc (SEQ ID NO:3)

LacZ alpha:
ccattcgccattcaggctgcgcaactgttgggaagggcgatcggtgcgggcctcttcgctatta
cgccagctggcgaaagggggatgtgctgcaaggcgattaagttgggtaacgccagggttttccc
agtcacgacgt (SEQ ID NO:4)

M13 fwd:
tgtaaaacgacggccagtgagcgcgc (SEQ ID NO:5)

T7:
gtaatacgactcactatagggcgaattggagctccaccgcggtggcggccgctctagaactagtg (SEQ ID NO:6)

BAMH1, p16 promoter:
GATCC (SEQ ID NO:7)

forprimer3, p16 promoter:
GTGTAAAGTCACT (SEQ ID NO:8)

*Fig. 2A* p16 promoter:
CTTTTATAGCTACATCTGCATAGATCCCCTGTATGAAAGCATGTACTACCTGGATAATAATATC
TGTATTTTTCTGTAGTAGGAAATCAGTGTAGTTTTTAAAACCAAAAAGTATTGTTATTAATCTA
TCTTTGATCTCAAACAATTTCAATGACCTAGTATAGTGATTTCTACGGAAAGCCCTGCAATTTA
CTCAAAGCAGTTTTTAAATATTGTTTTAAAAGTGTGTGTGTGTGTGTGTGTGTGTGTGTGTGTG
TGTGTGGTGTTAAAGTCATTTTCAAACCCCTCACAATGTCTTGAATGTGACATTTGAGTCATTT
ATGGTAACTTATAACTCCTTTGAAGAAGTTATTCAGAATTGAGGTTCCAGACACACAAATGCAC
AATACACCATTTTTCCTTCCAGTTAACAATCAGAGGGCAACACTTATTTTAAAGGAAAATCGA
CTCCATAAGGGACTTTATAAAGGGGTAGACATAAACCAGTATCAGGGATAAACTCTCCGTTCCC
CTGTTTAACCTAATTTTCCCAGGGCCATCCTGGAATACGAATTTTCTCTTGAAATACAGTCAAA
GAAAAGTGGTAGGCTACAGAGCAGAGGAAACACTGGACACAGCGACCCACCCCAGAGTCACTT
CCCTTAATCTAATGACTAGGTTTTTTCTGAAAGTTATTTTGTTAGAACACAGGAACTTTTGCGA
CCACAGTGATGCTTTTAGAGGGTTGAATCCTCAAAAAGAAAATTAATCGCAACTAGTAGAAGGG
AGATTACTTATTGATTCTTATAACTTCTGCAGGAATACACAGTTATGAGTTAGGGCAAAGAGAA
AATTGACTTTTAATATTCTCTATCACTAACATGAGAGAACATGTATGTGTTCCAAAATAATTTT
TATTTATTGAAAACCCGCTATATACCTGGATTTTCACAGAATATTCATTACTCCAAAATGGC
CTTTTCTAGGTGAATTTTATTTTCCTTACAGACCTCAAGAAGTTTACATAATTTACTTAAACCT
GAGGAGAGAGAACAAAGCCTCAGAAAATTTACATAGTTTATTTAAACTAAACTCAGCTTGCTTG
GTAGCAGCTTCTAATCCCAGCAGTTAAAGAGACAGAAGCAGGGCCAACCTGGGGTATAATATAA
GGTGAGACTCTCCTTTCTTTCTCTCTGTCTCTGTCTGTCTCTGTCTCTGTGTGTGTGTGTGT
GTGTGTGTGTGTGTGTGTCTCCTCTCTCTCTCTCTCTCTCTCTCTCTCTCTCTCTCTGTCTC
TCTCTCCCTCCCCCTCCCTCCCTCTCCCCCTCCTCTCTCCCTCCCTCTCCCTCCCCCCCCCCA
CACATTTGAATTCGTGGAGTTGGTAAATGAGGGGTCAGTTCTCTGTCTGTCTGTAGTTTTGTGT
CCACAGGATATGACTGACATTCTCACCACACACATACAAAGTCAAAAATAGCTGTGGCCATATA
AAGAATATGGGGAGAGAAAATTATTCAAAATCTGCAGAAAATAATGCCAGGCCTTTAATCCTGG
CACCCAGGAGGCAGAAGGGAGACAGAGTTCTGAGTTTATGCTGAGTTCCAGGAGTGGAAGAAAG
GGCCATTGCCTTTCTGGTGAGGACTGTCTTTTTAAATCCTCCCTTCTGTCCAGTACTGGTAACT
CTGCCCAAAGCGTGTTCTTCTTCCTGCCTCACAAGATTGCAAAGACGTTTTTAACGAACAATTT
AAACCGGTGCAACGTTTATGCGCAGCACACCAACTCATTTAAACAAACAACAGCCCCATAAAAT
AGAAATACTTTATAAGCAGATTGCCCTCCGATGACTTCACCCCGTCACTTTTTTATAGTTGTGT
ACAGAATCCTAGCACTGATACAGCAACATCAGAAATGTTTCTGCAAATCCTTCGCAAAGATTCG
GATTTCATACTGGGCGTGGTACCCTCCAAAATGAGTTGTTTGAGCTAGGGTTGTTGGGATCTCA
GCTTGGCGAAGTTGTAGCTCTTTCTTCTGAATAAAAGATGACACAATTTTCTGCTAAGATGTTA
AATACCTTAAGTTTCAGTGTAGTGATGAAAATTACCCTCCTTCGTTTTTCTAATACCTGGGTGT
TGCACTGGGGAGGAAGGAGAGATTTCGAGAAGGACTAGTTCACTTTCTCAGAAGACACGTGTGC
ACTTCTTTGCTGTGCGGGTCCAGAAGGAGCCCAGCGTGTCAAAGGGTGACCAGGCATGGGGGAG
GGGTGTTAGCGTGGGTAGCAGGCGGGGCTGTCCGATCCTTTAGCGCTGTTTCAACGCCCAGCT
CTCCTCCTGAACCCTGCATCTCTTCTGTAGTCCGGGCTCCATCCCTTTCCCCTCCCCCATCCGG
AGGTGGGGGAACAGCAGTGTTTTCAGGGGTGTTCAATTCATGCTATATTCAGGGCAAATAGCG
CCACCTATGGCGGGCTGTGGAGCCAGGTCAGGAGCAGAGTGTGGCTCCCCCCCCCCCCCACACC
ATCCTCAGAGGAAGGAAGGAGGGACCCACTGGTCACACGACTGGGCGATTGGGCGGGCACTGAA
TCTCCGCGAGGAAAGCGAACTCGAGGAGAGCCATCACGCGTAGC (SEQ ID NO:9)

*Fig. 2B*

FKBP:
atggggagtagcaagagcaagcctaaggaccccagccagcgctctagaggcgtccaagtcgaaa
ccattagtcccggcgatggcagaacattcctaaaaggggacaaacatgtgtcgtccattatac
aggcatgttggaggacggcaaaaaggtggacagtagtagagatcgcaataaaccttcaaattc
atgttgggaaaacaagaagtcattaggggatgggaggagggcgtggctcaaatgtccgtcggcc
aacgcgctaagctcaccatcagccccgactacgcatacggcgctaccggacatcccggaattat
tcccctcacgctaccttggtgtttgacgtcgaactgttgaagctcgagactagaggagtgcag
gtggagactatctcccaggagacgggcgcaccttccccaagcgcggccagacctgcgtggtgc
actacaccggggatgcttgaagatggaaagaaagttgattcctcccgggacagaaacaagcccctt
taagtttatgctaggcaagcaggaggtgatccgaggctgggaagaaggggttgcccagatgagt
gtgggtcagagagccaaactgactatatctccagattatgcctatggtgccactgggcacccag
gcatcatcccaccacatgccactctcgtcttcgatgtggagcttctaaaactggaaactagt
(SEQ ID NO:10)

Casp8:
agtgaatcacagactttggacaaagtttaccaaatgaaaagcaaacctcggggatactgtctga
tcatcaacaatcacaattttgcaaaagcacgggagaaagtgcccaaacttcacagcattaggga
caggaatggaacacacttggatgcaggggctttgaccacgacctttgaagagcttcattttgag
atcaagccccacgatgactgcacagtagagcaaatctatgagattttgaaaatctaccaactca
tggaccacagtaacatggactgcttcatctgctgtatcctctcccatggagacaagggcatcat
ctatggcactgatggacaggaggcccccatctatgagctgacatctcagttcactggtttgaag
tgcccttccttgctggaaaacccaaagtgttttttattcaggcttgtcaggggggataactacc
agaaaggtatacctgttgagactgattcagaggagcaaccctatttagaaatggatttatcatc
acctcaaacgagatatatcccggatgaggctgactttctgctggggatggccactgtgaataac
tgtgtttcctaccgaaaaccctgcagagggaacctggtacatccagtcactttgccagagcctga
gagagcgatgtcctcgaggcgatgatattctcaccatcctgactgaagtgaactatgaagtaag
caacaaggatgacaagaaaaacatggggaaacagatgcctcagcctactttcacactaagaaaa
aaacttgtcttcccttctgat (SEQ ID NO:11)

Flag/Tag/Stop:
Gattacaaggatgacgacgataagtga (SEQ ID NO:12)

3'UTR:
ggatc (SEQ ID NO:13)

Multiple cloning site (MluI, PacI, XhoI, PmeI)
aacctcgaggaattcACGCGTTTAATTAACTCGAGGTTT (SEQ ID NO:14)

*Fig. 2C*

IRES, GFP:
TCGAGGTCGACGGTATCGATAAGCTTGATATCGAATTCCGCCCCTCTCCCTCCCCCCCCCTAA
CGTTACTGGCCGAAGCCGCTTGGAATAAGGCCGGTGTGCGTTTGTCTATATGTTATTTTCCACC
ATATTGCCGTCTTTTGGCAATGTGAGGGCCCGGAAACCTGGCCCTGTCTTCTTGACGAGCATTC
CTAGGGGTCTTTCCCCTCTCGCCAAAGGAATGCAAGGTCTGTTGAATGTCGTGAAGGAAGCAGT
TCCTCTGGAAGCTTCTTGAAGACAAACAACGTCTGTAGCGACCCTTTGCAGGCAGCGGAACCCC
CCACCTGGCGACAGGTGCCTCTGCGGCCAAAAGCCACGTGTATAAGATACACCTGCAAAGGCGG
CACAACCCCAGTGCCACGTTGTGAGTTGGATAGTTGTGGAAAGAGTCAAATGGCTCTCCTCAAG
CGTATTCAACAAGGGGCTGAAGGATGCCCAGAAGGTACCCCATTGTATGGGATCTGATCTGGGG
CCTCGGTGCACATGCTTTACATGTGTTTAGTCGAGGTTAAAAAAACGTCTAGGCCCCCCGAACC
ACGGGGACGTGGTTTTCCTTTGAAAAACACGATGATAATATGGCCACAACCATGGTGAGCAAGG
GCGAGGAGCTGTTCACCGGGGTGGTGCCCATCCTGGTCGAGCTGGACGGCGACGTAAACGGCCA
CAAGTTCAGCGTGTCCGGCGAGGGCGAGGGCGATGCCACCTACGGCAAGCTGACCCTGAAGTTC
ATCTGCACCACCGGCAAGCTGCCCGTGCCCTGGCCCACCCTCGTGACCACCCTGACCTACGGCG
TGCAGTGCTTCAGCCGCTACCCCGACCACATGAAGCAGCACGACTTCTTCAAGTCCGCCATGCC
CGAAGGCTACGTCCAGGAGCGCACCATCTTCTTCAAGGACGACGGCAACTACAAGACCCGCGCC
GAGGTGAAGTTCGAGGGCGACACCCTGGTGAACCGCATCGAGCTGAAGGGCATCGACTTCAAGG
AGGACGGCAACATCCTGGGGCACAAGCTGGAGTACAACTACAACAGCCACAACGTCTATATCAT
GGCCGACAAGCAGAAGAACGGCATCAAGGTGAACTTCAAGATCCGCCACAACATCGAGGACGGC
AGCGTGCAGCTCGCCGACCACTACCAGCAGAACACCCCCATCGGCGACGGCCCCGTGCTGCTGC
CCGACAACCACTACCTGAGCACCCAGTCCGCCCTGAGCAAAGACCCCAACGA (SEQ ID
NO:15)

Rabbit B-globin PA:
GAAGCGCGATCACATGGTCCTGCTGGAGTTCGTGACCGCCGCCGGGATCACTCTCGGCATGGAC
GAGCTGTACAAGTAAAGCGGCCGCGATCTTTTCCCTCTGCCAAAAATTATGGGGACATCATGA
AGCCCCTTGAGCATCTGACTTCTGGCTAATAAAGGAAATTTATTTTCATTGCAATAGTGTGTTG
GAATTTTTTGTGTCTCTCACTCGGAAGGACATATGGGAGGGCAAATCATTTAAAACATCAGAAT
GAGTATTTGGTTTAGAGTTTGGCAACATATGCCATATGCTGGCTGCCATGAACAAAGGTGGCTA
TAAAGAGGTCATCAGTATATGAAACAGCCCCTGCTGTCCATTCCTTATTCCATAGAAAAGCCT
TGACTTGAGGTTAGATTTTTTTTATATTTTGTTTTGTGTTATTTTTTTCTTTAACATCCCTAAA
ATTTTCCTTACATGTTTTACTAGCCAGATTTTTCCTCCTCTCCTGACTACTCCCAGTCATAGCT
GTCCCTCTTCTCTTATGAAGATCCCTCGACCTGCAGCCCAAGCTTGGCGTAAT (SEQ ID
NO:16)

M13-rev:
CATGGTCATAGCTGTTTCCTGTGTGA (SEQ ID NO:17)

Fig. 2D

LacO:
AATTGTTATCCGCTCACAATTCCACACAACATACGAGCCGGAAGCATAAAGTGTAAAGCCTGGG
GTGCCTAATGAGTGAGCTAACTCACATTAATTGCGTTGCGCTCACTGCCCGCTTTCCAGTCGGG
AAACCTGTCGTGCCAGCGGATCCGCATCTCAATTAGTCAGCAACCATAGTCCCGCCCCTAACTC
CGCCCATCCCGCCCCTAACTCCGCCCAGTTCCGCCCATTCTCCGCCCCATGGCTGACTAATTTT
TTTTATTTATGCAGAGGCCGAGGCCGCCT (SEQ ID NO:18)

FseI, linker:
AAACGGCCGGCCATcgataccgtcgacctcgagggggggcccggtacccagcttttgt (SEQ ID NO:19)

T3:
Tccctttagtgagggttaattgcgcgcttggcgtaat (SEQ ID NO:20)

M13-rev:
Catggtcatagctgtttcctgtgtga (SEQ ID NO:21)

LacO:
Aattgttatccgctcacaattccacacaacatacgagccggaagcataaagtgtaaagcctggg
gtgcctaatgagtgagctaactcacattaattgcgttgcgctcactgcccgctttccagtcggg
aaacctgtcgtgccagctgcattaatgaatcggccaacgcgcggggagaggcggtttgcgtatt
gggcgctcttccgcttcctcgctcactgactcgctgcgctcggtcgttcggctgcggcgagcgg
tatcagctcactcaaaggcggtaatacggttatccacagaatcaggggataacgcaggaaagaa
catgtgagcaaaaggccagcaaaaggccaggaaccgtaaaaa (SEQ ID NO:22)

ColE1 origin:
Ggccgcgttgctggcgtttttccataggctccgcccccctgacgagcatcacaaaaatcgacgc
tcaagtcagaggtggcgaaacccgacaggactataaagataccaggcgtttccccctggaagct
ccctcgtgcgctctcctgttccgaccctgccgcttaccggatacctgtccgcctttctccctt
gggaagcgtggcgctttctcatagctcacgctgtaggtatctcagttcggtgtaggtcgttcgc
tccaagctgggctgtgtgcacgaaccccccgttcagcccgaccgctgcgccttatccggtaact
atcgtcttgagtccaacccggtaagacacgacttatcgccactggcagcagccactggtaacag
gattagcagagcgaggtatgtaggcggtgctacagagttcttgaagtggtggcctaactacggc
tacactagaaggacagtatttggtatctgcgctctgctgaagccagttaccttcggaaaaagag
ttggtagctcttgatccggcaaacaaaccaccgctggtagcggtggtttttttgtttgcaagca
gcagattacgcgcagaaaaaaaggatctcaagaagatcctttgatcttttctacggggtctgac
gctcagtggaacgaaaactcacgttaagggattttggtcatgagattatcaaaaaggatcttca
cctagatcctttaaattaaaaatgaagttttaaatcaatctaaagtatatatgagtaaacttg
gtctgacagtta (SEQ ID NO:23)

*Fig. 2E*

AmpR:
Ccaatgcttaatcagtgaggcacctatctcagcgatctgtctatttcgttcatccatagttgcc
tgactccccgtcgtgtagataactacgatacgggagggcttaccatctggccccagtgctgcaa
tgataccgcgagacccacgctcaccggctccagatttatcagcaataaaccagccagccggaag
ggccgagcgcagaagtggtcctgcaactttatccgcctccatccagtctattaattgttgccgg
gaagctagagtaagtagttcgccagttaatagtttgcgcaacgttgttgccattgctacaggca
tcgtggtgtcacgctcgtcgtttggtatggcttcattcagctccggttcccaacgatcaaggcg
agttacatgatcccccatgttgtgcaaaaaagcggttagctccttcggtcctccgatcgttgtc
agaagtaagttggccgcagtgttatcactcatggttatggcagcactgcataattctcttactg
tcatgccatccgtaagatgcttttctgtgactggtgagtactcaaccaagtcattctgagaata
gtgtatgcggcgaccgagttgctcttgcccggcgtcaatacgggataataccgcgccacatagc
agaactttaaaagtgctcatcattggaaaacgttcttcggggcgaaaactctcaaggatcttac
cgctgttgagatccagttcgatgtaacccactcgtgcacccaactgatcttcagcatcttttac
tttcaccagcgtttctgggtgagcaaaaacaggaaggcaaaatgccgcaaaaaagggaataagg
gcgacacggaaatgttgaatactcatactcttcctttttcaatattattgaagcatttatcagg
gttattgtctcatgagcggatacatatttgaatgtatttagaaaaataaacaaataggggttcc
gcgcacatttccccgaaaagtgccac (SEQ ID NO:24)

Fig. 2F

```
ATGGCTTCCAAGGTGTACGACCCCGAGCAACGCAAACGCATGATCACTGGGCCTCAGTGGTGGGCT
CGCTGCAAGCAAATGAACGTGCTGGACTCCTTCATCAACTACTATGATTCCGAGAAGCACGCCGAG
AACGCCGTGATTTTTCTGCATGGTAACGCTGCCTCCAGCTACCTGTGGAGGCACGTCGTGCCTCAC
ATCGAGCCCGTGGCTAGATGCATCATCCCTGATCTGATCGGAATGGGTAAGTCCGGCAAGAGCGGG
AATGGCTCATATCGCCTCCTGGATCACTACAAGTACCTCACCGCTTGGTTCGAGCTGCTGAACCTT
CCAAAGAAAATCATCTTTGTGGGCCACGACTGGGGGGCTTGTCTGGCCTTTCACTACTCCTACGAG
CACCAAGACAAGATCAAGGCCATCGTCCATGCTGAGAGTGTCGTGGACGTGATCGAGTCCTGGGAC
GAGTGGCCTGACATCGAGGAGGATATCGCCCTGATCAAGAGCGAAGAGGGCGAGAAAATGGTGCTT
GAGAATAACTTCTTCGTCGAGACCATGCTCCCAAGCAAGATCATGCGGAAACTGGAGCCTGAGGAG
TTCGCTGCCTACCTGGAGCCATTCAAGGAGAAGGGCGAGGTTAGACGGCCTACCCTCTCCTGGCCT
CGCGAGATCCCTCTCGTTAAGGGAGGCAAGCCCGACGTCGTCCAGATTGTCCGCAACTACAACGCC
TACCTTCGGGCCAGCGACGATCTGCCTAAGATGTTCATCGAGTCCGACCCTGGGTTCTTTTCCAAC
GCTATTGTCGAGGGAGCTAAGAAGTTCCCTAACACCGAGTTCGTGAAGGTGAAGGGCCTCCACTTC
AGCCAGGAGGACGCTCCAGATGAAATGGGTAAGTACATCAAGAGCTTCGTGGAGCGCGTGCTGAAG
AACGAGCAGCTCGAGAATTCTCACGCGTCTGCAGGATATCAAGCTTCCACCATGGCCTCCTCCGAG
GACGTCATCAAGTTCATGCGCTTCAAGGTGCGCATGGAGGGCTCCGTGAACGGCCACGAGTTCGAG
ATCGAGGGCGAGGGCGAGGGCCGCCCCTACGAGGGCACCCAGACCGCCAAGCTGAAGGTGACCAAG
GGCGGCCCCCTGCCCTTCGCCTGGGACATCCTGTCCCTCAGTTCCAGTACGGCTCCAAGGCCTAC
GTGAAGCACCCCGCCGACATCCCCGACTACTTGAAGCTGTCCTTCCCCGAGGGCTTCAAGTGGGAG
CGCGTGATGAACTTCGAGGACGGCGGCGTGGTGACCGTGACCCAGGACTCCTCCCTGCAGGACGGC
GAGTTCATCTACAAGGTGAAGCTGCGCGGCACCAACTTCCCCTCCGACGGCCCCGTAATGCAGAAG
AAGACCATGGGCTGGGAGGCCTCCACCGAGAGGATGTACCCCGAGGACGGCGCCCTGAAGGGCGAG
ATCAAGATGAGGCTGAAGCTGAAGGACGGCGGCCACTACGACGCCGAGGTCAAGACCACCTACATG
GCCAAGAAGCCCGTGCAGCTGCCCGGCGCCTACAAGACCGACATCAAGCTGGACATCACCTCCCAC
AACGAGGACTACACCATCGTGGAACAGTACGAGCGCGCCGAGGGCCGCCACTCCACCGGCGCCACC
GCGGGCCCGGGATCCGCCACCATGCCCACGCTACTGCGGGTTTATATAGACGGTCCCCACGGGATG
GGGAAAACCACCACCACCACGCAACTGCTGGTGGCCCTGGGTTCGCGCGACGATATCGTCTACGTA
CCCGAGCCGATGACTTACTGGCGGGTGCTGGGGCTTCCGAGACAATCGCGAACATCTACACCACA
CAACACCGCCTCGACCAGGGTGAGATATCGGCCGGGGACGCGGCGGTGGTAATGACAAGCGCCCAG
ATAACAATGCCTTATGCCGTGACCGACGCCGTTCTGGCTCCTCATATCGGGGGGAGGCTGGGAGC
TCACATGCCCCGCCCCCGGCCCTCACCATCTTCCTCGACCGCCATCCCATCGCCTTCATGCTGTGC
TACCCGGCCGCGCGGTACCTTATGGGCAGCATGACCCCCAGGCCGTGCTGGCGTTCGTGGCCCTC
ATCCCGCCGACCTTGCCCGGCACCAACATCGTGCTTGGGGCCCTTCCGGAGGACAGACACATCGAC
CGCCTGGCCAAACGCCAGCGCCCCGGCGAGCGGCTGGACCTGGCTATGCTGGCTGCGATTCGCCGC
GTTTACGGGCTACTTGCCAATACGGTGCGGTATCTGCAGTGCGGCGGGTCGTGGCGGGAGGACTGG
GGACAGCTTTCGGGGACGGCCGTGCCGCCCCAGGGTGCCGAGCCCCAGAGCAACGCGGGCCCACGA
CCCCATATCGGGGACACGTTATTTACCCTGTTTCGGGCCCCCGAGTTGATGGCCCCCAACGGCGAC
CTGTATAACGTGTTTGCCTGGGCCTTGGACGTCTTGGCCAAACGCCTCCGTTCCATGCACGTCTTT
ATCCTGGATTACGACCAATCGCCCGCCGGCTGCCGGGACGCCCTGCTGCAACTTACCTCCGGGATG
GTCCAGACCCACGTCACCACCCCCGGCTCCATACCGACGATATGCGACCTGGCGCGCACGTTTGCC
CGGGAGATGGGGGAGGCTAACTGA (SEQ ID NO:25)
```

*FIG. 3*

NUCLEIC ACID CONSTRUCT WITH A P16 PROMOTER THAT CAUSES A PRODRUG CONVERTING ENZYME TO BE EXPRESSED SPECIFICALLY IN SENESCENT CELLS

CROSS-REFERENCE TO RELATED APPLICATIONS

This application is a Continuation of U.S. application Ser. No. 15/067,543, filed Mar. 11, 2016, which is a Continuation of U.S. application Ser. No. 13/975,179, filed Aug. 23, 2013, which claims the benefit under 35 U.S.C. § 119(e) of U.S. Provisional Application No. 61/692,613 filed Aug. 23, 2012, U.S. Provisional Application No. 61/837,096 filed Jun. 19, 2013, which applications are incorporated herein by reference in their entirety.

JOINT RESEARCH AGREEMENT

For purposes of this disclosure, the Buck Institute for Research on Aging and the Erasmus University Medical Center in Rotterdam were parties to a joint research agreement.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 44237-719-302-SL.txt. The text file is 32 KB, was created on Jan. 11, 2018, and is being submitted electronically via EFS-Web.

BACKGROUND

Technical Field

This disclosure relates to non-human animal models for age-related disorders and age-sensitive traits associated with senescence-inducing stimuli, methods for identifying therapeutic agents for treating or preventing age-related disorders and age-sensitive traits associated with senescence-inducing stimuli, and methods for treating or preventing age-related disorders and age-sensitive traits. It also relates to therapeutic agents and pharmaceutical compositions for treating or preventing age-related disorders and age-sensitive traits associated with senescence-inducing stimuli.

Description of the Related Art

The American Cancer Society estimates that there will be more than 1.6 million new cases of cancer in 2012 in the United States alone. More than half of these patients will receive chemotherapy and/or treatment with radiation in addition to undergoing surgical resection of the tumor. Various chemotherapeutics and radiation are known to induce cellular senescence. Given that senescent cells have been causally implicated in certain aspects of age-related decline in health and may contribute to certain diseases, the induction of senescent cells resulting from necessary live-preserving chemotherapeutic and radiation treatments may have deleterious effects to millions of patients worldwide (e.g. fatigue, weakness, loss of physical agility). As such, treatments aimed at clearing therapy-induced senescent cells and improving age-sensitive traits associated with the same have the potential to markedly improve the health, lifespan and quality of life for patients exposed to senescence-inducing stimuli. The present disclosure addresses these needs and offers numerous related advantages.

BRIEF SUMMARY

Briefly, provided herein are animal models, methods for identifying therapeutic agents, and therapeutic agents useful for treating and/or preventing age-related disorders and age-sensitive traits, particularly those cause by senescence-inducing stimuli. For example, provided herein are the following embodiments.

The present disclosure provides, in one embodiment, a non-human animal model for aging comprising a non-human animal that (a) exhibits an age-related disorder or age-sensitive trait and (b) comprises a transgene selectively expressed by senescent cells, wherein the animal is exposed to or treated with a senescence-inducing stimulus. In another embodiment, the transgene comprises a senescent cell-specific promoter. In a more specific embodiment, the promoter is derived from $p16^{Ink4a}$.

In another embodiment, the transgene expresses at least one detectable label, a cytotoxic agent, a cytotoxicity-activating molecule, an RNA, or a combination thereof. In still another embodiment, the detectable label is selected from the group consisting of (a) luciferase; (b) a red fluorescent protein; (c) a green fluorescent protein; and (d) a luciferase and a red fluorescent protein. In yet another embodiment, the cytotoxicity-activating molecule is a truncated herpes simplex virus thymidine kinase or a FK506-binding protein (FKBP)-caspase fusion polypeptide.

In a further embodiment, the detectable label is selected from the group consisting of (a) luciferase; (b) a red fluorescent protein; (c) a green fluorescent protein; and (d) a luciferase and a red fluorescent protein; and wherein the cytotoxicity-activating molecule is a truncated herpes simplex virus thymidine kinase or a FKBP-caspase fusion polypeptide.

In still another embodiment, the transgene comprises (a) a $p16^{Ink4a}$ promoter operatively linked to a polynucleotide sequence encoding a FKBP-caspase fusion polypeptide (p16-FKBP-caspase transgene), and to a polynucleotide sequence encoding a green fluorescence protein, or (b) a $p16^{Ink4a}$ promoter operatively linked to a polynucleotide sequence encoding a fusion polypeptide comprising a luciferase, a red fluorescent protein, and a truncated herpes simplex virus thymidine kinase (p16-3MR transgene).

In yet another embodiment, the transgene comprises a $p16^{Ink4a}$ promoter operatively linked to a polynucleotide sequence encoding a FKBP-caspase fusion polypeptide (p16-FKBP-caspase transgene), and to a polynucleotide sequence encoding a green fluorescence protein.

In a further embodiment, the transgene comprises a $p16^{Ink4a}$ promoter operatively linked to a polynucleotide sequence encoding a fusion polypeptide comprising a luciferase, a red fluorescent protein, and a truncated herpes simplex virus thymidine kinase (p16-3MR transgene).

In another embodiment, the senescence-inducing stimulus gives rise to an age-related disorder or age-sensitive trait. In a more specific embodiment, the senescence-inducing stimulus comprises exposure to irradiation or treatment with a chemotherapeutic agent. In another specific embodiment, the chemotherapeutic agent is doxorubicin, taxol, docetaxel, gemcitabine, or cisplatin. In yet another specific embodiment, the irradiation is whole body gamma radiation.

In still another embodiment, the age-related disorder or age-sensitive trait results at least in part from (1) a genetic modification; (2) a diet modification; (3) a chemical induction; (4) radiation induction; or (5) any combination thereof. For example, in a more specific embodiment, the age-related disorder or age-sensitive trait results at least in part from a genetic modification, wherein the genetic modification comprises (1) expression of a second transgene; (2) reduced or abrogated expression of an endogenous gene, or (3) a combination thereof. In another specific embodiment, the animal is a BubR1 mouse.

The present disclosure provides, in another embodiment, a non-human animal model comprising a transgene that comprises (1) a senescent cell-specific promoter operatively linked to a polynucleotide encoding (a) at least one detectable label, (b) a cytotoxic agent, (c) a cytotoxicity-activating molecule, (d) an RNA, or (e) any combination of (a), (b), (c), and (d); and wherein the animal exhibits an age-sensitive trait. In another embodiment, the transgene comprises a $p16^{Ink4a}$ promoter operatively linked to a polynucleotide sequence encoding a FKBP-caspase fusion polypeptide (p16-FKBP-caspase transgene) and a green fluorescent protein. In still another embodiment, the transgene comprises a $p16^{Ink4a}$ promoter operatively linked to a polynucleotide sequence encoding a fusion polypeptide comprising a luciferase, a red fluorescent protein, and a truncated herpes simplex virus thymidine kinase (p16-3MR transgene).

In yet another embodiment, the age-sensitive trait is measure of a specific T cell subset distribution, cataract formation, spontaneous activity, motor coordination, cognitive capacity, physical function, body composition, cardiac function, or any combination thereof. In a more specific embodiment, the body composition is a measure of sarcopenia, osteoporosis, bone mineral density, lean mass or fat mass. In a related embodiment, the lean mass, fat mass and bone mineral density are measured by QNMR, dual-energy X-ray absorptiometry, MRI, PET, or a combination thereof. In another related embodiment, the physical function is a measure of (1) running time, distance, and work using a motorized treadmill, (2) grip strength using a grip meter, or (3) any combination measure thereof. In another embodiment, the age-sensitive trait is a measure of a tissue or organ, wherein the measure is of fiber diameter on gastrocnemius muscle, DNA damage, renal and glomerulosclerosis, retinal atrophy, proteotoxic stress, oxidative stress, or hematopoietic system.

The present disclosure provides, in another embodiment, a method for identifying a therapeutic agent effective for treating or reducing the risk of developing an age-related disorder or age-sensitive trait, said method comprising:

(a) administering a candidate therapeutic agent to the animal of the aging animal model of the present disclosure, to provide a treated animal;

(b) (1) determining an age-related disorder or age-sensitive trait exhibited in the treated animal, and comparing to the age-related disorder or age-sensitive trait exhibited in an untreated control aging model animal, or (2) determining the level of suppression of cellular senescence in the treated animal and comparing to the level of cellular senescence in the untreated control animal wherein (1) suppression of an age-related disorder or age-sensitive trait or (2) suppression of cellular senescence in the treated animal compared with the untreated animal identifies an agent effective for treating or preventing an age-related disorder or age-sensitive trait.

In a more specific embodiment, step (b) comprises:

(1) determining an age-related disorder or age-sensitive trait exhibited in the treated animal, and comparing to the age-related disorder or age-sensitive trait exhibited in an untreated control aging model animal; and (2) determining the level of suppression of cellular senescence in the treated animal and comparing to the level of cellular senescence in the untreated control animal; and wherein (1) suppression of an age-related disorder or age-sensitive trait and (2) suppression of cellular senescence in the treated animal compared with the untreated animal identifies an agent effective for treating or preventing an age-related disorder or age-sensitive trait In a related embodiment, suppression of cellular senescence comprises suppression of the expression or secretion of one or more senescent cell-associated molecules in the animal. In yet another related embodiment, suppression of cellular senescence comprises reducing the quantity of senescent cells in the animal.

The present disclosure provides, in another embodiment, a therapeutic agent for treating or reducing the likelihood of developing an age-related disorder or age-sensitive trait, wherein the therapeutic agent is identified according to a method of the present disclosure.

The present disclosure provides, in another embodiment, a method for treating or reducing the likelihood of developing an age-related disorder or age-sensitive trait in a subject who has an age-related disorder or age-sensitive trait, who is in remission for an age-related disorder or age-sensitive trait, or who is at risk of developing a recurrence of an age-related disorder or age-sensitive trait, comprising administering to the subject the therapeutic agent of the present disclosure.

The present disclosure also provides, in another embodiment, a method for treating or reducing the likelihood of an age-related disorder or age-sensitive trait in a subject who has an age-related disorder or age-sensitive trait, who is in remission for an age-related disorder or age-sensitive trait, or who is at risk of developing a recurrence of an age-related disorder or age-sensitive trait, said method comprising administering a therapeutic agent that selectively suppresses cellular senescence in the subject, thereby treating or reducing the likelihood of an age-related disorder or age-sensitive trait in the subject. In another embodiment, suppressing cellular senescence comprises suppressing the expression or secretion of one or more senescent cell-associated molecules in the subject. In a related embodiment, suppressing cellular senescence comprises reducing the quantity of senescent cells in the subject.

The present disclosure also provides, in another embodiment, an isolated cell or cell line derived from the animal model of the present disclosure.

The present disclosure further provides, in another embodiment, a method for producing the non-human animal of the model of the present disclosure, comprising (a) providing a non-human animal that comprises a transgene selectively expressed by senescent cells; and (b) aging the animal to produce an age-related disorder or age-sensitive trait.

In the following description, certain specific details are set forth in order to provide a thorough understanding of various embodiments. However, one skilled in the art will understand that the invention may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." In addition, the term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features. Headings provided herein are for convenience only and do not interpret the scope or meaning of the claimed embodiments.

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Also, as used in this specification and the appended claims, the singular forms "a," "an," and "the" include plural referents unless the content clearly dictates otherwise. Thus, for example, reference to "a non-human animal" may refer to one or more non-human animals, or a plurality of such animals, and reference to "a cell" or "the cell" includes reference to one or more cells and equivalents thereof (e.g., plurality of cells) known to those skilled in the art, and so forth. When steps of a method are described or claimed, and the steps are described as occurring in a particular order, the description of a first step occurring (or being performed) "prior to" (i.e., before) a second step has the same meaning if rewritten to state that the second step occurs (or is performed) "subsequent" to the first step. The term "about" when referring to a number or a numerical range means that the number or numerical range referred to is an approximation within experimental variability (or within statistical experimental error), and thus the number or numerical range may vary between 1% and 15% of the stated number or numerical range. It should also be noted that the term "or" is generally employed in its sense including "and/or" unless the content clearly dictates otherwise. The term, "at least one," for example, when referring to at least one compound or to at least one composition, has the same meaning and understanding as the term, "one or more."

BRIEF DESCRIPTION OF THE DRAWINGS

FIGS. 1A-1D include a listing of an exemplary transgene selectively expressed in senescent cells, the nucleic acid sequence of a pBLUESCRIPT II KS vector containing a p16$^{Ink4a}$ promoter-FKBP-caspase 8-IRES-GFP nucleic acid construct.

FIGS. 2A-2F include a listing of the nucleic acid sequence of FIG. 1 with the various vector components and construct components labeled.

FIG. 3 represents an exemplary 3MR transgene sequence.

DETAILED DESCRIPTION

Figure 4:
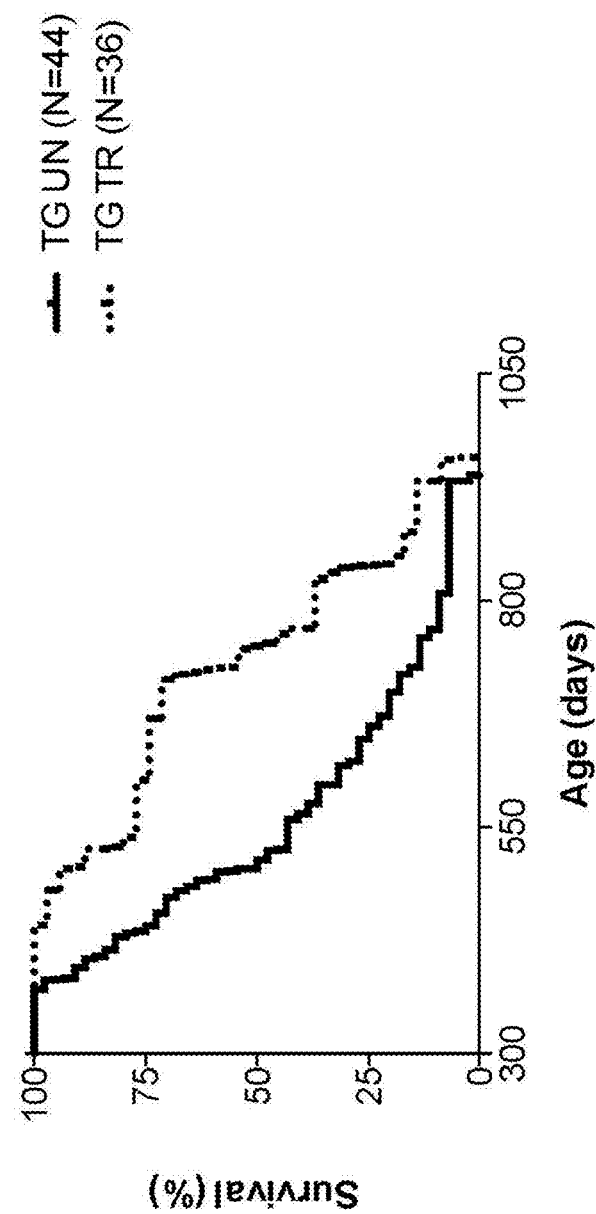
FIG. 4 illustrates lifespan difference between wild-type INK-ATTAC transgenic mice treated with AP20187 (TG TR) and untreated wild-type INK-ATTAC transgenic mice (TG UN).

The present disclosure relates generally to non-human animal models of aging. More specifically, the present disclosure provides non-human animal models of aging, age-related disorders, age-sensitive traits, and the like, wherein the animals models comprise transgenes selectively expressed by senescent cells, and wherein the age-related disorders and age-sensitive traits result at least in part from senescence-inducing stimuli, such as treatment with chemotherapy or radiation. For example, in certain embodiments, the animal models comprise a transgene that allows for the selective and controllable ablation of senescent cells at a desired time or for a desired period relative to exposure of the animals to senescence-inducing stimuli. The animal models are advantageously used for determining the deleterious health effects of senescence-inducing stimuli and for identifying therapeutic agents effective for treating or preventing age-related disorders and age-sensitive traits associated with or caused by such stimuli. As described herein, the present disclosure also provides therapeutic agents identified using such methods, pharmaceutical compositions comprising the identified therapeutic agents, and methods of treating or preventing age-related disorders and age-specific traits associated with senescence-inducing stimuli.

Transgenic Animals with Senescent Cell-Specific Transgene Expression

Certain aspects of the present disclosure employ non-human animals, particularly genetically modified non-human animals, wherein the animals comprise a transgene expressed under the control of a senescent cell-specific promoter, and wherein the animals are exposed to or treated with at least one senescence-inducing stimulus, such as chemotherapy or radiation. In certain more specific embodiments, the animals comprise a transgene that allows for the selective and controllable ablation of senescent cells.

By operably linking a senescent cell-specific promoter of a transgene to a nucleic acid sequence encoding a polypeptide of interest (e.g., a detectable label or cytotoxicity-activating molecule), senescent cells within an animal can be monitored and/or deleted in a controlled and user-determined fashion. In certain embodiments, for example, the present disclosure employs transgenic non-human animals that can be induced to delete senescent cells in vivo at a predetermined and desired point in time, such as at a particular stage of development or disease.

In addition to the transgene selectively expressed by senescent cells, an animal model of the present disclosure, to which a senescence-inducing stimulus is administered, may further contain other genetic or non-genetic modifications, or may be exposed to or administered other agents or treatments that are known to accelerate or facilitate the aging process in the animal and/or that contribute to the development of an age-related disorder or age-sensitive trait in the animal. For example, as further described herein, the nonhuman animals comprising a senescent cell-specific transgene may be advantageously crossed with other animals, which, due to one or more genetic modifications, for example, are known to develop a desired age-related phenotype, age-related disorder and/or age-sensitive trait of interest.

In this way, an animal model may be generated according to the present disclosure which is genetically or otherwise modified to develop a desired age-related phenotype, age-related disorder and/or age-sensitive trait, wherein the role of senescence-inducing stimuli in relation to an animal's age-related phenotype, age-related disorder and/or age-sensitive trait may be evaluated. The animal model may be further employed in screening methods in order to identify therapeutic agent that suppress or otherwise advantageously effect senescent cell survival, viability and/or clearance in the context of the animal model.

A senescent cell-specific promoter sequence present within a transgene of the present disclosure can be essentially any sequence that selectively drives expression of a polypeptide encoded by the transgene or expression of a nucleic acid sequence (e.g., an RNA) in senescent cells, while driving less, little, or no expression of the encoded polypeptide or nucleic acid sequence in non-senescent cells. In certain exemplary embodiments, a senescent cell-specific promoter used in accordance with the present disclosure may include, without limitation, a p16$^{Ink4a}$ promoter sequence, a p21cip promoter sequence, or a Pai1 promoter sequence.

In certain embodiments, the present disclosure provides a non-human animal model comprising a transgene that comprises (1) a senescent cell-specific promoter operatively linked to a polynucleotide encoding (a) at least one detectable label, (b) a cytotoxic agent, (c) a cytotoxicity-activating molecule, (d) an RNA, or (e) any combination of (a), (b), (c) and (d); and that exhibits a phenotype of an age-related disease.

It will be understood that a senescent cell-specific promoter can be operably linked to a nucleic acid sequence encoding any polypeptide of interest. In certain embodiments, the polypeptide of interest is selected from a detectable label, a cytotoxic molecule (e.g., a polypeptide capable of killing a senescent cell in which it is expressed) and a cytotoxicity-activating molecule (e.g., a polypeptide capable of facilitating the killing of a cell in which it is expressed), or a combination thereof. In certain embodiments, the transgene can be operably linked to an RNA (e.g., siRNA, shRNA, microRNA, and the like, which reduces or abrogates the expression of one or more genes important or essential for senescent cell survival), or a combination thereof.

Depending on the polypeptide of interest that is encoded by the transgene, it will be understood that different promoter features may be advantageous or desired. For example, as will be understood, in embodiments wherein a transgene encodes a polypeptide that is directly cytotoxic to cells in which it is expressed, the senescent cell-specific promoter of the transgene will need to be an inducible promoter in order to control the timing of expression of the cytotoxic polypeptide, and thereby control the deletion of senescent cells in the animal. If, on the other hand, a transgene encodes a cytotoxicity-activating polypeptide, the transgene promoter need not be inducible. Rather, the inducibility of the system in this instance relies upon the timing of exposure of the cytotoxicity-activating molecule expressed by senescent cells to its activating agent, as further described below.

Any of a number of detectable labels may be operably linked to a senescent cell-specific promoter. Many such detectable labels, and the means by which they can be detected, have been described and are well known and established in the art. In some embodiments, the detectable label comprises one or more fluorescent or bioluminescent labels, many of which are well known and established in the art. For example, the fluorescent protein may be any protein that fluoresces and that may be visualized when expressed in senescent cells under the control of a senescent cell-specific promoter as described herein. Illustrative fluorescent proteins can include, for example, green fluorescent protein (GFP), modified or enhanced green fluorescent protein (EGFP), red fluorescent protein (RFP), and various other known fluorescent proteins such as EBFP, EBFP2, Azurite, mKalamal, ECFP, Cerulean, CyPet, YFP, Citrin, Venus, and Wet. Other illustrative fluorescent or bioluminescent proteins include, for example, infrared-fluorescent proteins (IFPs), mRFP1, mCherry, mOrange, DsRed, tdTomato, mKO, TagRFP, mOrange2, maple, TagRFP-T, Firefly Luciferase, Renilla Luciferase and Click Beetle Luciferase. Still other illustrative labels can include yellow fluorescent protein, cyan FP, blue FP, red FP and their enhanced versions. It will be understood that essentially any of a number of other luminescent or fluorescent proteins that can emit light can be used in this context.

In certain specific embodiments, a detectable label present within a transgene according to the disclosure is selected from the group consisting of (a) luciferase; (b) a red fluorescent protein; (c) a green fluorescent protein; and (d) a luciferase and a red fluorescent protein.

Any of a number of cytotoxicity-activating molecules may be operably linked to a senescent cell-specific promoter to produce a suitable transgene for use in the context of the present disclosure. Following its expression in a senescent cell-specific fashion, the cytotoxicity-activating molecule is one that is capable of inducing the controllable killing of the senescent cells in which it is expressed upon administration of an activating agent to the transgenic animal. Illustrative examples of cytotoxicity-activating molecules include, but are not limited to herpes simplex virus (HSV) thymidine kinase (TK) polypeptides and FK506 binding protein (FKBP)-caspase fusion polypeptide. FK506 binding protein includes variant thereof, such as a Phe36Val mutant.

For example, in a specific embodiment, the cytotoxicity-activating molecule encoded by the transgene is a herpes simplex virus (HSV) thymidine kinase (TK) polypeptide (including truncated TK polypeptides) and the activating agent is ganciclovir.

In other embodiments, the cytotoxicity-activating molecule encoded by the transgene comprises two or more polypeptide sequences fused together (e.g., a fusion polypeptide). An example of such a fusion polypeptide can be a FKBP-caspase-8 fusion polypeptide. See, e.g., Pajvani et al., Nat. Med., 11:797-803 (2005) and Baker et al., Nature 479:232-36 (2011). Such fusion polypeptides may comprise, for example, one or more catalytic domains of human caspase-8 fused to one or more FKBP domains. Following transgene expression, adjacent FKBP molecules in the encoded polypeptide can be activated via forced dimerization using a suitable activating agent, thereby allowing for the regulated ablation of cells in which the fusion polypeptide is expressed. In a specific example, the p20 and p10 domains of human caspase-8 are fused to serial FKBPv (Phe36Val mutant FKBP) domains. Other examples of such polypeptides include, without limitation, a FKBP-caspase-1 fusion polypeptide or FKBP-caspase-3 fusion polypeptide (see, e.g., Mallet et al., *Nat. Biotechnol.* 20:1234-39 (2002)). In these and related embodiments, an illustrative activating agent used to induce cytotoxicity of senescent cells expressing the fusion polypeptide include the compound FK1012 analog AP20187 (referred to herein as AP20187) and related analogs. (see, e.g., U.S. Patent Application Publication No. 2004/0006233, the disclosure of which is incorporated herein by reference). To increase local concentrations of a FKBP-caspase fusion polypeptide, a myristoylation sequence may be included in the transgene to provide membrane attachment for the FKBP-caspase fusion polypeptide.

In this way, administration of a suitable cytotoxicity activating molecule to an animal at a desired time provides an effective means for selectively killing (e.g., by apoptosis) the senescent cells which express the cytotoxicity-activating molecule in the animal. In certain specific embodiments, less than 1%, 5%, 10% or 20% of non-senescent cells of the transgenic mouse are killed when an activating compound is administered to a transgenic mouse comprising a transgene encoding a cytotoxicity activating molecule.

Any of a number of nucleotide sequences encoding small RNAs whose expression affects expression or secretion of senescence cell-associated molecules may be operatively linked to a senescent cell-specific promoter. Such small RNAs include siRNA, shRNA, microRNA and the like (see, Finnegan and Matzke, *J. Cell Sci.* 226:4689-93, 2003). In certain embodiments, the expression of such small RNAs is under the control of an inducible senescent cell-specific promoter. Upon induction, the expression of the small RNAs down-regulates the expression or secretion of senescent cell-associated molecules of interest.

In some cases, a polypeptide encoded by a transgene of the present disclosure will be engineered to include one or more other elements, such as an affinity tag (e.g., a Flag tag), cellular localization sequence (e.g., myristoylation sequence) or any other desired element of interest.

In light of the above general disclosure, it will be evident that various more specific transgenes and transgenic non-human animals are provided for use herein. For example, in a specific embodiment, the animal model will comprise a transgene wherein a senescent cell-specific promoter directs expression of a detectable label selected from the group consisting of (a) luciferase; (b) a red fluorescent protein; (c) a green fluorescent protein; and (d) a luciferase and a red fluorescent protein; and further directs expression of a cytotoxicity-activating molecule selected from the group consisting of a truncated herpes simplex virus thymidine kinase and a FKBP-caspase fusion polypeptide.

In another specific embodiment, an animal model includes a transgene comprising (a) $p16^{Ink4a}$ promoter operatively linked to a polynucleotide sequence encoding a FKBP-caspase fusion polypeptide (p16-FKBP-caspase transgene) and to a polynucleotide sequence encoding a green fluorescent protein; or (b) $p16^{Ink4a}$ promoter operatively linked to a polynucleotide sequence encoding a fusion polypeptide comprising a luciferase, a red fluorescent protein, and a truncated herpes simplex virus thymidine kinase (tTK) (p16-3MR transgene), which may be called herein a trimodal fusion protein (3MR). In more specific embodiments, luciferase is renilla luciferase and red fluorescent protein is a monomeric red fluorescent protein. A $p16^{Ink4a}$ promoter may comprise a full-length promoter sequence or may comprise a functional (i.e., operable) truncation (or fragment) thereof (see, e.g., Wang et al. *J. Biol. Chem.* 276:48655-61 (2001)).

The non-human animal models of the present disclosure can be implemented in essentially any type of animal. Most typically, the animal model will be a mammal. In more specific embodiments, illustrative animal models include, but are not limited to, models derived from farm animals such as pigs, goats, sheep, cows, horses, and rabbits, rodents such as rats, guinea pigs, and mice, and non-human primates such as baboons, monkeys, and chimpanzees.

Transgenic nonhuman animal of the present disclosure can include, without limitation, founder transgenic non-human animals as well as progeny of the founders, progeny of the progeny, and so forth, provided that the progeny retain the transgene. The nucleated cells of the transgenic nonhuman animals provided herein can contain a transgene that includes a senescent cell-specific promoter sequence (e.g., a $p16^{Ink4a}$ promoter sequence, or an operable truncation thereof) operably linked to a nucleic acid sequence encoding a polypeptide of interest, such as a polypeptide that comprises a detectable label, a polypeptide capable of killing a cell (e.g., a cytotoxic polypeptide) and/or a polypeptide capable of facilitating the killing of a cell (e.g., a cytotoxicity-activating polypeptide), or a combination thereof.

In the context of transgenic animal production, operably linking a promoter sequence of interest to a nucleic acid sequence encoding a polypeptide of interest is well known and established. This generally involves positioning a regulatory element (e.g., a promoter sequence, an inducible element and/or an enhancer sequence) relative to a nucleic acid sequence encoding a polypeptide in such a way as to permit or facilitate expression of the encoded polypeptide. In the transgenes disclosed herein, for example, a promoter sequence (e.g., a $p16^{Ink4a}$ promoter sequence, or an operable truncation thereof) can be positioned 5' relative to a nucleic acid encoding a polypeptide of interest (e.g., an FKBP-caspase-8 fusion protein).

Various techniques known in the art can be used to introduce transgenes into non-human animals to produce founder lines, in which the transgene is integrated into the genome. Such techniques include, without limitation, pronuclear microinjection (See, e.g., U.S. Pat. No. 4,873,191), retrovirus mediated gene transfer into germ lines (Van der Putten et al., *Proc. Natl. Acad. Sci. USA*, 82:6148-1652 (1985)), gene targeting into embryonic stem cells (Thompson et al., *Cell* 56:313-321 (1989)), electroporation of embryos (Lo, *Mol. Cell. Biol.*, 3:1803-1814 (1983)), and in vitro transformation of somatic cells, such as cumulus or mammary cells, followed by nuclear transplantation (Wilmut et al., *Nature*, 385:810-813 (1997); and Wakayama et al., *Nature*, 394:369-374 (1998)). For example, fetal fibroblasts can be genetically modified to contain a desired transgene construct, and then fused with enucleated oocytes. After activation of the oocytes, the eggs are cultured to the blastocyst stage. See, for example, Cibelli et al., *Science*, 280:1256-1258 (1998). Standard breeding techniques can be used to create animals that are homozygous for the transgene from the initial heterozygous founder animals. Homozygosity is not required, however, as the phenotype can be observed in hemizygotic animals.

Once transgenic non-human animals have been generated, expression of an encoded polypeptide can be assessed using standard techniques. Initial screening can be accomplished by Southern blot analysis to determine whether or not integration of the transgene has taken place. For a description of Southern analysis, see sections 9.37-9.52 of Sambrook et al., 1989, Molecular Cloning, A Laboratory Manual, second edition, Cold Spring Harbor Press, Plainview; N.Y. Polymerase chain reaction (PCR) techniques also can be used in the initial screening. PCR refers to a procedure or technique in which target nucleic acids are amplified. Generally, sequence information from the ends of the region of interest or beyond is employed to design oligonucleotide primers that are identical or similar in sequence to opposite strands of the template to be amplified. PCR can be used to amplify specific sequences from DNA as well as RNA, including sequences from total genomic DNA or total cellular RNA. Primers typically are 14 to 40 nucleotides in length, but can range from 10 nucleotides to hundreds of nucleotides in length. PCR is described in, for example PCR Primer: A Laboratory Manual, ed. Dieffenbach and Dveksler, Cold Spring Harbor Laboratory Press, 1995. Nucleic acids also can be amplified by ligase chain reaction, strand displacement amplification, self-sustained sequence replication, or nucleic acid sequence-based amplified. See, for example, Lewis, *Genetic Engineering News*, 12:1 (1992); Guatelli et al., *Proc. Natl. Acad. Sci. USA,* 87:1874-1878 (1990); and Weiss, *Science,* 254:1292-1293 (1991).

Expression of a nucleic acid sequence encoding a polypeptide of interest in senescent cells of transgenic non-human animals can be assessed using techniques that include, without limitation, Northern blot analysis of tissue samples obtained from the animal, in situ hybridization analysis, Western analysis (immunoblot analysis), immunoassays such as enzyme-linked immunosorbent assays, and reverse-transcriptase PCR (RT-PCR).

It will be understood that the present disclosure also provides tissues (e.g., skin, eye, fat, muscle, lung, heart, bone, liver, intestine, kidney, spleen, brain, cartilage, marrow, adrenal glands, ovaries, and testes) and cells or cell lines (e.g., fat cells, preadipocytes, skin or lung fibroblasts, muscle satellite cells, osteoblasts, bone marrow progenitor cells, neuronal progenitor cells, hepatocytes, endothelial cells, chondroblasts, and splenocytes cells) obtained from a transgenic nonhuman animal provided herein.

Polypeptide sequences and the encoding polynucleotide sequences for proteins, protein domains and fragments thereof, for proteins described herein such as HSV thymidine kinase (TK) polypeptides, FK506 binding protein (FKBP) and domains thereof, caspase(s) and domains thereof, the detectable fluorescent, bioluminescent polypeptides that are described herein include natural and recombinantly engineered variants. These variants retain the function and biological activity (including enzymatic activities if applicable) associated with the parent (or wildtype) protein. Conservative substitutions of amino acids are well known and may occur naturally in the polypeptide (e.g., naturally occurring genetic variants) or may be introduced when the polypeptide is recombinantly produced. Amino acid substitutions, deletions, and additions may be introduced into a polypeptide using well-known and routinely practiced mutagenesis methods (see, e.g., Sambrook et al. *Molecular Cloning: A Laboratory Manual,* 3d ed., Cold Spring Harbor Laboratory Press, NY 2001)). Oligonucleotide-directed site-specific (or segment specific) mutagenesis procedures may be employed to provide an altered polynucleotide that has particular codons altered according to the substitution, deletion, or insertion desired. Deletion or truncation variants of proteins may also be constructed by using convenient restriction endonuclease sites adjacent to the desired deletion. Alternatively, random mutagenesis techniques, such as alanine scanning mutagenesis, error prone polymerase chain reaction mutagenesis, and oligonucleotide-directed mutagenesis may be used to prepare polypeptide variants (see, e.g., Sambrook et al., supra).

Differences between a wild type (or parent) polynucleotide or polypeptide and the variant thereof, may be determined by methods routinely practiced in the art to determine identity, which are designed to give the greatest match between the sequences tested. Methods to determine sequence identity can be applied from publicly available computer programs. Computer program methods to determine identity between two sequences include, for example, BLASTP, BLASTN (Altschul, S. F. et al., *J. Mol. Biol.* 215: 403-410 (1990), and FASTA (Pearson and Lipman Proc. Natl. Acad. Sci. USA 85; 2444-2448 (1988). The BLAST family of programs is publicly available from NCBI and other sources (*BLAST Manual,* Altschul, S., et al., NCBI NLM NIH Bethesda, Md.

Assays for determining whether a polypeptide variant folds into a conformation comparable to the non-variant polypeptide or fragment include, for example, the ability of the protein to react with mono- or polyclonal antibodies that are specific for native or unfolded epitopes, the retention of ligand-binding functions, the retention of enzymatic activity (if applicable), and the sensitivity or resistance of the mutant protein to digestion with proteases (see Sambrook et al., supra). Polypeptides, variants and fragments thereof, can be prepared without altering a biological activity of the resulting protein molecule (i.e., without altering one or more functional activities in a statistically significant or biologically significant manner). For example, such substitutions are generally made by interchanging an amino acid with another amino acid that is included within the same group, such as the group of polar residues, charged residues, hydrophobic residues, and/or small residues, and the like. The effect of any amino acid substitution may be determined empirically merely by testing the resulting modified protein for the ability to function in a biological assay, or to bind to a cognate ligand or target molecule.

Non-Human Animals Models for Aging, Age-Related Disorders and Age-Sensitive Traits Caused by Senescence-Inducing Stimuli The present disclosure provides transgenic non-human animal models of aging, which exhibit, for example, age-related phenotypes, age-related disorders, age-sensitive traits, and the like, wherein the animals comprise a transgene that allows for the selective and controllable ablation of senescent cells. The animal models are particularly advantageous for determining the contribution of senescence-inducing stimuli to age-related health parameters and for treating the deleterious effects that result from such stimuli.

A non-human animal model of the disclosure exhibits features of an age-related phenotype, age-related disorder or age-sensitive trait at least in part as a result of contact with a senescence-inducing stimulus. Exemplary features of an age-related phenotype, age-related disorder or age-sensitive trait will be apparent in light of the present disclosure.

In certain specific embodiments, for example, an age-sensitive trait evaluated in the context of the animal models is selected from one or more of T cell subset distribution, cataract formation, spontaneous activity, motor coordination and cognitive capacity, physical function, body composition (e.g., sarcopenia, osteoporosis, loss of fat mass, adipose tissue loss, adipocyte cell size) and cardiac function. Still other illustrative age-sensitive traits can be measured using tissues and organs of test and control mice, including fiber diameter analysis on muscle (e.g., gastrocnemius muscle, abdominal muscle), DNA damage analysis, analysis of renal and glomerulosclerosis, analysis for retinal atrophy, proteotoxic stress analysis, oxidative stress analysis, analysis of the hematopoietic system, and the like.

These exemplary age-sensitive traits can be assessed using standard techniques known and available in the art. Spontaneous activity of individual mice can be measured, for example, over a 48-hour period using comprehensive laboratory animal monitoring systems equipped with photocells (e.g., Columbus Instruments) as previously described (e.g., Handschin et al., J. Biol. Chem., Vol. 282, 41, 30014, Oct. 12, 2007; Pack et al., Physiol. Genomics (Sep. 19, 2006)). Motor coordination can be analyzed, for example, by performing an accelerating rotarod test. For measuring cognitive capacity, a modified Stone T-maze, which is sensitive to age-related changes in learning and memory, can be used. Physical function can be assessed, for example, by measuring running time, distance and work using a motorized treadmill, and grip strength using a grip meter, according to previously described protocols (e.g., Zhang et al., Animal Models of Inflammatory Pain Neuromethods, Volume 49, Oct. 20, 2010, 23-40; Balkaya et al., Behavioral Testing in Mouse Models of Stroke, Neuromethods, Volume 47, 2010, 179-197). Lean mass, fat mass and bone mineral density can be assessed, for example, by QNMR and/or dual-energy X-ray absorptiometry measurements as previously described (e.g., Reed et al., Physiology & Behavior, Vol. 91, 2007, 593-600; Halldorsdottir et al., Int. J. Body Compos. Res., 2009; 7(4), 147-154; Brommage et al., AJP—Endo, Sep. 1, 2003, Vol. 285, No. 3 E454-E459).

These and other methods for detecting, monitoring or quantifying age-related phenotypes associated with senescence-inducing stimuli will be apparent in light of the present disclosure, such as histological studies, molecular studies, biochemical studies, cognitive studies, behavioral assessment, and others. Exemplary methods are also provided in the examples of the present disclosure.

A senescence-inducing stimulus may include, for example, one or more of a chemical stimulus, an environmental stimulus, a genetic modification, a diet modification, or a combination thereof. In certain specific embodiments, the senescence-inducing stimulus comprises irradiation treatment or treatment with one or more chemotherapeutic agents. In certain more specific embodiments, the chemotherapeutic agents are illustratively selected from doxorubicin, taxol, docetaxel, gemcitabine, or cisplatin. In other embodiments, the senescence-inducing stimulus is cigarette smoking or exposure to cigarette smoke or other environmental insults.

An animal comprising a transgene selectively expressed in senescent cells may be exposed to one or more senescence-inducing stimuli (e.g., radiation or chemotherapy) at any desired points in time.

The aging process in an animal model, or the induction of an age-related disorder or age-sensitive trait, can be manipulated by any desired means. For example, a non-human animal model as described herein may be a multi-transgenic model comprising, in addition to a first transgene selectively expressed in senescent cells, a second transgene which expressed a gene product that contributes to a desired age-related phenotype (i.e., a transgenic aging model) or having reduced or abrogated expression of an endogenous gene (i.e., gene knockout aging model), or a combination thereof, which results in or contributes to an age-related phenotype, including an age-related disorder or age-sensitive trait, in the animal. Alternatively, a non-human animal model as described herein may contain one or more naturally occurring mutations that result in or contribute to an age-related phenotype of interest. As such, the effects of senescence-inducing stimuli on the age-related phenotype of the animals can be advantageously determined.

In one embodiment, to create an animal model as described herein, a transgenic parent animal comprising a transgene selectively expressed by senescent cell (for convenience, referred to as a "first transgenic animal") and a genetically modified model parent animal, e.g., which develops a desired age-related phenotype (for convenience, referred to as a "second genetically modified parent animal") may be crossed (or bred) with each other. A transgenic animal comprising a transgene selectively expressed by a senescent cell may be any transgenic animal that comprises a senescent cell-specific promoter within a transgene that selectively drives expression of a polypeptide encoded by the transgene in senescent cells. In certain embodiments, a first transgenic parent animal comprises a transgene comprising p16$^{Ink4a}$ promoter operatively linked to a polynucleotide sequence encoding a FKBP-caspase fusion polypeptide (p16-FKBP-caspase transgene), and to a polynucleotide sequence encoding a green fluorescent protein; or a p16$^{Ink4a}$ promoter operatively linked to a polynucleotide sequence encoding a fusion polypeptide comprising a luciferase, a red fluorescent protein, and a truncated herpes simplex virus thymidine kinase (p16-3MR transgene). In other embodiments, a parent animal comprises a transgene comprising a p16$^{Ink4a}$ promoter in frame to express an at least one FKBP domain and at least one caspase domain (e.g., FKBP-caspase fusion polypeptide described herein) and comprises the p16-3MR transgene described herein. In still another embodiment, a parent animal comprises a transgene comprising a p16$^{Ink4a}$ promoter in frame to express a at least one FKBP domain and at least one caspase domain (e.g., FKBP-caspase fusion polypeptide described herein) or the transgene comprises the p16-3MR transgene described herein, and which parent animal has a BubR1 hypomorphic (BubR1H/H) genetic background (see, e.g., Baker et al., Nature 479:232-236 (2011); International Application Publication No. WO 2012/177927). The second genetically modified parent animal may be an animal that develops an age-related phenotype (e.g., transgenic or knockout models that develop an age-related phenotype). F1 progeny from a cross between these parental animals are multi-transgenic animals which express the transgenes from each parent. Additional crosses for selection of progeny with heterozygous or homozygous knockout genes may be necessary.

In an alternative embodiment, a multi-transgenic model may be derived by directly introducing a transgene into the germline of another genetically modified animal. For example, a transgene selectively expressed by senescent cells (e.g., p16-3MR transgene) may be injected into single cell embryos harvested from a genetically modified transgenic mouse model. A person having skill in the art will understand that various injection/recipient embryo combinations may be employed to create a multi-transgenic animal model. Co-injection of different transgenes for generating multi-transgenic mice can be accomplished by these and other methods routinely practiced in the art (see, e.g., Oddo et al., 2003, Neuron 39:409-421; U.S. Pat. No. 7,479,579).

Non-human animal models with senescent cell specific transgene expression created by cross-breeding, transgene injection, or other methods may be confirmed for genotype or transgene expression. Resulting offspring may be genotyped by Southern blot analysis or PCR techniques on DNA extracted from tissue samples (e.g., tail tips or ear punches) using transgene specific probes or primers, respectively. The level of mRNA expression of the transgenes in tissues of transgenic animals may also be assessed using techniques including Northern blot analysis, in situ hybridization, RT-PCR, or real-time PCR. Transgenic proteins may also be detected in tissue samples from transgenic animals using antibodies specific for a polypeptide expressed by the transgene and/or antibodies that are specific for a detectable label that is co-expressed by the transgene, for example.

In another embodiment, for producing the animal model described herein, a knock out or knock-down animal (e.g., which develops an age-related phenotype of interest) may be crossed with a transgenic animal that expresses a senescent cell specific transgene. Gene knock-outs allow assessment of in vivo function of a gene which has been altered and used to replace a normal copy. Knock-out modifications include insertion of mutant stop codons, deletion of DNA sequences, or inclusion of recombination elements (lox p sites) recognized by enzymes such as Cre recombinase. Cre-lox system allows for the ablation of a given gene or the ablation of a certain portion of gene sequence. To create a transgenic animal, an altered version of a gene of interest (e.g., a human age-related gene or a gene encoding a senescent cell associated polypeptide) can be inserted into an animal germ line using standard techniques of oocyte microinjection or transfection, or microinjection into stem cells. For oocyte injection, one or more copies of the altered/mutated gene of interest (e.g., human age-related gene) can be inserted into the pronucleus of a just-fertilized oocyte. The oocyte is then re-implanted into a pseudo-pregnant foster mother. The liveborn progeny can be screened for transgene integrants by analyzing the DNA from tissue samples. Retroviral infection of early embryos may also be performed to insert the altered gene. Embryos are infected during early stages of development to generate a chimera, some of which will lead to germline transmission. Alternatively, if it is desired to inactivate or replace the endogenous gene, mutant alleles may be introduced by homologous recombination into embryonic stem cells. Embryonic stem cells containing a knock out mutation in one allele of the gene being studied are introduced into early embryos. The resultant progeny are chimeras containing tissues derived from both the transplanted ES cells and host cells. Chimeric animals may be mated to assess whether the mutation is incorporated into the germ line. Chimeric animals that are each heterozygous for the knock-out mutation are mated to produce homozygous knock out animals. Mutations in the mouse germline may also be created by injecting oligonucleotides containing the mutation of interest. Gene knock down uses RNAi technology to repress endogenous gene expression in vivo or in vitro. Lentiviral vectors expressing siRNAs or shRNAs may be used to transduce preimplantation mouse embryos for silencing of their specific target genes (see e.g., Tiscornia et al., 2003, Proc. Natl. Acad. Sci. USA 100:1844-1848; Singer et al., Nature Protocols 1:286-292; Szulc et al., 2006, Nature Methods 3:109-116).

Transgenic non-human animal models may comprise at least a second transgene associated with an age-related phenotype or disorder, in addition to the first transgene selectively expressed by senescent cells. The expression of the second transgene will generally alter one or more age-related phenotype or age-sensitive trait in the animal.

Gene knock out models for aging are known in the art and may comprise heterozygous or homozygous mutation of a gene associated with aging to reduce or abrogate expression of the gene. The reduction or abrogation of the gene associated with aging will generally result in or contributes to one or more age-related phenotype or disorder, or will modulate one or more age-sensitive traits.

Animal models of aging (including transgenic models, knockout models, and models having naturally occurring gene modifications) have been reviewed (e.g., Exp Mol Pathol. 2002 February; 72(1):49-55; ILAR J. 2011 Feb. 8; 52(1):4-15; and elsewhere, each of the review articles as well as the references cited therein is incorporated herein by reference in its entirety).

Additionally, many transgenic/knockout mouse lines and information about mouse models of aging are available from the Jackson Laboratory (Bar Harbor, Me.).

In certain embodiments, the present disclosure provides for an animal model comprising a $p16^{Ink4a}$ promoter, or an operable truncation thereof, operatively linked to a polynucleotide sequence encoding a FKBP-caspase fusion polypeptide (p16-FKBP-caspase transgene), and to a polynucleotide sequence encoding a green fluorescent protein; or a $p16^{Ink4a}$ promoter operatively linked to a polynucleotide sequence encoding a fusion polypeptide comprising a luciferase, a red fluorescent protein, and a truncated herpes simplex virus thymidine kinase (p16-3MR transgene); wherein the model further comprises a second transgene associated with aging (e.g., one that gives rise to or contributes to an age-related phenotype, age-related disorder and/or age-sensitive trait).

In yet another embodiment, the present disclosure provides for a method of producing a non-human animal model for aging comprising a non-human animal that exhibits an age-related phenotype and comprises a transgene selectively expressed by senescent cells, wherein the method comprises (a) providing an animal comprising the transgene selectively expressed by senescent cells; and (b) breeding the animal of step (a) with an animal comprising a genetic modification associated with an age-related phenotype to produce a multi-transgenic animal. An animal comprising a genetic modification associated with an age-related phenotype may be a knockout, knockdown, or transgenic animal. In a specific embodiment, the method may further comprise administering to, or exposing the animal to, for example, a chemical stimulus, whole body irradiation, an environmental stimulus, a diet modification, or another stimulus, to produce or facilitate an age-related phenotype.

Non-human animal models for aging with senescent cell specific transgene expression, as described herein, are useful in tracking or monitoring senescence cells. For example, animal models comprising transgenes expressing detectable labels may be used in imaging senescent cells, determining ratio of senescent cells in a tissue, and/or monitoring the elimination of senescent cells. In addition, such models may also be used in characterizing drug candidates for treating or preventing development of an age-related disorder or age-sensitive trait, such as the tissue specificity of such candidates. For example, these models expressing detectable labels under the control of senescent cell-specific promoters may be used to determine the tissue type in which a drug candidate suppresses cellular senescence using the detectable labels. Animal models comprising transgenes expressing cytotoxicity-activating molecules allow for titrating the elimination of senescent cells by modulating concentrations of activating agents. In yet another embodiment, the present disclosure provides for a method of producing a non-human animal model for aging comprising a non-human animal that exhibits an age-related phenotype and comprises a transgene selectively expressed by senescent cells, wherein the method comprises (a) providing an animal comprising the transgene selectively expressed by senescent cells; and (b) administering a senescence-inducing stimulus.

Non-human animal models for aging with senescent cell specific transgene expression, as described herein, may be used to evaluate effects of senescent cell ablation on an age-related phenotype. By eliminating senescent cells or effects of senescent cell associated molecules from the animal at various times in an animal model for aging, the role of senescent cells in vivo on an age-related phenotype, particularly an age-related phenotype associated at least in part with senescence-inducing stimuli, may be tested. In certain embodiments, senescent cell ablation may be accomplished by administration of FK1012 analog AP20187, which induces dimerization of membrane-bound myristolylated FKBP-caspase fusion protein expressed in senescent cells via the p16$^{Ink4a}$ promoter, resulting in activation of apoptosis. Senescent cell ablation may also be performed by candidate therapeutic agents. In certain other embodiments, senescent cell ablation may be accomplished by administration of the pro-drug ganciclovir (GCV), which is converted to a cytotoxic moiety by a truncated herpes simplex virus thymidine kinase expressed in senescent cells via the p16$^{Ink4a}$ promoter.

In certain embodiments, also provided herein are isolated cells and/or cell lines derived from the non-human animal models with senescent cell-specific transgene expression, as described herein. Primary cell cultures derived from the non-human animal models as described herein may be used. In certain embodiments, continuous cell lines are generated from the non-human animal models. Methods for deriving a continuous cell line from transgenic animals are known in the art (see, e.g., Small et al., 1985, Mol. Cell. Biol. 5:642-648; Morgan et al., 1994, Dev. Biol. 162:486-98; U.S. Pat. Nos. 5,814,716; 6,583,333; 6,825,394). Isolated cells or cell lines may be derived from any organ, tissue, or bodily fluid from the animal model, including, but not limited to the brain, cerebrospinal fluid, or spinal cord. The cells and cell lines may be cultured under conditions and in media appropriate to maintain the health and propagation of the cells, as desired, using techniques and procedures routinely practiced in the cell culture art. These isolated cells or cell lines may be used to identify and characterize therapeutic agents that suppress cellular senescence and that are useful for treating or preventing age-related phenotypes associated with senescence-inducing stimuli.

Methods for Identifying Therapeutic Agents

The non-human animal models and cell lines derived therefrom as described herein may be used to identify therapeutic agents effective for treating or preventing age-related disorders, and, more particularly, for treating or preventing the deleterious age-related health effects caused by various senescence-inducing stimuli, such as radiation or chemotherapy treatment. Such animal models and cell lines are particularly useful for identifying therapeutic agents effective for treating or preventing age-related disorders via suppressing cellular senescence. Therapeutic agents include small molecules, antibodies, antigen-binding fragments, polypeptides, peptides, peptibodies, hormones, and nucleic acids.

In one embodiment, the present disclosure provides a method for identifying a therapeutic agent effective for treating or preventing the development of an age-related disorder or age-sensitive trait, comprising: (a) administering a candidate therapeutic agent to the animal of the animal model provided herein to provide a treated animal; and (b) determining the level of suppression of cellular senescence in the treated animal and comparing to the level of cellular senescence in the untreated control animal; wherein suppression of cellular senescence in the treated animal compared with the untreated animal identifies an agent effective for treating or preventing the age-related disorder or age-sensitive trait.

In a related embodiment, the present disclosure provides a method for identifying a therapeutic agent effective for treating or preventing the development of an age-related disorder or age-sensitive trait, comprising: (a) administering a candidate therapeutic agent to the animal of the animal model provided herein to provide a treated animal; and (b) (1) determining the phenotype of the development of an age-related disorder or age-sensitive trait exhibited in the treated animal, and comparing to the phenotype of the development of an age-related disorder or age-sensitive trait exhibited in an untreated control model animal, and (2) determining the level of suppression of cellular senescence in the treated animal and comparing to the level of cellular senescence in the untreated control animal; wherein (1) suppression of one or more age-related disorder or age-sensitive traits and (2) suppression of cellular senescence in the treated animal compared with the untreated animal identifies an agent effective for treating or preventing the development of an age-related disorder or age-sensitive trait.

Candidate therapeutic agents include any agents that are potentially capable of treating or preventing one or more age-related disorder or age-sensitive trait, such as small molecules, antibodies, polypeptides, peptides, hormones, and nucleic acids. Potential therapeutic agents may be identified from "libraries" or collections of compounds, compositions, or molecules. A source of small molecules, peptides, and oligonucleotides includes combinatorial libraries that may be screened to identify a therapeutic agent useful for treating of preventing an age-related disorder or age-sensitive trait. Other exemplary libraries comprise peptides or polypeptides that represent a complementarity determining region (CDR) of an antibody.

Candidate therapeutic agents may be administered to the animal of the animal model provided herein before, concurrently or after onset of an age-related disorder or age-sensitive trait. The onset of an age-related disorder or age-sensitive trait may be triggered by inducing the expression of an inducible transgene that is associated with an age-related disorder or age-sensitive trait, such as by chemical or mechanical induction, by radiation, or by diet manipulation.

A person skilled in the art will also readily appreciate that when performing analyses in animal models, appropriate controls are included. By way of non-limiting example, a group of animals will receive a candidate therapeutic agent (or a composition or a vehicle comprising the agent), which animals may be referred to as treated animals. Another group of animals will receive vehicle only or another appropriate control composition that does not include an agent effective in treating or preventing an age-related disorder or age-sensitive trait. In certain embodiments, a group of animals is treated with a agent known as effective in treating or preventing an age-related disorder or age-sensitive trait as a positive control. The phenotype (or one or more phenotypic markers or characteristics) of the treated animal is then compared with the phenotype of the control animals that do not receive the candidate agent.

For these embodiments, a group of animals may receive a therapeutic agent known to be effective in treating or preventing an age-related disorder or age-sensitive trait by suppressing cellular senescence to be used as a positive control group. Additional positive controls include the animal models provided herein that comprise a transgene that includes a senescent cell specific promoter that is operatively linked to a polypeptide (which may be a fusion polypeptide) comprising a cytotoxicity-activating molecule (e.g., HSV truncated TK, FKBP-caspase polypeptide).

Accordingly, when cells are induced to senescence by normal aging or by any one of the molecules, methods, or genetic modifications described herein, the fusion polypeptide expresses the cytotoxicity-activating molecule. By way of example, a positive control animal model group that expresses the FKBP-caspase polypeptide (e.g., an INK-ATTAC animal (see Baker et al., Nature 479:232-36 (2011)) may be treated with AP20187 and related analogs, for example, which results in senescent cell destruction. By way of additional example, a transgenic animal (e.g., a P16-3MR animal) that expresses a fusion polypeptide comprising HSV truncated TK can be administered a prodrug, such as ganciclovir, that is activated when the truncated thymidine kinase is expressed in senescent cells, resulting in destruction of the senescent cell.

Suppressing cellular senescence may comprise one or both of (1) selectively destroying or facilitating selective destruction of a senescent cell; and (2) inhibiting expression or secretion of one or more senescence cell-associated molecules including senescence-cell associated polypeptides (e.g., cytokines, chemokines, growth factors) by the senescent cell.

Determining the effectiveness of a therapeutic agent or a candidate therapeutic agent to inhibit induction or progression of an age-related disorder or age-sensitive trait or to suppress senescence as described herein in an animal model is typically performed using one or more statistical analyses with which a skilled person will be familiar. By way of example, statistical analyses such as two-way analysis of variance (ANOVA) may be used for determining the statistical significance of differences between animal groups treated with an agent and those that are not treated with the agent (i.e., negative control group). Statistical packages such as SPSS, MINITAB, SAS, Statistika, Graphpad, GLIM, Genstat, and BMDP are readily available and routinely used by a person skilled in the animal art.

Cellular senescence is a stable and essentially permanent arrest of cell proliferation, which is accompanied by extensive changes in gene expression. Many types of cells, both normal cells and tumor cells, undergo senescence in response to stress. As described in the art, the phenotype of a senescence cell, such as the phenotype referred to as senescence associated secretory phenotype (SASP), is typified by secretion of numerous cytokines (e.g., inflammatory cytokines), growth factors, extracellular matrix components (ECM) and ECM-degrading enzymes, and proteases, for example. While proliferative arrest poses a formidable barrier to tumor progression (see, e.g., Campisi, *Curr. Opin. Genet. Dev.* 21:107-12 (2011); Campisi, *Trends Cell Biol.* 11:S27-31 (2001); Prieur et al., *Curr. Opin. Cell Biol.* 20:150-55 (2008)), and molecules secreted by senescent cells can stimulate tissue repair (see, e.g., Adams, *Molec. Cell* 36:2-14 (2009); Rodier et al., *J. Cell Biol.* 192:547-56 (2011)), senescent cells also secrete molecules that can cause inflammation (see, e.g., Freund et al., *Trends Mol. Med.* 16:238-46 (2010); Davalos et al., *Cancer Metastasis Rev.* 29:273-83 (2010)). Low-level, chronic inflammation is a hallmark of aging tissues, and inflammation is a major cause of, or contributor to, virtually every major age-related pathology, including cancer (Ferrucci et al., 2004, *Aging Clin. Exp. Res.* 16:240-243; Franceschi et al., 2007, Mech. Ageing Dev. 128:192-105; Chung et al., 2009, *Ageing Res. Rev.* 8:18-30; Davalos et al., 2010, *Cancer Metastasis Rev.* 29:273-283; Freund et al., 2010, *Trends Molec. Med.* 16:238-248). Thus, senescent cells, which increase with age and at sites of age-related pathology, might stimulate local chronic inflammation and tissue remodeling, thereby fueling both the degenerative diseases of aging as well as age-related cancer.

A senescent cell may exhibit any one or more of the following characteristics. (1) Senescence growth arrest is essentially permanent and cannot be reversed by known physiological stimuli. (2) Senescent cells increase in size, sometimes enlarging more than twofold relative to the size of non-senescent counterparts. (3) Senescent cells express a senescence-associated β-galactosidase (SA-β-gal), which partly reflects the increase in lysosomal mass. (4) As described herein, most senescent cells express p16INK4a, which is not commonly expressed by quiescent or terminally differentiated cells. (5) Cells that senesce with persistent DNA damage response signaling harbor persistent nuclear foci, termed DNA segments with chromatin alterations reinforcing senescence (DNA-SCARS). These foci contain activated DDR proteins and are distinguishable from transient damage foci. DNA-SCARS include dysfunctional telomeres or telomere dysfunction-induced foci (TIF). (6) Senescent cells express and may secrete molecules called herein senescent cell-associated molecules, which in certain instances may be dependent on persistent DDR signaling for their expression. (7) The nuclei of senescent cells lose structural proteins such as Lamin B1 or chromatin-associated proteins such as histones and HMGB1. See, e.g., Freund et al., *Mol. Biol. Cell* 23:2066-75 (2012); Davalos et al., *J. Cell Biol.* 201:613-29 (2013); Ivanov et al., *J. Cell Biol.* DOI: 10.1083/jcb.201212110, page 1-15; published online Jul. 1, 2013; Funayama et al., *J. Cell Biol.* 175:869-80 (2006)).

Senescent cell-associated molecules include growth factors, proteases, cytokines (e.g., inflammatory cytokines), chemokines, cell-related metabolites, reactive oxygen species (e.g., $H_2O_2$), and other molecules that stimulate inflammation and/or other biological effects or reactions that may promote or exacerbate the underlying disease of the subject. Senescent cell-associated molecules include those that are described in the art as comprising the senescence-associated secretory phenotype (SASP), senescent-messaging secretome, and DNA damage secretory program (DDSP). These groupings of senescent cell associated molecules, as described in the art, contain molecules in common and are not intended to describe three separate distinct groupings of molecules. Senescent cell-associated molecules include certain expressed and secreted growth factors, proteases, cytokines, and other factors that may have potent autocrine and paracrine activities. Without wishing to be bound by theory, the negative effects of senescent cells are believed to be the result of, at least in part, the secretion of pro-inflammatory cytokines, chemokines, growth factors, and proteases that comprise the SASP of a senescent cell (see, e.g., Coppe et al., PLoS Biol. 6:2853-68 (2008)). Senescent cell-associated molecules that comprise the SASP can disrupt normal tissue structure and function and stimulate malignant phenotypes in pre-malignant or non-aggressive cancer cells (see, e.g., Coppe et al., supra; Coppe et al. *J. Biol. Chem.* 281:29568-74 (2006); Coppe et al. *PLoS One* 5:39188 (2010); Krtolica et al. *Proc. Natl. Acad. Sci. U.S.A.* 98:12072-77 (2001); Parrinello et al., *J. Cell Sci.* 118:485-96 (2005). ECM associated factors include inflammatory proteins and mediators of ECM remodeling and which are strongly induced in senescent cells (see, e.g., Kuilman et al., *Nature Reviews* 9:81-94 (2009)). Other senescent cell-associated molecules include extracellular polypeptides (proteins) described collectively as the DNA damage secretory program (DDSP) (see, e.g., Sun et al., *Nature Medicine* published online 5

Aug. 2012; doi:10.1038/nm.2890). Senescent cell-associated proteins also include cell surface proteins (or receptors) that are expressed on senescent cells, which include proteins that are present at a detectably lower amount or are not present on the cell surface of a non-senescent cell.

Senescence cell-associated molecules include secreted factors which may make up the pro-inflammatory phenotype of a senescent cell (e.g., SASP). These factors include, without limitation, GM-CSF, GROα, GROα,β,γ, IGFBP-7, IL-1α, IL-6, IL-7, IL-8, MCP-1, MCP-2, MIP-1α, MMP-1, MMP-10, MMP-3, Amphiregulin, ENA-78, Eotaxin-3, GCP-2, GITR, HGF, ICAM-1, IGFBP-2, IGFBP-4, IGFBP-5, IGFBP-6, IL-13, IL-1β, MCP-4, MIF, MIP-3α, MMP-12, MMP-13, MMP-14, NAP2, Oncostatin M, osteoprotegerin, PIGF, RANTES, sgp130, TIMP-2, TRAIL-R3, Acrp30, angiogenin, Ax1, bFGF, BLC, BTC, CTACK, EGF-R, Fas, FGF-7, G-CSF, GDNF, HCC-4, 1-309, IFN-γ, IGFBP-1, IGFBP-3, IL-1 R1, IL-11, IL-15, IL-2R-α, IL-6 R, I-TAC, Leptin, LIF, MMP-2, MSP-a, PAI-1, PAI-2, PDGF-BB, SCF, SDF-1, sTNF RI, sTNF RII, Thrombopoietin, TIMP-1, tPA, uPA, uPAR, VEGF, MCP-3, IGF-1, TGF-β3, MIP-1-delta, IL-4, FGF-7, PDGF-BB, IL-16, BMP-4, MDC, MCP-4, IL-10, TIMP-1, Flt-3 Ligand, ICAM-1, Ax1, CNTF, INF-γ, EGF, BMP-6. Cell-associated molecules also include those sometimes referred to in the art as senescence messaging secretome (SMS) factors, some of which are included in the listing of SASP polypeptides, include without limitation, IGF1, IGF2, and IGF2R, IGFBP3, IDFBP5, IGFBP7, PA11, TGF-β, WNT2, IL-1α, IL-6, IL-8, and CXCR2-binding chemokines. Factors, including those referred to in the art, include without limitation the factors described in Sun et al., *Nature Medicine*, supra, including, for example, products of the genes, MMP1, WNT16B, SFRP2, MMP12, SPINK1, MMP10, ENPP5, EREG, BMP6, ANGPTL4, CSGALNACT, CCL26, AREG, ANGPT1, CCK, THBD, CXCL14, NOV, GAL, NPPC, FAM150B, CST1, GDNF, MUCL1, NPTX2, TMEM155, EDN1, PSG9, ADAMTS3, CD24, PPBP, CXCL3, MMP3, CST2, PSG8, PCOLCE2, PSG7, TNFSF15, C17orf67, CALCA, FGF18, IL8, BMP2, MATN3, TFP1, SERPINI 1, TNFRSF25, and IL23A. Senescent cell-associated proteins also include cell surface proteins (or receptors) that are expressed on senescent cells, which include proteins that are present at a detectably lower amount or are not present on the cell surface of a non-senescent cell.

A therapeutic agent of interest includes an agent that selectively destroys or facilitates selective destruction of a senescent cell and/or in some manner is effective for inhibiting expression or secretion of a senescence cell-associated molecule, including a senescence cell-associated protein, or a protein that is present on the cell surface of a senescent cell. Therapeutic agents of interest also include agents that inhibit transcription or translation of a senescence cell-associated polypeptide (protein), or a protein that is present on the cell surface of a senescent cell. Such agents are useful for treating or preventing an age-related disorder or age-sensitive trait.

A therapeutic agent that "selectively" destroys or facilitates "selective" destruction of a senescent cell is an agent that preferentially (or to a greater degree) destroys or facilitates destruction or facilitates clearance of a senescent cell. In other words, the therapeutic agent destroys or facilitates destruction of a senescent cell in a biologically, clinically, and/or statistically significant manner compared with its capability to destroy or facilitate destruction of a non-senescent cell. By way of non-limiting example, the therapeutic agent may directly or indirectly kill a senescent cell by disrupting the integrity of the cell membrane; inhibiting one or more metabolic processes in the cell; enhancing or stimulating a signaling pathway that leads to apoptosis or necrosis of the senescent cell; disrupt transcription or translation of genes or proteins, respectively, necessary for cell survival; and/or binding to the senescent cell to facilitate clearance or removal of the cell, for example, clearance by immune cells. As described herein, the presence of senescent cells in the transgenic animals comprising a senescent cell specific promoter can be monitored and determined by expression or presence (or lack of expression or presence) of one or more detectable labels (e.g., a luciferase or fluorescent polypeptide) that is operatively linked to the promoter.

In particular embodiments, the level of transcription, expression, or secretion can be determined for one or more senescence cell-associated polypeptides. An effective therapeutic agent that suppresses cellular senescence reduces or inhibits expression, secretion, or production of a senescence cell-associated polypeptide in a statistically significant or biologically significant manner compared to the appropriate controls. Proteins that comprise senescence cell-associated molecules and methods for evaluating expression and secretion of SASP proteins are described in the art (see, e.g., Freund et al., *Trends Mol. Med.* 16:283-46 (2010) and references cited therein; Sun et al., *Nature Med.*, published online 5 Aug. 2012; doi: 10.1038/nm.2890). Senescent cells may also be detected by determining the presence and level of senescence-associated-β-galactosidase (SA-β-Gal). A decrease or reduction in the level of expression or secretion of one or more senescence cell-associated molecules (including senescence cell-associated polypeptides), SA-β-Gal, or reduction in the quantity of senescent cells and a suppression of one or more phenotypic markers of an age-related disorder or age-sensitive trait in the test animal compared with the control animal identifies a therapeutic agent.

Senescent cells and senescent cell associated molecules can be detected by techniques and procedures described in the art. For example, the presence of senescent cells in tissues can be analyzed by histochemistry or immunohistochemistry techniques that detect the senescence marker, SA-beta gal (SA-Bgal) (see, e.g., Dimri et al., Proc. Natl. Acad. Sci. USA 92: 9363-9367 (1995). The presence of the senescent cell-associated polypeptide p16 can be determined by any one of numerous immunochemistry methods practiced in the art, such as immunoblotting analysis. Expression of p16 mRNA in a cell can be measured by a variety of techniques practiced in the art including quantitative PCR. The presence and level of senescence cell associated polypeptides (e.g., polypeptides of the SASP) can be determined by using automated and high throughput assays, such as an automated Luminex array assay described in the art (see, e.g., Coppe et al., *PLoS Biol* 6: 2853-68 (2008)). For monitoring a DNA damage response, the various DNA damage response indicators can be detected according to the method of Rodier et al., *Nature Cell Biol* 11: 973-979 (2009)).

Therapeutic agents of interest include those that are activated or that are pro-drugs which are converted to the active form by enzymes that are expressed at a higher level in senescent cells than in non-senescent cells. Other therapeutic agents of interest include those that bind to proteins on the cell surface of a cell that are present exclusively or at a greater level on senescent cells compared with non-senescent cells (see, e.g., International Patent Application Publication No. WO 2009/085216). In certain embodiments, a therapeutic agent that specifically binds to a senescent cell has at least 2, 4, 8, 10, 50, 100, or 1000 fold greater affinity for a senescent cell than for a non-senescent cell, or in certain embodiments, the therapeutic agent does not detectably bind to a non-senescent cell. A protein present at a greater level on a senescent cell than on a non-senescent cell may be a protein that is typically an intracellular protein and not detectable on the cell surface of a non-senescent cell. Other therapeutic agents of interest that suppress cellular senescence include those that are activated by a metabolic process that occurs more frequently or at a higher rate in senescent cells than in a non-senescent cell.

In one embodiment, therapeutic agents useful for treating or preventing age-related disorder or an age-sensitive trait are small organic molecules that suppress cellular senescence. A small molecule compound of interest may be further derivatized, either randomly or by SAR, to obtain compounds with improved anti-cellular senescence activity and more effective agents for treating an age-related disorder or age-sensitive trait. Small organic molecules typically have molecular weights less than $10^5$ daltons, less than $10^4$ daltons, or less than $10^3$ daltons.

A therapeutic agent includes an antibody, or antigen-binding fragment thereof, that specifically binds to a cognate antigen that is overly expressed, selectively expressed, or only expressed by senescent cell compared with a non-senescent, normal cell. The antibody may be an antibody that is internalized by the senescent cell via interaction with its cognate antigen. These specific antibodies may be polyclonal or monoclonal, prepared by immunization of animals and subsequent isolation of the antibody, or cloned from specific B cells according to methods and techniques routinely practiced in the art and described herein. A variable region or one or more complementarity determining regions (CDRs) may be identified and isolated from antigen-binding fragment or peptide libraries. An antibody, or antigen-binding fragment thereof, may be recombinantly engineered and/or recombinantly produced.

An antibody may belong to any immunoglobulin class, for example IgG, IgE, IgM, IgD, or IgA and may be obtained from or derived from an animal, for example, fowl (e.g., chicken) and mammals, which include but are not limited to a mouse, rat, hamster, rabbit, or other rodent, a cow, horse, sheep, goat, camel, human, or other primate. The antibody may be an internalising antibody. For use in human subjects, antibodies and antigen-binding fragments are typically human, humanized, or chimeric to reduce an immunogenic response by the subject to non-human peptides and polypeptide sequences.

Binding properties of an antibody to its cognate antigen may generally be determined and assessed using immunodetection methods including, for example, an enzyme-linked immunosorbent assay (ELISA), immunoprecipitation, immunoblotting, countercurrent immunoelectrophoresis, radioimmunoassays, dot blot assays, inhibition or competition assays, and the like, which may be readily performed by those having ordinary skill in the art (see, e.g., Harlow et al., *Antibodies: A Laboratory Manual*, Cold Spring Harbor Laboratory (1988)). As used herein, an antibody is said to be "immunospecific," "specific for" or to "specifically bind" to a cognate antigen if it reacts at a detectable level with the antigen or immunogen. Affinities of antibodies and antigen binding fragments thereof can be readily determined using conventional techniques, for example, those described by Scatchard et al. (*Ann. N.Y. Acad. Sci. USA* 51:660 (1949)) and by surface plasmon resonance (SPR; BIAcore™, Biosensor, Piscataway, N.J.).

The antibody may be a monoclonal antibody that is a human antibody, humanized antibody, chimeric antibody, bispecific antibody, or an antigen-binding fragment (e.g., $F(ab')_2$, Fab, Fab', Fv, and Fd) prepared or derived therefrom. An antigen-binding fragment may also be any synthetic or genetically engineered protein that acts like an antibody in that it binds to a specific antigen to form a complex. For example, antibody fragments include isolated fragments consisting of the light chain variable region, Fv fragments consisting of the variable regions of the heavy and light chains, recombinant single chain polypeptide molecules (scFv proteins), and minimal recognition units consisting of the amino acid residues that mimic the hypervariable region. In certain other embodiments, antibodies are multimeric antibody fragments such as miniantibodies, bispecific and bifunctional antibodies comprising a first Fv specific for an antigen associated with a second Fv having a different antigen specificity, and diabodies and the like. Useful methodologies are described generally, for example in Hayden et al., *Curr Opin. Immunol.* 9:201-12 (1997) and Coloma et al., *Nat. Biotechnol.* 15:159-63 (1997); U.S. Pat. No. 5,910,573); (Holliger et al., *Cancer Immunol. Immunother.* 45:128-30 (1997); Drakeman et al., *Expert Opin. Investig. Drugs* 6:1169-78 (1997); Koelemij et al., *J. Immunother.* 22:514-24 (1999); Marvin et al., *Acta Pharmacol. Sin.* 26:649-58 (2005); Das et al., *Methods Mol. Med.* 109:329-46 (2005)).

A minimal recognition unit or other antigen binding fragment may be identified from a peptide library. Such peptides may be identified and isolated from combinatorial libraries (see, e.g., International Patent Application Nos. PCT/US91/08694 and PCT/US91/04666) and from phage display peptide libraries (see, e.g., Scott et al., *Science* 249:386 (1990); Devlin et al., *Science* 249:404 (1990); Cwirla et al., *Science* 276: 1696-99 (1997); U.S. Pat. Nos. 5,223,409; 5,733,731; 5,498,530; 5,432,018; 5,338,665; 1994; 5,922,545; International Application Publication Nos. WO 96/40987 and WO 98/15833). A peptide that is a minimal recognition unit or a CDR (i.e., any one or more of three CDRs present in a heavy chain variable region and/or one or more of three CDRs present in a light chain variable region) may be identified by computer modeling techniques, which can be used for comparing and predicting a peptide sequence that will specifically bind to a polypeptide of interest as described herein (see, e.g., Bradley et al., *Science* 309:1868 (2005); Schueler-Furman et al., *Science* 310:638 (2005)).

Antibodies may generally be prepared by any of a variety of techniques known to persons having ordinary skill in the art. Immunogens used to immunize animals and/or to screen for antibodies of desired specificity include proteins isolated from senescent cells that, for example, are present on the cell surface of a senescent cell in greater quantity or having a different conformation than on a non-senescent cell; and senescent cell extracts, including outer membrane preparations, organelles isolated from senescent cells, and the like. Antibodies may also be identified and isolated from human immunoglobulin phage libraries, from rabbit immunoglobulin phage libraries, from mouse immunoglobulin phage libraries, and/or from chicken immunoglobulin phage libraries (see, e.g., Winter et al., *Annu. Rev. Immunol.* 12:433-55 (1994); Burton et al., *Adv. Immunol.* 57:191-280 (1994); U.S. Pat. No. 5,223,409; Huse et al., *Science* 246:1275-81 (1989); Schlebusch et al., *Hybridoma* 16:47-52 (1997) and references cited therein; Rader et al., *J. Biol. Chem.* 275: 13668-76 (2000); Popkov et al., *J. Mol. Biol.* 325:325-35 (2003); Andris-Widhopf et al., *J. Immunol. Methods* 242:

159-31 (2000)). Antibodies isolated from non-human species or non-human immunoglobulin libraries may be genetically engineered according to methods described herein and known in the art to "humanize" the antibody or fragment thereof.

Useful strategies for designing humanized antibodies may include, for example by way of illustration and not limitation, identification of human variable framework regions that are most homologous to the non-human framework regions of a chimeric antibody (see, e.g., Jones et al., *Nature* 321:522-25 (1986); Riechmann et al., *Nature* 332:323-27 (1988)). A humanized antibody may be designed to include CDR loop conformations and structural determinants of non-human variable regions, for example, by computer modeling, and then comparing the CDR loops and determinants to known human CDR loop structures and determinants (see, e.g., Padlan et al., *FASEB* 9:133-39 (1995); Chothia et al., *Nature,* 342:377-83 (1989)). Computer modeling may also be used to compare human structural templates selected by sequence homology with the non-human variable regions.

A therapeutic agent also includes a peptide-immunoglobulin (Ig) constant region fusion polypeptide, which includes a peptide-IgFc fusion polypeptide. The peptide may be any naturally occurring or recombinantly prepared molecule. A peptide-Ig constant region fusion polypeptide, such as a peptide-IgFc fusion polypeptide (also referred to in the art as a peptibody (see, e.g., U.S. Pat. No. 6,660,843)).

Therapeutic agents such as polypeptides, peptides, peptibodies, antibodies, and antigen binding fragments (i.e., peptides or polypeptides comprising at least one antibody V region) or other agents that specifically to a senescent cell can be linked to (i.e., conjugated to, fused to, or in some manner joined to or attached to) a second agent that selectively destroys or facilitates selective destruction of senescent cells. When delivered to the senescent cell by binding of the agent to the senescent cell, the cytotoxic moiety selectively destroys the senescent cell. If the agent is recombinantly produced, a nucleotide sequence encoding the cytotoxic moiety may be linked in frame to the agent and to one or more regulatory expression sequences to produce a fusion protein comprising the agent and cytotoxic moiety. Such second agents include cytotoxic molecules, including toxins derived from plants and microorganisms, as well as small molecules that do not selectively bind to senescent cells in the absence of being linked to the aforementioned antibody, polypeptide, or peptide.

In certain embodiments, a therapeutic agent is a polynucleotide or oligonucleotide that specifically hybridize to a portion of the genome or mRNA of a cell that is a senescent cell or that is in a disease microenvironment and may be induced to senescence by a cell damaging (i.e., biologically damaging) medical therapy. Polynucleotides and oligonucleotides are provided that are complementary to at least a portion of a nucleotide sequence encoding a senescent cellular polypeptide of interest (e.g., a short interfering nucleic acid, an antisense polynucleotide, a ribozyme, or a peptide nucleic acid) and that may be used to alter gene and/or protein expression. As described herein, these polynucleotides that specifically bind to or hybridize to nucleic acid molecules that encode a cellular polypeptide may be prepared using the nucleotide sequences available in the art. In another embodiment, nucleic acid molecules such as aptamers that are not sequence-specific may also be used to alter gene and/or protein expression.

Antisense polynucleotides bind in a sequence-specific manner to nucleic acids such as mRNA or DNA. Identification of oligonucleotides and ribozymes for use as antisense agents and identification of DNA encoding the genes for targeted delivery involve methods well known in the art. For example, the desirable properties, lengths, and other characteristics of such oligonucleotides are well known. Antisense technology can be used to control gene expression through interference with binding of polymerases, transcription factors, or other regulatory molecules (see Gee et al., In Huber and Carr, *Molecular and Immunologic Approaches*, Futura Publishing Co. (Mt. Kisco, N.Y.; 1994)).

Short interfering RNAs may be used for modulating (decreasing or inhibiting) the expression of a gene encoding a cellular polypeptide of interest. For example, small nucleic acid molecules, such as short interfering RNA (siRNA), micro-RNA (miRNA), and short hairpin RNA (shRNA) molecules may be used according to the methods described herein to modulate the expression of a cellular polypeptide of interest. A siRNA polynucleotide preferably comprises a double-stranded RNA (dsRNA) but may comprise a single-stranded RNA (see, e.g., Martinez et al. *Cell* 110:563-74 (2002)). A siRNA polynucleotide may comprise other naturally occurring, recombinant, or synthetic single-stranded or double-stranded polymers of nucleotides (ribonucleotides or deoxyribonucleotides or a combination of both) and/or nucleotide analogues as provided herein and known and used by persons skilled in the art.

In certain other embodiments, methods are provided herein for identifying a therapeutic agent that suppresses cellular senescence by using the animal models described herein. Candidate therapeutic agents may be administered to an animal of the animal model to provide a treated animal, followed by determining suppression of cellular senescence as described herein (i.e., determining the level or extent to which the candidate agent kills or facilitates killing of a senescent cell or determining the level of one or more senescence cell-associated molecules including senescence cell-associated polypeptides expressed or secreted by a senescent cell). The capability of the agent to suppress cellular senescence is determined by comparing the level or extent to which the candidate agent kills or facilitates killing of a senescent cell and/or comparing the level of one or more senescence cell-associated molecules such as senescence cell-associated proteins expressed or secreted by a senescent cell in the treated animal with an untreated (i.e., vehicle only or placebo) control animal. A statistically or biologically significant decrease or reduction of cellular senescence in the treated animal compared with untreated, control animal thereby identifies an agent that suppresses cellular senescence. As described herein, positive control animal groups (i.e., those that include an agent capable of destroying or facilitating destruction of a senescent cell or that inhibit or reduce expression or secretion of one or more senescence cell-associated including senescence cell-associated polypeptides) may also be included in such methods.

Also provided herein are methods for identifying a therapeutic agent for treating and/or preventing age-related disorders and age-specific traits associated with senescence-inducing stimuli, which employ primary cells from an animal model (e.g., an animal model mouse) or a cell line prepared from cells isolated from the animal model. In one embodiment, primary cells or a cell line derived from the animal model may be used in screening (including high throughput methods) for therapeutic agents that suppress cellular senescence. The cells may be exposed to, contacted, mixed with, or in some manner permitted to interact with an agent (e.g., a medical therapy) that induces cellular senescence prior to, concurrent with, or subsequent to contact with a candidate therapeutic agent. Suppression of cellular senescence may be determined by any of the methods described herein or in the art.

High throughput screening, typically automated screening, of a large number of candidate therapeutic agents from synthetic or natural product libraries may be used to identify therapeutic agents. The candidate therapeutic agents to be screened may be organized in a high throughput screening format such as using microfluidics-based devices, or a 96-well plate format, or other regular two dimensional array, such as a 384-well, 48-well or 24-well plate format, or an array of test tubes. The format is therefore amenable to automation. An automated apparatus that is under the control of a computer or other programmable controller may be used for one or more steps of the methods described herein. A controller may monitor the results of each step of the method and may automatically alter the testing paradigm in response to those results.

Pharmaceutical Compositions and Methods of Treatment

The present disclosure further provides for pharmaceutical compositions comprising any of the agents that suppress cellular senescence identified according to the methods described herein and a pharmaceutically acceptable excipient. The therapeutic agents described herein may be formulated in a pharmaceutical composition for use in treatment or preventive (or prophylactic) treatment (e.g., reducing the likelihood of occurrence, of exacerbation of disease, or occurrence or recurrence of one or more symptoms of the disease). The methods and excipients described herein are exemplary and are in no way limiting. Pharmaceutical acceptable excipients are well known in the pharmaceutical art and described, for example, in Rowe et al., Handbook of Pharmaceutical Excipients: A Comprehensive Guide to Uses, Properties, and Safety, 5$^{th}$ Ed., 2006, and in *Remington: The Science and Practice of Pharmacy* (Gennaro, 21$^{st}$ Ed. Mack Pub. Co., Easton, Pa. (2005)). Exemplary pharmaceutically acceptable excipients include sterile saline and phosphate buffered saline at physiological pH. Preservatives, stabilizers, dyes, buffers, and the like may be provided in the pharmaceutical composition. In addition, antioxidants and suspending agents may also be used.

The pharmaceutical compositions may be in the form of a solution. Alternatively, they may be in the form of a solid, such as powder, tablets, or the like.

The present disclosure also provides a method for treating or preventing age-related disorders and age-sensitive traits associated with senescence-inducing stimuli in a subject who has or who is at risk of developing an age-related disorder or age-sensitive trait associated with a senescence-inducing stimulus comprising administering a therapeutic agent that selectively suppresses cellular senescence in the subject, thereby treating or preventing an age-related disorder or age-sensitive trait associated with a senescence-inducing stimulus in the subject.

As understood by a person skilled in the medical art, the terms, "treat" and "treatment," refer to medical management of a disease, disorder, or condition of a subject (i.e., patient) (see, e.g., Stedman's Medical Dictionary). "Treating an age-related disorder or age-sensitive trait associated with a senescence-inducing stimulus" refers to reducing the number of symptoms of an age-related disorder or age-sensitive trait associated with a senescence-inducing stimulus, decreasing the severity of one or more symptoms, or delaying the progression of an age-related disorder or age-sensitive trait associated with a senescence-inducing stimulus.

"Preventing an age-related disorder or age-sensitive trait associated with a senescence-inducing stimulus" refers to preventing or delaying onset of an age-related disorder or age-sensitive trait associated with a senescence-inducing stimulus, or reoccurrence of one or more age-related disorder or age-sensitive trait associated with a senescence-inducing stimulus.

Subjects at risk of developing an age-related disorder or age-sensitive trait associated with a senescence-inducing stimulus include subjects exposed to conditions which induce senescence. For example, in specific embodiments, subjects at risk include those exposed to a senescence-inducing stimulus, such as a chemical stimulus, an environmental stimulus, a genetic modification, a diet modification, or a combination thereof. In certain more specific embodiments, the senescence-inducing stimulus comprises irradiation treatment (e.g., whole body treatment) or treatment with one or more chemotherapeutic agents (e.g., doxorubicin, taxol, docetaxel, gemcitabine, cisplatin, and the like). In other embodiments, the senescence-inducing stimulus comprises cigarette smoking, or exposure to cigarette smoke or other environmental insults.

The effectiveness of a therapeutic agent can readily be determined by a person skilled in the medical and clinical arts. One or any combination of diagnostic methods, including physical examination, assessment and monitoring of clinical symptoms, and performance of analytical tests and methods described herein, may be used for monitoring the health status of the subject. The effects of the treatment of a therapeutic agent or pharmaceutical composition can be analyzed using techniques known in the art, such as comparing symptoms of patients suffering from or at risk of an age-related disorder or age-sensitive trait that have received the treatment with those of patients without such a treatment or with placebo treatment.

In certain embodiments of the method for treating or preventing an age-related disorder or age-sensitive trait, the therapeutic agents are identified according to the screening methods provided herein. In certain other embodiments, the therapeutic agents may be other agents known in the art that selectively suppresses cellular senescence and that treat and/or prevent an age-related disorder or age-sensitive trait.

The therapeutic agents or pharmaceutical compositions that selectively suppress cellular senescence and that are useful for treating or preventing an age-related disorder or age-sensitive trait may be administered orally, topically, transdermally, parenterally, by inhalation spray, vaginally, rectally, or by intracranial injection, or any combination thereof. In one embodiment, the therapeutic agents or compositions comprising the agents are administered parenterally, such as via subcutaneous, intravenous, intramuscular, or intracisternal injection, or via infusion techniques.

The therapeutic agents or pharmaceutical compositions that selectively suppress cellular senescence provided herein are administered to a subject who has or is at risk of developing an age-related disorder or age-sensitive trait associated with a senescence-inducing stimulus at a therapeutically effective dose. A "therapeutically effective dose" of a specific therapeutic agent refers to that amount of the agent sufficient to result in reducing the severity of, eliminating, or delaying the onset or reoccurrence of one or more symptoms of an age-related disorder or age-sensitive trait in a statistically significant manner. Such a dose may be determined or adjusted depending on various factors including the specific therapeutic agents or pharmaceutical compositions, the routes of administration, the subject's condition, that is, stage of the disease, severity of symptoms caused by the disease, general health status, as well as age, gender, and weight, and other factors apparent to a person skilled in the medical art. Similarly, the dose of the therapeutic for treating a disease or disorder may be determined according to parameters understood by a person skilled in the medical art. Optimal doses may generally be determined using experimental models and/or clinical trials. Design and execution of pre-clinical and clinical studies for a therapeutic agent (including when administered for prophylactic benefit) described herein are well within the skill of a person skilled in the relevant art. The optimal dose of a therapeutic may depend upon the body mass, weight, or blood volume of the subject. For example, an amount between 0.01 mg/kg and 1000 mg/kg (e.g., about 0.1 to 1 mg/kg, about 1 to 10 mg/kg, about 10-50 mg/kg, about 50-100 mg/kg, about 100-500 mg/kg, or about 500-1000 mg/kg) body weight (which can be administered as a single dose, daily, weekly, monthly, or at any appropriate interval) of a therapeutic agent may be administered.

Also contemplated is the administration of a therapeutic agent or a pharmaceutical composition that selectively suppresses cellular senescence in combination with a second agent useful in treating or preventing an age-related disorder or age-sensitive trait.

In certain embodiments, a therapeutic agent that selectively suppresses cellular senescence and a second agent useful in treating or preventing an age-related disorder or age-sensitive trait act synergistically. In other words, these two agents interact such that the combined effect of the agents is greater than the sum of the individual effects of each agent when administered alone.

In certain other embodiments, a therapeutic agent that selectively suppresses cellular senescence and a second agent useful in treating or preventing an age-related disorder or age-sensitive trait act additively. In other words, these two agents interact such that the combined effect of the agents is the same as the sum of the individual effects of each agent when administered alone.

It is contemplated the therapeutic agent and the second agent may be given simultaneously in the same formulation. Alternatively, the second agents may be administered in a separate formulation but concurrently (i.e., given within less than one hour of each other).

In certain embodiments, the second agent useful in treating or preventing an age-related disorder or age-sensitive trait may be administered prior to administration of a therapeutic agent that selectively suppresses cellular senescence. Prior administration refers to administration of the second agent at least one hour prior to treatment with the therapeutic agent. It is also contemplated that the second agent may be administered subsequent to administration of the therapeutic agent. Subsequent administration is meant to describe administration of the second agent at least one hour after the administration of the therapeutic agent.

This disclosure contemplates a dosage unit comprising a pharmaceutical composition provided herein. Such dosage units include, for example, a single-dose or a multi-dose vial or syringe, including a two-compartment vial or syringe, one comprising the pharmaceutical composition of this disclosure in lyophilized form and the other a diluent for reconstitution. A multi-dose dosage unit can also be, e.g., a bag or tube for connection to an intravenous infusion device.

The following examples are for illustration and are not limiting.

EXAMPLES

Example 1

Preparation of P16-3MR Transgenic Mice

This Example describes preparation of a transgenic mouse comprising a p16$^{ink4}$ promoter operatively linked to a trimodal fusion protein.

The promoter, p16$^{ink4}$, which is transcriptionally active in senescent cells but not in non-senescent cells (see, e.g., Wang et al., *J. Biol. Chem.* 276:48655-61 (2001); Baker et al., *Nature*, supra) was engineered into a nucleic acid construct. The p16$^{Ink4}$ gene promoter (approximately 100 kilobase pairs) was introduced upstream of a nucleotide sequence encoding a trimodal reporter fusion protein. Alternatively, a truncated p16$^{Ink4}$ promoter may be used (see FIGS. 1 and 2 providing an exemplary vector and exemplary promoter sequence) (see, e.g., Baker et al., *Nature*, supra; International Application Publication No. WO/2012/177927; Wang et al., *J. Biol. Chem.* 276:48655-61 (2001)). The trimodal reporter protein, the expression of which is driven by the p16$^{ink4}$ promoter in senescent cells, is termed 3MR and consists of renilla luciferase (rLUC), monomeric red fluorescent protein (mRFP) and a truncated herpes simplex virus thymidine kinase (tTK) (see, e.g., Ray et al., *Cancer Res.* 64:1323-30 (2004)). The polypeptide sequences and the encoding polynucleotides for each of the three proteins are known in the art and are available in public databases, such as GenBank. An exemplary sequence (SEQ ID NO:25) for the 3MR transgene is provided in FIG. 3. The 3MR transgene was inserted into a BAC vector using techniques routinely practiced by person skilled in the molecular biology art. The detectable markers, rLUC and mRFP permitted detection of senescent cells by bioluminescence and fluorescence, respectively. The expression of tTK permitted selective killing of senescent cells by exposure to the pro-drug ganciclovir (GCV), which is converted to a cytotoxic moiety by tTK. Transgenic founder animals, which have a C57B16 background, were established and bred according to routinely procedures for introducing transgenes into animals (see, e.g., Baker et al., *Nature*, supra). The transgenic mice are called p16-3MR herein.

Example 2

Effects of Therapy-Induced Senescence on Aging

This example identifies the role of senescence-inducing stimuli, particularly radiation and chemotherapy treatment, on declining health parameters and age-sensitive traits using a p16-FKBP-caspase-8 (INK-ATTAC) transgenic animal model. In particular, the example determines the extent to which chemotherapy and gamma radiation induce cellular senescence, identifies that cellular senescence induced by various treatment regimens is deleterious for tissue structure and function, and identifies that clearance of therapy-induced senescent cells improves age-sensitive traits and other health parameters following chemotherapy and radiation.

Briefly, INK-ATTAC mice are aged 10-12 weeks. Cohorts of mice are treated with 4 Gy IR (4 cycles), doxorubicin (3-4 mg/kg i.p. daily for five consecutive days: 3 cycles), docetaxel (25 mg/kg i.p. every seven days for 3 cycles), or cisplatin (6 mg/kg i.p. every twenty days for 3 cycles) to induce cellular senescence. The mice are also treated with AP20187 or PBS on a weekly basis from the start of treatment.

The rate of aging is assessed by various measures of health and lifespan. Specifically, mice in each of the above cohorts are analyzed for the following age-sensitive traits, using methods known in the art, will not harm the animals, and do not require anesthesia: (1) T cell subset distribution, (2) cataract formation, (3) spontaneous activity, (4) motor coordination, and (5) cognitive capacity. These traits provide assessments of systems known to change with age and which have important implications for human health. Spontaneous activity of individual mice is measured over a 48-hour period using comprehensive laboratory animal monitoring systems equipped with photocells (e.g., Columbus Instruments). Motor coordination is analyzed by performing the accelerating rotarod test. For measuring cognitive capacity, a modified Stone T-maze, which is sensitive to age-related changes in learning and memory, is used.

Three additional age-sensitive traits known to change with age and highly relevant to human health are also measured using known techniques: (1) physical function, (2) body composition (sarcopenia, osteoporosis, fat atrophy), and (3) cardiac function. Physical function is assessed by measuring running time, distance, and work using a motorized treadmill, and grip strength using a grip meter. Lean mass, fat mass and bone mineral density is assessed by QNMR and/or dual-energy X-ray absorptiometry measurements.

The above analyses are complemented with assessments of age-sensitive traits on tissues and organs of test and control mice. These analyses include the following assays which are performed using known techniques: (1) fiber diameter analysis on gastrocnemius muscle, (2) DNA damage analysis, (3) analysis of renal and glomerulosclerosis, (4) analysis for retinal atrophy, (5) proteotoxic stress analysis, (6) oxidative stress analysis, and (7) analysis of the hematopoietic system.

Example 3

Effects of Removing Senescent Cells from Aging Animal

Clearance of therapy-induced senescent cells improves age-sensitive traits and other health parameters in aged animals. Wild type INK-ATTAC transgenic animals from each of lineage 3 (TG3) and lineage 5 (TG5) were used in the experiments (see Baker et al., *Nature*, supra). INK-ATTAC transgenic mice were aged 10-12 weeks, and then cohorts of animals were treated with AP20187 or PBS (control) on a weekly basis from the start of treatment. As shown in FIG. 4, animals treated with AP20187 had an average lifespan of approximately 26 months compared with 21 months for control.

Figure 5:
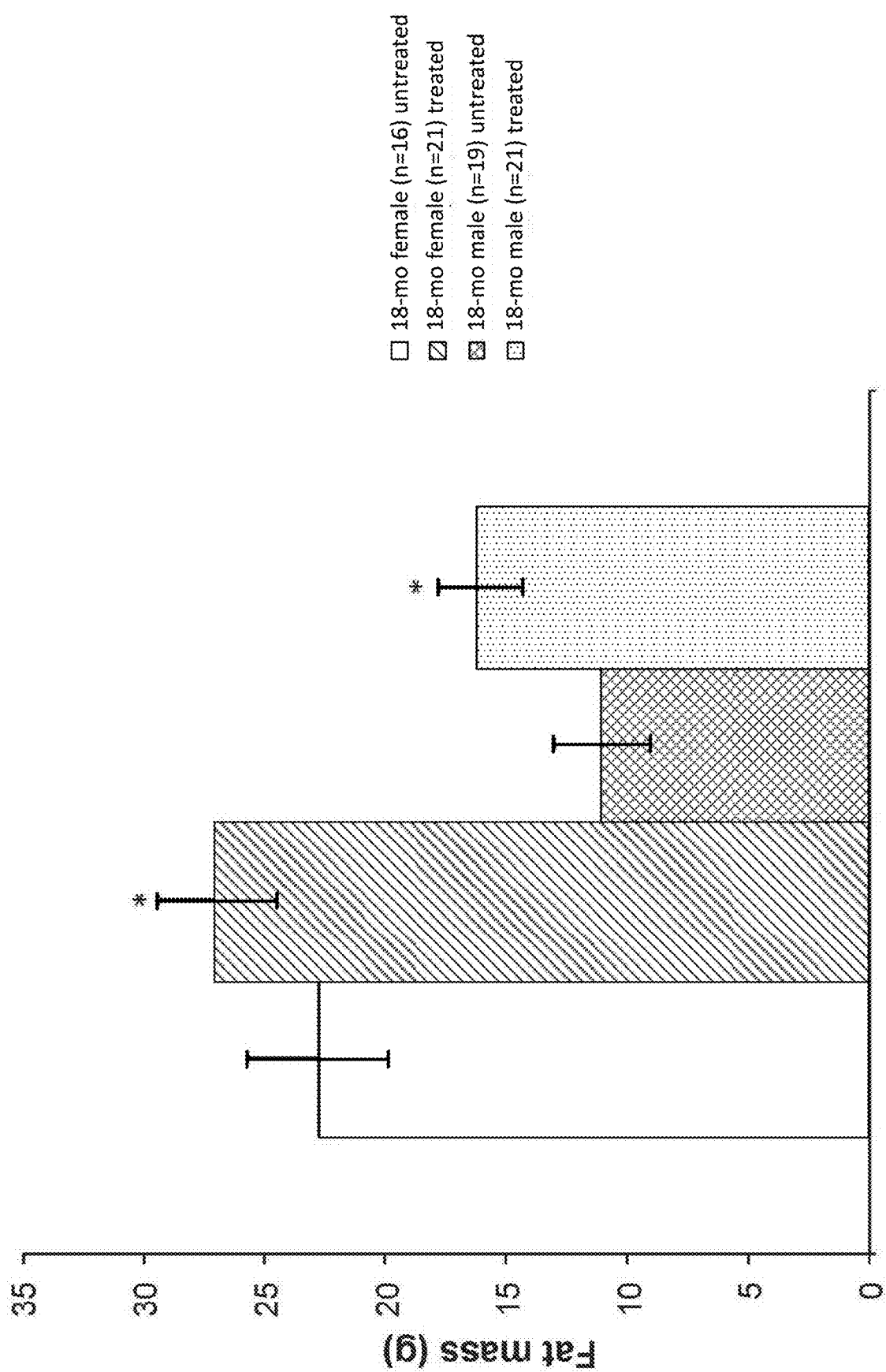
FIG. 5 shows fat mass measurements for 18-month wild-type INK-ATTAC transgenic mice treated with AP20187 or control INK-ATTAC animals (treated with PBS). Treated female mice were compared with untreated female mice, and treated male mice were compared with untreated male mice.
Figure 6:
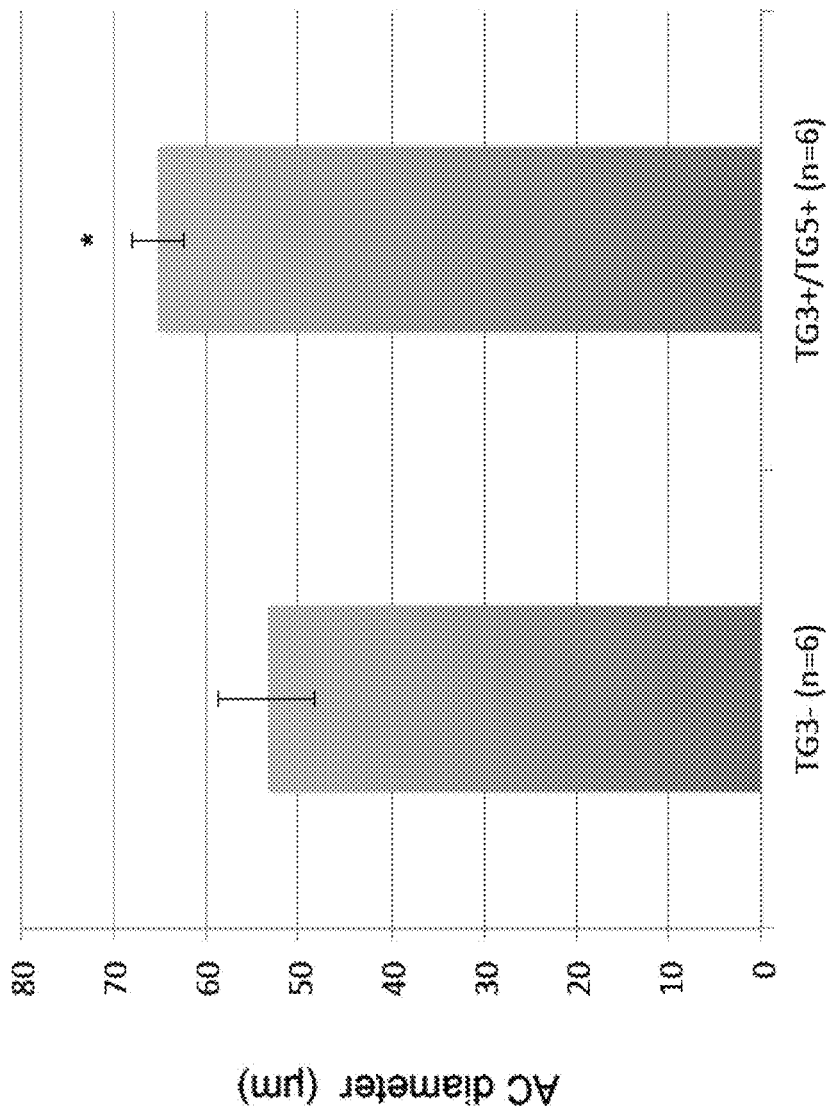
FIG. 6 illustrates the difference in adipose cell (AC) diameter in AP20187-treated wild-type INK-ATTAC transgenic mice (TG3+/TG5+, indicating mice from two different INK-ATTAC strains) and control untreated (PBS) INK-ATTAC animals (TG3−).
Figure 7:
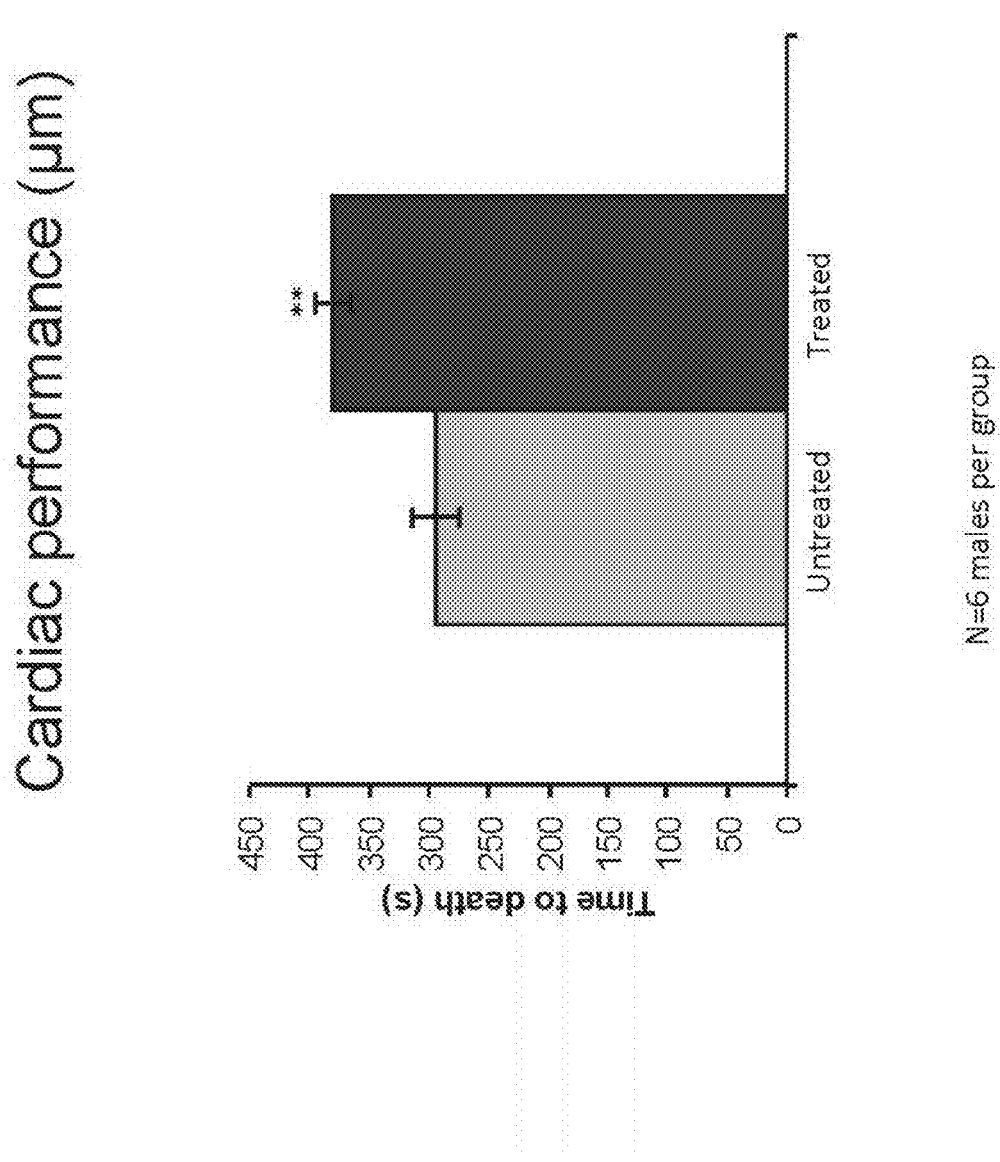
FIG. 7 illustrates cardiac performance of AP20187-treated wild-type INK-ATTAC transgenic mice (treated) and untreated (PBS) INK-ATTAC mice. Animals were injected with isoproterenol, as an exogenous stress, prior to sacrifice of the animals.
Figure 8:
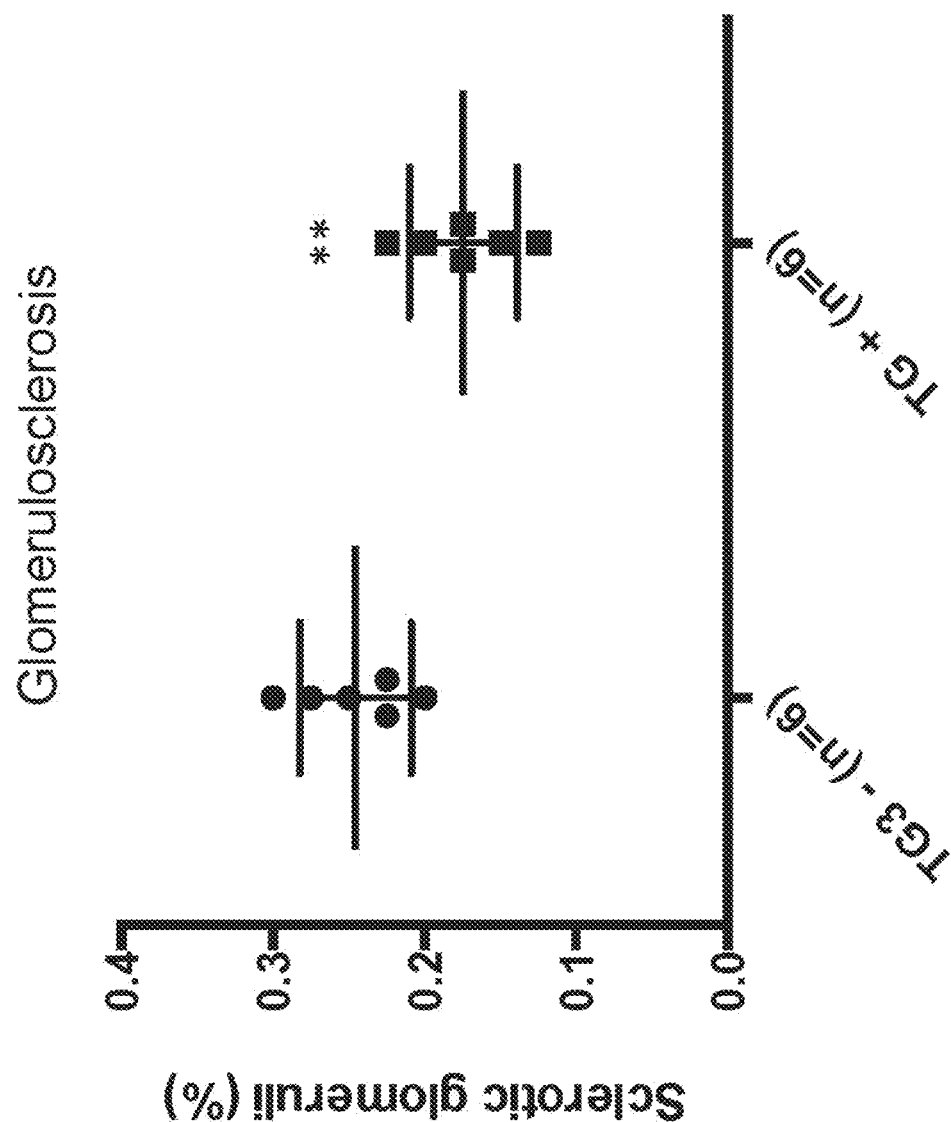
FIG. 8 shows the extent of glomerulosclerosis in AP20187-treated wild-type INK-ATTAC transgenic mice (TG+) and untreated (PBS) wild-type INK-ATTAC mice.

When the animals reached 18 months of age, several measures of health and lifespan were taken. Weight, fat mass, activity measurements (treadmill exercise tests to measure distance traveled and duration of exercise) were compared between untreated female mice (n=16) and AP20187-treated female mice (n=21), and compared between untreated male mice (n=19) and AP20187-treated male mice (n=21). Fat mass was greater in both treated females and males compared with the untreated groups (see FIG. 5). No statistically significant differences were observed with respect to weight, or activity measurements between the treated and untreated animals. Treated and untreated mice (5-6 per group) were sacrificed, and adipose cell (AC) diameter, gastrocnemius muscle fiber diameter (µm), abdominal muscle fiber diameter (µm), dermal thickness (µm), subdermal adipose thickness (µm), cardiac performance (introduction of isoproterenol as an exogenous stress in animals prior to sacrifice), and extent of glomerulosclerosis were determined. Treated animals had greater adipose cell diameter (see FIG. 6); better cardiac performance (FIG. 7); and had less sclerotic glomeruli (see FIG. 8) than untreated animals. No significant differences between treated animals were observed with respect to gastrocnemius muscle fiber diameter (µm), abdominal muscle fiber diameter (µm), dermal thickness (µm), and subdermal adipose thickness (µm). Removal of senescent cells in AP20187-treated animals prevented loss of adipose tissue, prevented loss of cardiac performance, and reduced the extent of glomerulosclerosis.

The various embodiments described above can be combined to provide further embodiments. All U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

SEQUENCE LISTING

<160> NUMBER OF SEQ ID NOS: 25

<210> SEQ ID NO 1
<211> LENGTH: 9267
<212> TYPE: DNA
<213> ORGANISM: Artificial Sequence
<220> FEATURE:
<223> OTHER INFORMATION: pBLUESCRIPT II KS vector containing a p16Ink4a
      promoter-FKBP-caspase-IRES-GFP nucleic acid construct

<400> SEQUENCE: 1
ctaaattgta agcgttaata ttttgttaaa attcgcgtta aatttttgtt aaatcagctc    60
attttttaac caataggccg aaatcggcaa aatcccttat aaatcaaaag aatagaccga   120

```
gataggggttg agtgttgttc cagtttggaa caagagtcca ctattaaaga acgtggactc    180
caacgtcaaa gggcgaaaaa ccgtctatca gggcgatggc ccactacgtg aaccatcacc    240
ctaatcaagt ttttgggggt cgaggtgccg taaagcacta atcggaacc ctaaagggag     300 cccccgattt agagcttgac ggggaaagcc ggcgaacgtg gcgagaaagg aagggaagaa    360
agcgaaagga gcgggcgcta gggcgctggc aagtgtagcg gtcacgctgc gcgtaaccac    420
cacacccgcc gcgcttaatg cgccgctaca gggcgcgtcc cattcgccat tcaggctgcg    480
caactgttgg gaagggcgat cggtgcgggc ctcttcgcta ttacgccagc tggcgaaagg    540
gggatgtgct gcaaggcgat taagttgggt aacgccaggg ttttcccagt cacgacgttg    600
taaaacgacg gccagtgagc gcgcgtaata cgactcacta gggcgaat tggagctcca     660 ccgcggtggc ggccgctcta gaactagtgg atccgtgtaa agtcactgct tttatagcta   720
catctgcata gatcccctgt atgaaagcat gtactacctg gataataata tctgtatttt   780
tctgtagtag gaaatcagtg tagttttaa aaccaaaaag tattgttatt aatctatctt    840
tgatctcaaa caatttcaat gacctagtat agtgattctc acggaaagcc ctgcaattta   900
ctcaaagcag ttttaaata ttgttttaaa agtgtgtgtg tgtgtgtgtg tgtgtgtgtg    960
tgtgtgtgtg tgttaaagt cattttcaaa ccccctcacaa tgtcttgaat gtgacatttg   1020
agtcatttat ggtaacttat aactcctttg aagaagttat tcagaattga ggttccagac   1080
acacaaatgc acaatacacc attttttcctt ccagttaaca atcagagggc aacacttatt   1140
tttaaaggaa aatcgactcc ataagggact ttataaaggg gtagacataa accagtatca   1200
gggataaact ctccgttccc ctgtttaacc taattttccc agggccatcc tggaatacga   1260
attttctctt gaaatacagt caaagaaaaa gtggtaggct acagagcaga ggaaacactg   1320
gacacagcga cccaccccag agtcacttcc cttaatctaa tgactaggtt ttttctgaaa   1380
gttattttgt tagaacacag gaacttttgc gaccacagtg atgctttag aggggtgaat    1440 cctcaaaaag aaaattaatc gcaactagta gaagggagat tacttattga ttcttataac   1500
ttctgcagga atacacagtt atgagttagg gcaaagagaa aattgacttt taatatctc    1560 tatcactaac atgagagaac atgtatgtgt tccaaaataa tttttattta ttgaaaaccc   1620
gctatatacc tggattttca cagaatattc attactctcc aaaatggcct tttctaggtg   1680
aattttattt tccttacaga cctcaagaag tttacataat ttacttaaac ctgaggagag   1740
agaacaaagc ctcagaaaat ttacatagtt tatttaaact aaactcagct tgcttggtag   1800
cagcttctaa tcccagcagt taaagagaca gaagcagggc caacctgggg tataatataa   1860
ggtgagactc tccttctttt ctctctgtct ctgtctgtct ctgtctctgt gtgtgtgtgt   1920
gtgtgtgtgt gtgtgtgtgt gtgtctcctc tctctctctc tctctctctc tctctctctc   1980
tctgtctctc tctccctccc cctccctccc tctccccctc ctctctccct ccctctccct   2040 ccccccccc cacacatttg aattcgtgga gttggtaaat gaggggtcag ttctctgtct   2100
gtctgtagtt ttgtgtccac aggatatgac tgacattctc accacacaca tacaaagtca   2160
aaaatagctg tggccatata aagaatatgg ggagagaaaa ttattcaaaa tctgcagaaa   2220
ataatgccag gcctttaatc ctggcaccca ggaggcagaa gggagacaga gttctgagtt   2280
tatgctgagt tccaggagtg aagaaaggg ccattgcctt tctggtgagg actgtctttt    2340
taaatcctcc cttctgtcca gtactggtaa ctctgcccaa agcgtgttct tcttcctgcc   2400
tcacaagatt gcaaagacgt ttttaacgaa caatttaaac cggtgcaacg tttatgcgca   2460
```

```
gcacaccaac tcatttaaac aaacaacagc cccataaaat agaaatactt tataagcaga   2520
ttgccctccg atgacttcac cccgtcactt ttttatagtt gtgtacagaa tcctagcact   2580
gatacagcaa catcagaaat gtttctgcaa atccttcgca aagattcgga tttcatactg   2640
ggcgtggtac cctccaaaat gagttgtttg agctagggtt gttgggatct cagcttggcg   2700
aagttgtagc tctttcttct gaataaaaga tgacacaatt ttctgctaag atgttaaata   2760
ccttaagttt cagtgtagtg atgaaaatta ccctccttcg ttttctaat acctgggtgt    2820 tgcactgggg aggaaggaga gatttcgaga aggactagtt cactttctca gaagacacgt   2880
gtgcacttct ttgctgtgcg ggtccagaag gagcccagcg tgtcaaaggg tgaccaggca   2940
tgggggaggg gtgttagcgt gggtagcagg cgggggctgt ccgatccttt agcgctgttt   3000
caacgcccag ctctcctcct gaaccctgca tctcttctgt agtccgggct ccatcccttt   3060 ccctccccc atccggaggt ggggggaaca gcagtgtttt caggggtgtt caattcatgc    3120
tatattcagg gcaaatagcg ccacctatgg cgggctgtgg agccaggtca ggagcagagt   3180
gtggctcccc cccccccca caccatcctc agaggaagga aggagggacc cactggtcac    3240
acgactgggc gattgggcgg gcactgaatc tccgcgagga aagcgaactc gaggagagcc   3300
atcacgcgta gcatggggag tagcaagagc aagcctaagg accccagcca gcgctctaga   3360
ggcgtccaag tcgaaaccat tagtcccggc gatggcagaa catttcctaa aagggggacaa   3420 acatgtgtcg tccattatac aggcatgttg gaggacggca aaaaggtgga cagtagtaga   3480
gatcgcaata aaccttcaa attcatgttg ggaaaacaag aagtcattag gggatgggag    3540
gagggcgtgg ctcaaatgtc cgtcggccaa cgcgctaagc tcaccatcag ccccgactac   3600
gcatacggcg ctaccggaca tcccggaatt attcccctc acgctacctt ggtgtttgac    3660
gtcgaactgt tgaagctcga gactagagga gtgcaggtgg agactatctc cccaggagac   3720
gggcgcacct tccccaagcg cggccagacc tgcgtggtgc actacaccgg gatgcttgaa   3780 gatgaaaga aagttgattc ctcccgggac agaaacaagc cctttaagtt tatgctaggc     3840
aagcaggagg tgatccgagg ctgggaagaa ggggttgccc agatgagtgt gggtcagaga   3900
gccaaactga ctatatctcc agattatgcc tatggtgcca ctgggcaccc aggcatcatc   3960
ccaccacatg ccactctcgt cttcgatgtg gagcttctaa aactggaaac tagtagtgaa   4020
tcacagactt tggacaaagt ttaccaaatg aaaagcaaac ctcggggata ctgtctgatc   4080
atcaacaatc acaattttgc aaaagcacgg gagaaagtgc ccaaacttca cagcattagg   4140
gacaggaatg gaacacactt ggatgcaggg gctttgacca cgacctttga agagcttcat   4200
tttgagatca agccccacga tgactgcaca gtagagcaaa tctatgagat tttgaaaatc   4260
taccaactca tggaccacag taacatggac tgcttcatct gctgtatcct ctcccatgga   4320
gacaagggca tcatctatgg cactgatgga caggaggccc ccatctatga gctgacatct   4380
cagttcactg gtttgaagtg cccttccctt gctggaaaac ccaaagtgtt tttattcag    4440 gcttgtcagg gggataacta ccagaaaggt atacctgttg agactgattc agaggagcaa   4500
ccctatttag aaatggattt atcatcacct caaacgagat atatcccgga tgaggctgac   4560
tttctgctgg ggatgccac tgtgaataac tgtgttttcct accgaaaccc tgcagaggga   4620
acctggtaca tccagtcact ttgccagagc ctgagagagc gatgtcctcg aggcgatgat   4680
attctcacca tcctgactga agtgaactat aagtaagca acaaggatga caagaaaaac   4740
atggggaaac agatgcctca gcctactttc acactaagaa aaaacttgt cttcccttct    4800 gatgattaca aggatgacga cgataagtga ggatcaacct cgaggaattc acgcgtttaa   4860
```

```
ttaactcgag gttttcgagg tcgacggtat cgataagctt gatatcgaat tccgcccctc    4920
tccctccccc cccctaacg ttactggccg aagccgcttg gaataaggcc ggtgtgcgtt    4980
tgtctatatg ttattttcca ccatattgcc gtcttttggc aatgtgaggg cccggaaacc    5040
tggccctgtc ttcttgacga gcattcctag gggtctttcc cctctcgcca aggaatgca    5100 aggtctgttg aatgtcgtga aggaagcagt tcctctggaa gcttcttgaa gacaaacaac    5160
gtctgtagcg acccttttgca ggcagcggaa cccccacct ggcgacaggt gcctctgcgg    5220
ccaaaagcca cgtgtataag atacacctgc aaaggcggca caaccccagt gccacgttgt    5280
gagttggata gttgtggaaa gagtcaaatg gctctcctca agcgtattca acaaggggct    5340
gaaggatgcc cagaaggtac cccattgtat gggatctgat ctggggcctc ggtgcacatg    5400
ctttacatgt gtttagtcga ggttaaaaaa acgtctaggc cccccgaacc acggggacgt    5460
ggttttcctt tgaaaaacac gatgataata tggccacaac catggtgagc aagggcgagg    5520
agctgttcac cggggtggtg cccatcctgg tcgagctgga cggcgacgta aacggccaca    5580
agttcagcgt gtccggcgag ggcgagggcg atgccaccta cggcaagctg accctgaagt    5640
tcatctgcac caccggcaag ctgcccgtgc cctggcccac cctcgtgacc accctgacct    5700
acggcgtgca gtgcttcagc cgctaccccg accacatgaa gcagcacgac ttcttcaagt    5760
ccgccatgcc cgaaggctac gtccaggagc gcaccatctt cttcaaggac gacggcaact    5820
acaagacccg cgccgaggtg aagttcgagg gcgacaccct ggtgaaccgc atcgagctga    5880
agggcatcga cttcaaggag gacggcaaca tcctggggca caagctggag tacaactaca    5940
acagccacaa cgtctatatc atggccgaca agcagaagaa cggcatcaag gtgaacttca    6000
agatccgcca caacatcgag gacggcagcg tgcagctcgc cgaccactac cagcagaaca    6060
cccccatcgg cgacggcccc gtgctgctgc ccgacaacca ctacctgagc acccagtccg    6120
ccctgagcaa agaccccaac gagaagcgcg atcacatggt cctgctggag ttcgtgaccg    6180
ccgccgggat cactctcggc atggacgagc tgtacaagta aagcggccgc gatctttttc    6240
cctctgccaa aaattatggg gacatcatga agccccttga gcatctgact tctggctaat    6300
aaaggaaatt tattttcatt gcaatagtgt gttggaattt tttgtgtctc tcactcggaa    6360
ggacatatgg gagggcaaat catttaaaac atcagaatga gtatttggtt tagagtttgg    6420
caacatatgc catatgctgg ctgccatgaa caaaggtggc tataaagagg tcatcagtat    6480
atgaaacagc cccctgctgt ccattcctta ttccatagaa aagccttgac ttgaggttag    6540 attttttta tattttgttt tgtgttattt ttttctttaa catccctaaa attttcctta    6600
catgttttac tagccagatt tttcctcctc tcctgactac tcccagtcat agctgtccct    6660
cttctcttat gaagatccct cgacctgcag cccaagcttg gcgtaatcat ggtcatagct    6720
gtttcctgtg tgaaattgtt atccgctcac aattccacac aacatacgag ccggaagcat    6780
aaagtgtaaa gcctggggtg cctaatgagt gagctaactc acattaattg cgttgcgctc    6840
actgcccgct ttccagtcgg gaaacctgtc gtgccagcgg atccgcatct caattagtca    6900
gcaaccatag tccgccccct aactccgccc atcccgcccc taactccgcc cagttccgcc    6960
cattctccgc cccatggctg actaattttt tttatttatg cagaggccga ggccgcctaa    7020
acggccggcc atcgataccg tcgacctcga ggggggcccc ggtacccagc ttttgttccc    7080
tttagtgagg gttaattgcg cgcttggcgt aatcatggtc atagctgttt cctgtgtgaa    7140
attgttatcc gctcacaatt ccacacaaca tacgagccgg aagcataaag tgtaaagcct    7200
```

| | | | | | |
|---|---|---|---|---|---|
| ggggtgccta | atgagtgagc | taactcacat | taattgcgtt | gcgctcactg | cccgctttcc | 7260
| agtcgggaaa | cctgtcgtgc | cagctgcatt | aatgaatcgg | ccaacgcgcg | gggagaggcg | 7320
| gtttgcgtat | tgggcgctct | tccgcttcct | cgctcactga | ctcgctgcgc | tcggtcgttc | 7380
| ggctgcggcg | agcggtatca | gctcactcaa | aggcggtaat | acggttatcc | acagaatcag | 7440
| gggataacgc | aggaaagaac | atgtgagcaa | aaggccagca | aaaggccagg | aaccgtaaaa | 7500
| aggccgcgtt | gctggcgttt | ttccataggc | tccgccccc | tgacgagcat | cacaaaaatc | 7560
| gacgctcaag | tcagaggtgg | cgaaacccga | caggactata | aagataccag | gcgtttcccc | 7620
| ctggaagctc | cctcgtgcgc | tctcctgttc | cgaccctgcc | gcttaccgga | tacctgtccg | 7680
| cctttctccc | ttcgggaagc | gtggcgcttt | ctcatagctc | acgctgtagg | tatctcagtt | 7740
| cggtgtaggt | cgttcgctcc | aagctgggct | gtgtgcacga | accccccgtt | cagcccgacc | 7800
| gctgcgcctt | atccggtaac | tatcgtcttg | agtccaaccc | ggtaagacac | gacttatcgc | 7860
| cactggcagc | agccactggt | aacaggatta | gcagagcgag | gtatgtaggc | ggtgctacag | 7920
| agttcttgaa | gtggtggcct | aactacggct | acactagaag | gacagtattt | ggtatctgcg | 7980
| ctctgctgaa | gccagttacc | ttcggaaaaa | gagttggtag | ctcttgatcc | ggcaaacaaa | 8040
| ccaccgctgg | tagcggtggt | ttttttgttt | gcaagcagca | gattacgcgc | agaaaaaaag | 8100
| gatctcaaga | agatcctttg | atcttttcta | cggggtctga | cgctcagtgg | aacgaaaact | 8160
| cacgttaagg | gattttggtc | atgagattat | caaaaaggat | cttcacctag | atccttttaa | 8220
| attaaaaatg | aagttttaaa | tcaatctaaa | gtatatatga | gtaaacttgg | tctgacagtt | 8280
| accaatgctt | aatcagtgag | gcacctatct | cagcgatctg | tctatttcgt | tcatccatag | 8340
| ttgcctgact | ccccgtcgtg | tagataacta | cgatacggga | gggcttacca | tctggcccca | 8400
| gtgctgcaat | gataccgcga | gacccacgct | caccggctcc | agatttatca | gcaataaacc | 8460
| agccagccgg | aagggccgag | cgcagaagtg | gtcctgcaac | tttatccgcc | tccatccagt | 8520
| ctattaattg | ttgccgggaa | gctagagtaa | gtagttcgcc | agttaatagt | ttgcgcaacg | 8580
| ttgttgccat | tgctacaggc | atcgtggtgt | cacgctcgtc | gtttggtatg | gcttcattca | 8640
| gctccggttc | ccaacgatca | aggcgagtta | catgatcccc | catgttgtgc | aaaaaagcgg | 8700
| ttagctcctt | cggtcctccg | atcgttgtca | gaagtaagtt | ggccgcagtg | ttatcactca | 8760
| tggttatggc | agcactgcat | aattctctta | ctgtcatgcc | atccgtaaga | tgcttttctg | 8820
| tgactggtga | gtactcaacc | aagtcattct | gagaatagtg | tatgcggcga | ccgagttgct | 8880
| cttgcccggc | gtcaatacgg | gataataccg | cgccacatag | cagaacttta | aaagtgctca | 8940
| tcattggaaa | acgttcttcg | gggcgaaaac | tctcaaggat | cttaccgctg | ttgagatcca | 9000
| gttcgatgta | acccactcgt | gcacccaact | gatcttcagc | atcttttact | ttcaccagcg | 9060
| tttctgggtg | agcaaaaaca | ggaaggcaaa | atgccgcaaa | aaagggaata | agggcgacac | 9120
| ggaaatgttg | aatactcata | ctcttccttt | ttcaatatta | ttgaagcatt | tatcagggtt | 9180
| attgtctcat | gagcggatac | atatttgaat | gtatttagaa | aaataaacaa | ataggggttc | 9240
| cgcgcacatt | tccccgaaaa | gtgccac | | | 9267

<210> SEQ ID NO 2
<211> LENGTH: 134
<212> TYPE: DNA
<213> ORGANISM: Artificial Sequence
<220> FEATURE:
<223> OTHER INFORMATION: 5 prime terminal synthetic vector sequence

<400> SEQUENCE: 2
ctaaattgta agcgttaata ttttgttaaa attcgcgtta aattttttgtt aaatcagctc    60 attttttaac caataggccg aaatcggcaa atcccttat aaatcaaaag aatagaccga    120
gatagggttg agtg    134

<210> SEQ ID NO 3
<211> LENGTH: 325
<212> TYPE: DNA
<213> ORGANISM: Artificial Sequence
<220> FEATURE:
<223> OTHER INFORMATION: F1 ori synthetic nucleotide sequence

<400> SEQUENCE: 3
ttgttccagt ttggaacaag agtccactat taaagaacgt ggactccaac gtcaaagggc    60
gaaaaaccgt ctatcagggc gatggcccac tacgtgaacc atcaccctaa tcaagttttt    120
tggggtcgag gtgccgtaaa gcactaaatc ggaaccctaa agggagcccc cgatttagag    180
cttgacgggg aaagccggcg aacgtggcga gaaaggaagg gaagaaagcg aaaggagcgg    240
gcgctagggc gctggcaagt gtagcggtca cgctgcgcgt aaccaccaca cccgccgcgc    300
ttaatgcgcc gctacagggc gcgtc    325

<210> SEQ ID NO 4
<211> LENGTH: 139
<212> TYPE: DNA
<213> ORGANISM: Artificial Sequence
<220> FEATURE:
<223> OTHER INFORMATION: LacZ alpha synthetic nucleotide sequence

<400> SEQUENCE: 4
ccattcgcca ttcaggctgc gcaactgttg ggaagggcga tcggtgcggg cctcttcgct    60
attacgccag ctggcgaaag ggggatgtgc tgcaaggcga ttaagttggg taacgccagg    120
gttttcccag tcacgacgt    139

<210> SEQ ID NO 5
<211> LENGTH: 26
<212> TYPE: DNA
<213> ORGANISM: Artificial Sequence
<220> FEATURE:
<223> OTHER INFORMATION: M13 fwd synthetic nucleotide sequence

<400> SEQUENCE: 5
tgtaaaacga cggccagtga gcgcgc    26

<210> SEQ ID NO 6
<211> LENGTH: 65
<212> TYPE: DNA
<213> ORGANISM: Artificial Sequence
<220> FEATURE:
<223> OTHER INFORMATION: T7 synthetic nucleotide sequence

<400> SEQUENCE: 6
gtaatacgac tcactatagg gcgaattgga gctccaccgc ggtggcggcc gctctagaac    60
tagtg    65

<210> SEQ ID NO 7
<211> LENGTH: 5
<212> TYPE: DNA
<213> ORGANISM: Artificial Sequence
<220> FEATURE:
<223> OTHER INFORMATION: p16 synthetic promoter sequence -continued

```
<400> SEQUENCE: 7 gatcc                                                                 5

<210> SEQ ID NO 8
<211> LENGTH: 13
<212> TYPE: DNA
<213> ORGANISM: Artificial Sequence
<220> FEATURE:
<223> OTHER INFORMATION: p16 synthetic promoter sequence

<400> SEQUENCE: 8
gtgtaaagtc act                                                       13

<210> SEQ ID NO 9
<211> LENGTH: 2604
<212> TYPE: DNA
<213> ORGANISM: Artificial Sequence
<220> FEATURE:
<223> OTHER INFORMATION: p16 synthetic promoter sequence

<400> SEQUENCE: 9
cttttatagc tacatctgca tagatcccct gtatgaaagc atgtactacc tggataataa    60
tatctgtatt tttctgtagt aggaaatcag tgtagttttt aaaaccaaaa agtattgtta   120
ttaatctatc tttgatctca aacaatttca atgacctagt atagtgattt ctacggaaag   180
ccctgcaatt tactcaaagc agttttaaa tattgtttta aaagtgtgtg tgtgtgtgtg    240
tgtgtgtgtg tgtgtgtgtg tggtgttaaa gtcattttca aaccccctcac aatgtcttga   300 atgtgacatt tgagtcattt atggtaactt ataactcctt tgaagaagtt attcagaatt   360
gaggttccag acacacaaat gcacaataca ccatttttcc ttccagttaa caatcagagg   420
gcaacactta tttttaaagg aaaatcgact ccataaggga cttataaaag gggtagacat   480
aaaccagtat cagggataaa ctctccgttc ccctgtttaa cctaattttc ccagggccat   540
cctggaatac gaattttctc ttgaaataca gtcaaagaaa aagtggtagg ctacagagca   600
gaggaaacac tggacacagc gacccacccc agagtcactt cccttaatct aatgactagg   660
ttttttctga agttatttt gttagaacac aggaactttt gcgaccacag tgatgctttt    720
agagggttga atcctcaaaa agaaaattaa tcgcaactag tagaagggag attacttatt   780
gattcttata acttctgcag gaatacacag ttatgagtta gggcaaagag aaaattgact   840
tttaatattc tctatcacta acatgagaga acatgtatgt gttccaaaat aattttatt    900 tattgaaaac ccgctatata cctggatttt cacagaatat tcattactct ccaaaatggc   960
cttttctagg tgaattttat tttccttaca gacctcaaga agtttacata atttacttaa  1020
acctgaggag agagaacaaa gcctcagaaa atttacatag tttattaa ctaaactcag    1080 cttgcttggt agcagcttct aatcccagca gttaaagaga cagaagcagg gccaacctgg   1140
ggtataatat aaggtgagac tctcctttct ttctctctgt ctctgtctgt ctctgtctct   1200
gtgtgtgtgt gtgtgtgtgt gtgtgtgtgt gtgtgtctcc tctctctctc tctctctctc   1260
tctctctctc tctctgtctc tctctccctc ccctccctc cctctccccc tcctctctcc    1320
ctccctctcc ctcccccccc cccacacatt tgaattcgtg gagttggtaa atgaggggtc   1380
agttctctgt ctgtctgtag ttttgtgtcc acaggatatg actgacattc tcaccacaca   1440
catacaaagt caaaaatagc tgtggccata taaagaatat ggggagagaa aattattcaa   1500
aatctgcaga aaataatgcc aggcctttaa tcctggcacc caggaggcag aagggagaca   1560
gagttctgag tttatgctga gttccaggag tggaagaaag ggccattgcc tttctggtga   1620
```

```
ggactgtctt tttaaatcct cccttctgtc cagtactggt aactctgccc aaagcgtgtt    1680
cttcttcctg cctcacaaga ttgcaaagac gttttaacg aacaatttaa accggtgcaa    1740
cgtttatgcg cagcacacca actcatttaa acaaacaaca gccccataaa atagaaatac    1800
tttataagca gattgccctc cgatgacttc accccgtcac ttttttatag ttgtgtacag    1860
aatcctagca ctgatacagc aacatcagaa atgtttctgc aaatccttcg caaagattcg    1920
gatttcatac tgggcgtggt accctccaaa atgagttgtt tgagctaggg ttgttgggat    1980
ctcagcttgg cgaagttgta gctctttctt ctgaataaaa gatgacacaa ttttctgcta    2040
agatgttaaa taccttaagt ttcagtgtag tgatgaaaat taccctcctt cgttttctcta   2100 atacctgggt gttgcactgg ggaggaagga gagatttcga aaggactag ttcactttct     2160 cagaagacac gtgtgcactt ctttgctgtg cgggtccaga aggagcccag cgtgtcaaag    2220
ggtgaccagg catggggggag gggtgttagc gtgggtagca ggcgggggct gtccgatcct   2280
ttagcgctgt ttcaacgccc agctctcctc ctgaaccctg catctcttct gtagtccggg    2340
ctccatccct ttcccctccc ccatccggag gtgggggaa cagcagtgtt ttcaggggtg     2400
ttcaattcat gctatattca gggcaaatag cgccacctat ggcgggctgt ggagccaggt    2460
caggagcaga gtgtggctcc ccccccccc cacaccatcc tcagaggaag aaggaggga     2520 cccactggtc acacgactgg gcgattgggc gggcactgaa tctccgcgag gaaagcgaac    2580
tcgaggagag ccatcacgcg tagc                                          2604
```

<210> SEQ ID NO 10
<211> LENGTH: 702
<212> TYPE: DNA
<213> ORGANISM: Artificial Sequence
<220> FEATURE:
<223> OTHER INFORMATION: FKBP synthetic nucleotide sequence

<400> SEQUENCE: 10

```
atggggagta gcaagagcaa gcctaaggac cccagccagc gctctagagg cgtccaagtc      60
gaaaccatta gtcccggcga tggcagaaca tttcctaaaa ggggacaaac atgtgtcgtc     120
cattatacag gcatgttgga ggacggcaaa aaggtggaca gtagtagaga tcgcaataaa     180
cctttcaaat tcatgttggg aaaacaagaa gtcattaggg gatgggagga gggcgtggct     240
caaatgtccg tcggccaacg cgctaagctc accatcagcc ccgactacgc atacggcgct     300
accggacatc ccggaattat tccccctcac gctaccttgg tgtttgacgt cgaactgttg     360
aagctcgaga ctagaggagt gcaggtggag actatctccc caggagacgg gcgcaccttc     420
cccaagcgcg ccagacctg cgtggtgcac tacaccggga tgcttgaaga tggaaagaaa     480
gttgattcct cccgggacag aaacaagccc tttaagttta tgctaggcaa gcaggaggtg     540
atccgaggct gggaagaagg ggttgcccag atgagtgtgg gtcagagagc caaactgact     600
atatctccag attatgccta tggtgccact gggcacccag gcatcatccc accacatgcc     660
actctcgtct tcgatgtgga gcttctaaaa ctggaaacta gt                         702
```

<210> SEQ ID NO 11
<211> LENGTH: 789
<212> TYPE: DNA
<213> ORGANISM: Artificial Sequence
<220> FEATURE:
<223> OTHER INFORMATION: Casp8 synthetic nucleotide sequence

<400> SEQUENCE: 11

```
agtgaatcac agactttgga caaagtttac caaatgaaaa gcaaacctcg gggatactgt    60
ctgatcatca acaatcacaa ttttgcaaaa gcacgggaga aagtgcccaa acttcacagc   120
attagggaca ggaatggaac acacttggat gcagggggctt tgaccacgac ctttgaagag   180
cttcattttg agatcaagcc ccacgatgac tgcacagtag agcaaatcta tgagattttg   240
aaaatctacc aactcatgga ccacagtaac atggactgct catctgctg tatcctctcc   300 catggagaca agggcatcat ctatggcact gatggacagg aggcccccat ctatgagctg   360
acatctcagt tcactggttt gaagtgccct tcccttgctg gaaaacccaa agtgtttttt   420
attcaggctt gtcaggggga taactaccag aaaggtatac ctgttgagac tgattcagag   480
gagcaaccct atttagaaat ggatttatca tcacctcaaa cgagatatat cccggatgag   540
gctgactttc tgctggggat ggccactgtg aataactgtg tttcctaccg aaaccctgca   600
gagggaacct ggtacatcca gtcactttgc cagagcctga gagagcgatg tcctcgaggc   660
gatgatattc tcaccatcct gactgaagtg aactatgaag taagcaacaa ggatgacaag   720
aaaaacatgg ggaaacagat gcctcagcct actttcacac taagaaaaaa acttgtcttc   780
ccttctgat                                                           789

<210> SEQ ID NO 12
<211> LENGTH: 27
<212> TYPE: DNA
<213> ORGANISM: Artificial Sequence
<220> FEATURE:
<223> OTHER INFORMATION: Flag synthetic nucleotide sequence

<400> SEQUENCE: 12
gattacaagg atgacgacga taagtga                                        27

<210> SEQ ID NO 13
<211> LENGTH: 5
<212> TYPE: DNA
<213> ORGANISM: Artificial Sequence
<220> FEATURE:
<223> OTHER INFORMATION: 3 prime UTR synthetic nucleotide sequence

<400> SEQUENCE: 13 ggatc                                                                 5

<210> SEQ ID NO 14
<211> LENGTH: 39
<212> TYPE: DNA
<213> ORGANISM: Artificial Sequence
<220> FEATURE:
<223> OTHER INFORMATION: Multiple cloning site synthetic nucleotide
      sequence

<400> SEQUENCE: 14
aacctcgagg aattcacgcg tttaattaac tcgaggttt                           39

<210> SEQ ID NO 15
<211> LENGTH: 1268
<212> TYPE: DNA
<213> ORGANISM: Artificial Sequence
<220> FEATURE:
<223> OTHER INFORMATION: IRES GFP synthetic nucleotide sequence

<400> SEQUENCE: 15
tcgaggtcga cggtatcgat aagcttgata tcgaattccg cccctctccc tcccccccc    60 ctaacgttac tggccgaagc cgcttggaat aaggccggtg tgcgtttgtc tatatgttat   120
```

```
tttccaccat attgccgtct tttggcaatg tgagggcccg gaaacctggc cctgtcttct    180
tgacgagcat tcctaggggt ctttcccctc tcgccaaagg aatgcaaggt ctgttgaatg    240
tcgtgaagga agcagttcct ctggaagctt cttgaagaca acaacgtct gtagcgaccc     300 tttgcaggca gcggaacccc ccacctggcg acaggtgcct ctgcggccaa aagccacgtg    360
tataagatac acctgcaaag gcggcacaac cccagtgcca cgttgtgagt tggatagttg    420
tggaaagagt caaatggctc tcctcaagcg tattcaacaa ggggctgaag gatgcccaga    480
aggtacccca ttgtatggga tctgatctgg ggcctcggtg cacatgcttt acatgtgttt    540
agtcgaggtt aaaaaaacgt ctaggccccc cgaaccacgg ggacgtggtt ttcctttgaa    600
aaacacgatg ataatatggc cacaaccatg gtgagcaagg gcgaggagct gttcaccggg    660
gtggtgccca tcctggtcga gctggacggc gacgtaaacg gccacaagtt cagcgtgtcc    720
ggcgagggcg agggcgatgc cacctacggc aagctgaccc tgaagttcat ctgcaccacc    780
ggcaagctgc ccgtgccctg gcccaccctc gtgaccaccc tgacctacgg cgtgcagtgc    840
ttcagccgct accccgacca catgaagcag cacgacttct tcaagtccgc catgcccgaa    900
ggctacgtcc aggagcgcac catcttcttc aaggacgacg gcaactacaa gacccgcgcc    960
gaggtgaagt tcgagggcga caccctggtg aaccgcatcg agctgaaggg catcgacttc    1020
aaggaggacg gcaacatcct ggggcacaag ctggagtaca actacaacag ccacaacgtc   1080
tatatcatgg ccgacaagca gaagaacggc atcaaggtga acttcaagat ccgccacaac   1140
atcgaggacg gcagcgtgca gctcgccgac cactaccagc agaacacccc catcggcgac   1200
ggccccgtgc tgctgcccga caaccactac ctgagcaccc agtccgccct gagcaaagac   1260
cccaacga                                                            1268

<210> SEQ ID NO 16
<211> LENGTH: 565
<212> TYPE: DNA
<213> ORGANISM: Artificial Sequence
<220> FEATURE:
<223> OTHER INFORMATION: Rabbit B-globin PA synthetic nucleotide
      sequence

<400> SEQUENCE: 16
gaagcgcgat cacatggtcc tgctggagtt cgtgaccgcc gccgggatca ctctcggcat    60
ggacgagctg tacaagtaaa gcggccgcga tcttttttccc tctgccaaaa attatgggga   120
catcatgaag ccccttgagc atctgacttc tggctaataa aggaaattta ttttcattgc    180
aatagtgtgt tggaattttt tgtgtctctc actcggaagg acatatggga gggcaaatca    240
tttaaaacat cagaatgagt atttggttta gagtttggca acatatgcca tatgctggct    300
gccatgaaca aaggtggcta taagagggtc atcagtatat gaaacagccc ctgctgtcc    360 attccttatt ccatagaaaa gccttgactt gaggttagat ttttttttata tttgttttg    420 tgttattttt tcttttaaca tccctaaaat tttccttaca tgttttacta gccagatttt    480
tcctcctctc ctgactactc ccagtcatag ctgtccctct tctcttatga agatccctcg    540
acctgcagcc aagcttggc gtaat                                           565

<210> SEQ ID NO 17
<211> LENGTH: 26
<212> TYPE: DNA
<213> ORGANISM: Artificial Sequence
<220> FEATURE:
<223> OTHER INFORMATION: M13-rev synthetic nucleotide sequence
```

<400> SEQUENCE: 17
catggtcata gctgtttcct gtgtga                                              26

<210> SEQ ID NO 18
<211> LENGTH: 285
<212> TYPE: DNA
<213> ORGANISM: Artificial Sequence
<220> FEATURE:
<223> OTHER INFORMATION: LacO synthetic nucleotide sequence

<400> SEQUENCE: 18
aattgttatc cgctcacaat tccacacaac atacgagccg gaagcataaa gtgtaaagcc         60
tggggtgcct aatgagtgag ctaactcaca ttaattgcgt tgcgctcact gcccgctttc        120
cagtcgggaa acctgtcgtg ccagcggatc cgcatctcaa ttagtcagca accatagtcc        180
cgcccctaac tccgcccatc ccgccccctaa ctccgcccag ttccgcccat tctccgcccc      240
atggctgact aatttttttt atttatgcag aggccgaggc cgcct                        285

<210> SEQ ID NO 19
<211> LENGTH: 58
<212> TYPE: DNA
<213> ORGANISM: Artificial Sequence
<220> FEATURE:
<223> OTHER INFORMATION: Fse1 linker synthetic nucleotide sequence

<400> SEQUENCE: 19
aaacggccgg ccatcgatac cgtcgacctc gagggggggc ccggtaccca gcttttgt          58

<210> SEQ ID NO 20
<211> LENGTH: 37
<212> TYPE: DNA
<213> ORGANISM: Artificial Sequence
<220> FEATURE:
<223> OTHER INFORMATION: T3 synthetic nucleotide sequence

<400> SEQUENCE: 20
tccctttagt gagggttaat tgcgcgcttg gcgtaat                                  37

<210> SEQ ID NO 21
<211> LENGTH: 26
<212> TYPE: DNA
<213> ORGANISM: Artificial Sequence
<220> FEATURE:
<223> OTHER INFORMATION: M13-rev synthetic nucleotide sequence

<400> SEQUENCE: 21
catggtcata gctgtttcct gtgtga                                              26

<210> SEQ ID NO 22
<211> LENGTH: 362
<212> TYPE: DNA
<213> ORGANISM: Artificial Sequence
<220> FEATURE:
<223> OTHER INFORMATION: LacO synthetic nucleotide sequence

<400> SEQUENCE: 22
aattgttatc cgctcacaat tccacacaac atacgagccg gaagcataaa gtgtaaagcc         60
tggggtgcct aatgagtgag ctaactcaca ttaattgcgt tgcgctcact gcccgctttc        120
cagtcgggaa acctgtcgtg ccagctgcat taatgaatcg gccaacgcgc ggggagaggc        180
ggtttgcgta ttgggcgctc ttccgcttcc tcgctcactg actcgctgcg ctcggtcgtt        240
cggctgcggc gagcggtatc agctcactca aaggcggtaa tacggttatc cacagaatca        300

```
gggggataacg caggaaagaa catgtgagca aaaggccagc aaaaggccag gaaccgtaaa    360
aa                                                                   362
```

<210> SEQ ID NO 23
<211> LENGTH: 780
<212> TYPE: DNA
<213> ORGANISM: Artificial Sequence
<220> FEATURE:
<223> OTHER INFORMATION: ColE1 origin synthetic nucleotide sequence

<400> SEQUENCE: 23

```
ggccgcgttg ctggcgtttt tccataggct ccgcccccct gacgagcatc acaaaaatcg     60
acgctcaagt cagaggtggc gaaacccgac aggactataa agataccagg cgtttccccc    120
tggaagctcc ctcgtgcgct ctcctgttcc gaccctgccg cttaccggat acctgtccgc    180
ctttctccct tcgggaagcg tggcgctttc tcatagctca cgctgtaggt atctcagttc    240
ggtgtaggtc gttcgctcca agctgggctg tgtgcacgaa ccccccgttc agcccgaccg    300
ctgcgcctta tccggtaact atcgtcttga gtccaacccg gtaagacacg acttatcgcc    360
actggcagca gccactggta acaggattag cagagcgagg tatgtaggcg gtgctacaga    420
gttcttgaag tggtggccta actacggcta cactagaagg acagtatttg gtatctgcgc    480
tctgctgaag ccagttacct tcggaaaaag agttggtagc tcttgatccg gcaaacaaac    540
caccgctggt agcggtggtt ttttgtttg caagcagcag attacgcgca gaaaaaaagg    600
atctcaagaa gatcctttga tcttttctac ggggtctgac gctcagtgga acgaaaactc    660
acgttaaggg attttggtca tgagattatc aaaaaggatc ttcacctaga tccttttaaa    720
ttaaaaatga agttttaaat caatctaaag tatatatgag taaacttggt ctgacagtta    780
```

<210> SEQ ID NO 24
<211> LENGTH: 986
<212> TYPE: DNA
<213> ORGANISM: Artificial Sequence
<220> FEATURE:
<223> OTHER INFORMATION: AmpR synthetic nucleotide sequence

<400> SEQUENCE: 24

```
ccaatgctta atcagtgagg cacctatctc agcgatctgt ctatttcgtt catccatagt     60
tgcctgactc cccgtcgtgt agataactac gatacgggag ggcttaccat ctggccccag    120
tgctgcaatg ataccgcgag acccacgctc accggctcca gatttatcag caataaacca    180
gccagccgga agggccgagc gcagaagtgg tcctgcaact ttatccgcct ccatccagtc    240
tattaattgt tgccgggaag ctagagtaag tagttcgcca gttaatagtt tgcgcaacgt    300
tgttgccatt gctacaggca tcgtggtgtc acgctcgtcg tttggtatgg cttcattcag    360
ctccggttcc caacgatcaa ggcgagttac atgatccccc atgttgtgca aaaaagcggt    420
tagctccttc ggtcctccga tcgttgtcag aagtaagttg gccgcagtgt tatcactcat    480
ggttatggca gcactgcata attctcttac tgtcatgcca tccgtaagat gcttttctgt    540
gactggtgag tactcaacca agtcattctg agaatagtgt atgcggcgac cgagttgctc    600
ttgcccggcg tcaatacggg ataataccgc gccacatagc agaactttaa aagtgctcat    660
cattggaaaa cgttcttcgg ggcgaaaact ctcaaggatc ttaccgctgt tgagatccag    720
ttcgatgtaa cccactcgtg cacccaactg atcttcagca tcttttactt tcaccagcgt    780
ttctgggtga gcaaaaacag gaaggcaaaa tgccgcaaaa aagggaataa gggcgacacg    840
```

-continued

```
gaaatgttga atactcatac tcttcctttt tcaatattat tgaagcattt atcagggtta      900
ttgtctcatg agcggataca tatttgaatg tatttagaaa aataaacaaa tagggggttcc     960
gcgcacattt ccccgaaaag tgccac                                           986
```

<210> SEQ ID NO 25
<211> LENGTH: 2664
<212> TYPE: DNA
<213> ORGANISM: Artificial Sequence
<220> FEATURE:
<223> OTHER INFORMATION: p16-3MR synthetic transgene nucleotide sequence

<400> SEQUENCE: 25

```
atggcttcca aggtgtacga ccccgagcaa cgcaaacgca tgatcactgg gcctcagtgg       60
tgggctcgct gcaagcaaat gaacgtgctg gactccttca tcaactacta tgattccgag      120
aagcacgccg agaacgccgt gattttctg catggtaacg ctgcctccag ctacctgtgg       180
aggcacgtcg tgcctcacat cgagcccgtg gctagatgca tcatccctga tctgatcgga      240
atgggtaagt ccggcaagag cgggaatggc tcatatcgcc tcctggatca ctacaagtac      300
ctcaccgctt ggttcgagct gctgaacctt ccaaagaaaa tcatctttgt gggccacgac      360
tgggggcgtt gtctggcctt tcactactcc tacgagcacc aagacaagat caaggccatc      420
gtccatgctg agagtgtcgt ggacgtgatc gagtcctggg acgagtggcc tgacatcgag      480
gaggatatcg ccctgatcaa gagcgaagag ggcgagaaaa tggtgcttga gaataacttc      540
ttcgtcgaga ccatgctccc aagcaagatc atgcggaaac tggagcctga ggagttcgct      600
gcctacctgg agccattcaa ggagaagggc gaggttagac ggcctaccct ctcctggcct      660
cgcgagatcc ctctcgttaa gggaggcaag cccgacgtcg tccagattgt ccgcaactac      720
aacgcctacc tcgggccag cgacgatctg cctaagatgt tcatcgagtc cgaccctggg       780
ttcttttcca acgctattgt cgagggagct aagaagttcc ctaacaccga gttcgtgaag      840
gtgaagggcc tccacttcag ccaggaggac gctccagatg aaatgggtaa gtacatcaag      900
agcttcgtgg agcgcgtgct gaagaacgag cagctcgaga attctcacgc gtctgcagga      960
tatcaagctt ccaccatggc ctcctccgag gacgtcatca gttcatgcg cttcaaggtg     1020
cgcatggagg gctccgtgaa cggccacgag ttcgagatcg agggcgaggg cgagggccgc     1080
ccctacgagg gcacccagac cgccaagctg aaggtgacca agggcggccc cctgcccttc     1140
gcctgggaca tcctgtcccc tcagttccag tacggctcca aggcctacgt gaagcacccc     1200
gccgacatcc ccgactactt gaagctgtcc ttccccgagg gcttcaagtg ggagcgcgtg     1260
atgaacttcg aggacggcgg cgtggtgacc gtgacccagg actcctccct gcaggacggc     1320
gagttcatct acaaggtgaa gctgcgcggc accaacttcc cctccgacgg ccccgtaatg     1380
cagaagaaga ccatgggctg ggaggcctcc accgagagga tgtacccgga ggacggcgcc     1440
ctgaagggcg agatcaagat gaggctgaag ctgaaggacg gcggccacta cgacgccgag     1500
gtcaagacca cctacatggc caagaagccc gtgcagctgc ccggcgccta caagaccgac     1560
atcaagctgg acatcaccct ccacaacgag gactacacca tcgtggaaca gtacgagcgc     1620
gccgagggcc gccactccac cggcgccacc gcggcccgg atccgccac catgcccacg     1680
ctactgcggg tttatataga cggtccccac gggatgggga aaaccaccac caccacgcaa     1740
ctgctggtgg ccctgggttc gcgcgacgat atcgtctacg tacccgagcc gatgacttac     1800
tggcgggtgc tgggggcttc cgagacaatc gcgaacatct acaccacaca acaccgcctc     1860
gaccagggtg agatatcggc cggggacgcg gcggtggtaa tgacaagcgc ccagataaca     1920
```

-continued

```
atgccttatg ccgtgaccga cgccgttctg gctcctcata tcgggggga ggctgggagc    1980 tcacatgccc cgcccccggc cctcaccatc ttcctcgacc gccatcccat cgccttcatg    2040
ctgtgctacc cggccgcgcg gtaccttatg ggcagcatga cccccaggc cgtgctggcg     2100 ttcgtggccc tcatcccgcc gaccttgccc ggcaccaaca tcgtgcttgg ggcccttccg    2160
gaggacagac acatcgaccg cctggccaaa cgccagcgcc ccggcgagcg gctggacctg    2220
gctatgctgg ctgcgattcg ccgcgtttac gggctacttg ccaatacggt gcggtatctg    2280
cagtgcggcg ggtcgtggcg ggaggactgg ggacagcttt cggggacggc cgtgccgccc    2340
cagggtgccg agcccagag caacgcgggc ccacgacccc atatcgggga cacgttattt     2400
accctgtttc gggccccga gttgatggcc cccaacggcg acctgtataa cgtgtttgcc     2460
tgggccttgg acgtcttggc caaacgcctc cgttccatgc acgtctttat cctggattac    2520
gaccaatcgc ccgccggctg ccgggacgcc ctgctgcaac ttacctccgg gatggtccag    2580
acccacgtca ccaccccgg ctccataccg acgatatgcg acctggcgcg cacgtttgcc     2640
cgggagatgg gggaggctaa ctga                                          2664
```

We claim the following:

1. A nucleic acid construct comprising a p16$^{INK4a}$ promoter sequence operably linked to a nucleic acid sequence encoding an enzyme such that the enzyme is expressed when the construct is present in senescent cells;
   wherein the enzyme has enzymatic activity that converts a particular prodrug to a cytotoxic agent;
   wherein administering the prodrug to a tissue that contains senescent cells expressing the enzyme results in the prodrug being converted to the cytotoxic agent, thereby selectively killing the senescent cells but killing less than 10% of non-senescent cells in the same tissue;
   whereby progression of an age-related disorder or an age-sensitive trait is delayed in the tissue compared with a tissue to which the prodrug is not administered.

2. The nucleic acid construct of claim 1, wherein the p16$^{INK4a}$ promoter also controls expression of a luminescent protein so as to cause it to be expressed in senescent cells.

3. The nucleic acid construct of claim 1, wherein the p16$^{INK4a}$ promoter also controls expression of a fluorescent protein so as to cause it to be expressed in senescent cells.

4. The nucleic acid construct of claim 1, wherein the enzyme is a thymidine kinase.

5. The nucleic acid construct of claim 1, wherein the particular prodrug is ganciclovir.

6. The nucleic acid construct of claim 2, wherein the luminescent protein is luciferase.

7. The nucleic acid construct of claim 3, wherein the fluorescent protein is monomeric red fluorescent protein (mRFP).

8. A method of genetically altering a host cell, comprising transfecting the host cell with a nucleic acid construct according to claim 1.

9. A genetically altered senescent cell containing a nucleic acid according to claim 1.

10. A method of killing a senescent cell, comprising contacting a genetically altered senescent cell according to claim 9 with the prodrug.

* * * * *